US011760807B2

(12) United States Patent
Ohtomo et al.

(10) Patent No.: US 11,760,807 B2
(45) Date of Patent: Sep. 19, 2023

(54) GPC3-TARGETING DRUG WHICH IS ADMINISTERED TO PATIENT RESPONSIVE TO GPC3-TARGETING DRUG THERAPY

(71) Applicants: Chugai Seiyaku Kabushiki Kaisha, Tokyo (JP); F. Hoffmann-La Roche AG, Basel (CH)

(72) Inventors: Toshihiko Ohtomo, Tokyo (JP); Takayoshi Tanaka, Tokyo (JP); Yasuo Sugitani, Tokyo (JP); Oscar Puig, Jersey City, NJ (US); Ruey-min Lee, Short Hills, NJ (US); Gong Chen, Rutherford, NJ (US); Anton Belousov, Penzberg (DE); Ya-Chi Chen, Hoboken, NJ (US); Bernhard Reis, Basel (CH)

(73) Assignees: Chugai Seiyaku Kabushiki Kaisha, Tokyo (JP); F. Hoffmann-La Roche AG, Basel (CH)

( * ) Notice: Subject to any disclaimer, the term of this patent is extended or adjusted under 35 U.S.C. 154(b) by 0 days.

(21) Appl. No.: 15/309,391

(22) PCT Filed: May 8, 2015

(86) PCT No.: PCT/JP2015/002352
§ 371 (c)(1),
(2) Date: Nov. 7, 2016

(87) PCT Pub. No.: WO2015/170480
PCT Pub. Date: Nov. 12, 2015

(65) Prior Publication Data
US 2017/0073426 A1    Mar. 16, 2017

Related U.S. Application Data

(60) Provisional application No. 61/990,238, filed on May 8, 2014.

(51) Int. Cl.
| C07K 16/30 | (2006.01) |
| G01N 33/574 | (2006.01) |
| G01N 33/50 | (2006.01) |
| G01N 33/53 | (2006.01) |
| G01N 33/569 | (2006.01) |
| C12Q 1/6886 | (2018.01) |
| A61K 39/00 | (2006.01) |

(52) U.S. Cl.
CPC .......... *C07K 16/303* (2013.01); *C12Q 1/6886* (2013.01); *G01N 33/5011* (2013.01); *G01N 33/56972* (2013.01); *G01N 33/57438* (2013.01); *A61K 2039/505* (2013.01); *A61K 2039/55* (2013.01); *C07K 2317/24* (2013.01); *C07K 2317/732* (2013.01); *C07K 2317/92* (2013.01); *C12Q 2600/106* (2013.01); *C12Q 2600/156* (2013.01); *C12Q 2600/158* (2013.01); *G01N 2800/52* (2013.01); *G01N 2800/7028* (2013.01)

(58) Field of Classification Search
CPC .............. A61K 39/395; A61K 2039/55; A61K 2039/505; A61K 2039/585; G01N 2800/52; G01N 33/56972; G01N 33/5011; G01N 33/57438; G01N 2800/7028
See application file for complete search history.

(56) References Cited

U.S. PATENT DOCUMENTS

| 5,322,678 | A | 6/1994 | Morgan, Jr. et al. |
| 5,693,762 | A | 12/1997 | Queen et al. |
| 6,436,411 | B1 | 8/2002 | Riordan et al. |
| 6,617,156 | B1 | 9/2003 | Doucette-Stamm et al. |
| 6,737,056 | B1 | 5/2004 | Presta |
| 7,297,775 | B2 | 11/2007 | Idusogie et al. |
| 7,317,091 | B2 | 1/2008 | Lazar et al. |
| 7,691,586 | B2 | 4/2010 | Watanabe et al. |

(Continued)

FOREIGN PATENT DOCUMENTS

| CA | 2 451 493 A1 | 1/2003 |
| CA | 2 801 911 A1 | 3/2004 |

(Continued)

OTHER PUBLICATIONS

IKhantasup et al., Monoclonal Antibodies in Immunodiagnosis and Immunotherapy, 34(6): 404-417. (Year: 2015).*

(Continued)

Primary Examiner — Hong Sang
(74) Attorney, Agent, or Firm — Nixon & Vanderhye P.C.

(57) ABSTRACT

A method is provided for determining the efficacy of GPC3-targeting drug therapy for cancer in a patient before the start of GPC3-targeting drug therapy or for determining the continuation of GPC3-targeting drug therapy for a patient treated with GPC3-targeting therapy. The method includes determining the number of an immunocyte or an expression level of a molecule expressed on the immunocyte in a biological sample isolated from the patient before the start of GPC3-targeting drug therapy and/or the patient treated with the GPC3-targeting drug therapy, wherein when the number of the immunocyte or the expression level of the molecule expressed on the immunocyte is a predetermined value, the efficacy of the GPC3-targeting drug therapy is determined or the continuation of the GPC3-targeting drug therapy is determined. GPC3-targeting drugs and drug preparations for use according to the disclosed methods are also provided.

10 Claims, 8 Drawing Sheets

Specification includes a Sequence Listing.

(56) References Cited

U.S. PATENT DOCUMENTS

| | | | |
|---|---|---|---|
| 7,744,880 B2 | 6/2010 | Aburatani et al. | |
| 7,867,734 B2 | 1/2011 | Nakano et al. | |
| 7,871,613 B2 | 1/2011 | Kinoshita et al. | |
| 7,919,086 B2 | 4/2011 | Nakano et al. | |
| 8,263,077 B2 | 9/2012 | Aburatani et al. | |
| 8,497,355 B2 | 7/2013 | Igawa et al. | |
| 8,663,929 B2 | 3/2014 | Kataoka et al. | |
| 8,937,158 B2 | 1/2015 | Lazar et al. | |
| 9,096,651 B2 | 8/2015 | Igawa et al. | |
| 9,102,739 B2 | 8/2015 | Lazar et al. | |
| 9,513,292 B2 | 12/2016 | Aburatani et al. | |
| 10,731,127 B2 | 8/2020 | Ll et al. | |
| 10,782,300 B2 | 9/2020 | Ohtomo et al. | |
| 2002/0102254 A1 | 8/2002 | Leung et al. | |
| 2004/0110226 A1 | 6/2004 | Lazar et al. | |
| 2004/0236080 A1 | 11/2004 | Aburatani et al. | |
| 2005/0054832 A1 | 3/2005 | Lazar et al. | |
| 2005/0171339 A1 | 8/2005 | Sugo et al. | |
| 2005/0233392 A1 | 10/2005 | Filmus et al. | |
| 2006/0014223 A1 | 1/2006 | Aburatani et al. | |
| 2006/0040325 A1 | 2/2006 | Wu et al. | |
| 2006/0167232 A1 | 7/2006 | Aburatani et al. | |
| 2006/0188510 A1 | 8/2006 | Aburatani et al. | |
| 2006/0246550 A1 | 11/2006 | Okumura | |
| 2007/0087005 A1 | 4/2007 | Lazar et al. | |
| 2007/0190599 A1 | 8/2007 | Nakano et al. | |
| 2007/0258981 A1* | 11/2007 | Hilbert | C07K 16/465 424/138.1 |
| 2007/0269444 A1* | 11/2007 | Kinoshita | C07K 16/303 424/155.1 |
| 2008/0003623 A1 | 1/2008 | Nakajima et al. | |
| 2008/0008710 A1 | 1/2008 | Aburatani et al. | |
| 2008/0124330 A1 | 5/2008 | Nakano et al. | |
| 2008/0138827 A1 | 6/2008 | Watanabe et al. | |
| 2008/0166756 A1 | 7/2008 | Tsuchiya et al. | |
| 2009/0060907 A1 | 3/2009 | Aburatani et al. | |
| 2010/0167315 A1 | 7/2010 | Thibault et al. | |
| 2010/0239577 A1 | 9/2010 | Igawa et al. | |
| 2010/0248359 A1* | 9/2010 | Nakano | C07K 16/303 435/325 |
| 2011/0033452 A1 | 2/2011 | Nakano et al. | |
| 2011/0091907 A1 | 4/2011 | Kataoka et al. | |
| 2011/0104157 A1 | 5/2011 | Kinoshita et al. | |
| 2012/0128678 A1 | 5/2012 | Aburatani et al. | |
| 2015/0098941 A1 | 4/2015 | Lazar et al. | |
| 2015/0210763 A1 | 7/2015 | Kuramochi et al. | |
| 2015/0259417 A1 | 9/2015 | Nakano et al. | |
| 2015/0285806 A1 | 10/2015 | Ohtomo et al. | |
| 2015/0315278 A1 | 11/2015 | Igawa et al. | |

FOREIGN PATENT DOCUMENTS

| | | |
|---|---|---|
| CN | 1646155 A | 7/2005 |
| CN | 1678740 A | 10/2005 |
| CN | 101377506 A | 3/2009 |
| CN | 102027372 A | 4/2011 |
| CN | 102046200 A | 5/2011 |
| CN | 102276721 A | 12/2011 |
| CN | 102770530 A | 11/2012 |
| EP | 0329185 A2 | 8/1989 |
| EP | 1411118 A1 | 4/2004 |
| EP | 1541680 A1 | 6/2005 |
| EP | 1541686 A1 | 6/2005 |
| EP | 1548442 A1 | 6/2005 |
| EP | 1674111 A1 | 6/2006 |
| EP | 1816140 A1 | 8/2007 |
| EP | 1829962 A1 | 9/2007 |
| EP | 1548442 B1 | 1/2011 |
| EP | 2647706 A1 | 10/2013 |
| EP | 2863224 A1 | 4/2015 |
| EP | 2937697 A1 | 10/2015 |
| JP | H02028200 A | 1/1990 |
| JP | 2007093274 A | 4/2007 |
| JP | 2007300927 A | 11/2007 |
| JP | 2009232848 A | 10/2009 |
| JP | 2015511702 A | 4/2015 |
| KR | 20100132060 A | 12/2010 |
| KR | 20110005812 A | 1/2011 |
| KR | 101300545 B1 | 9/2013 |
| RU | 2001124907 A | 6/2003 |
| WO | WO-9954342 A1 | 10/1999 |
| WO | WO-0042072 A2 | 7/2000 |
| WO | WO-0047228 A1 | 8/2000 |
| WO | WO-0061739 A1 | 10/2000 |
| WO | WO-0231140 A1 | 4/2002 |
| WO | WO-0240545 A2 | 5/2002 |
| WO | WO-02079255 A1 | 10/2002 |
| WO | WO-03000883 A1 | 1/2003 |
| WO | WO 03057881 A1 | 7/2003 |
| WO | WO03068257 A1 | 8/2003 |
| WO | WO-03100429 A2 | 12/2003 |
| WO | WO-2004022597 A1 | 3/2004 |
| WO | WO-2004022739 A1 | 3/2004 |
| WO | WO-2004022754 A1 | 3/2004 |
| WO | WO-2004023145 A1 | 3/2004 |
| WO | WO-2004029207 A2 | 4/2004 |
| WO | WO-2004038420 A1 | 5/2004 |
| WO | WO-2004065540 A2 | 8/2004 |
| WO | WO-2004099249 A2 | 11/2004 |
| WO | WO-2005023301 A1 | 3/2005 |
| WO | WO-2005070963 A1 | 8/2005 |
| WO | WO-2005106485 A1 | 11/2005 |
| WO | WO-2006006693 A1 | 1/2006 |
| WO | WO-2006020114 A2 | 2/2006 |
| WO | WO-2006023403 A2 | 3/2006 |
| WO | WO-2006031370 A2 | 3/2006 |
| WO | WO-2006038588 A1 | 4/2006 |
| WO | WO-2006046751 A1 | 5/2006 |
| WO | WO-2006067913 A1 | 6/2006 |
| WO | WO-2006105338 A2 | 10/2006 |
| WO | WO-2006116260 A2 | 11/2006 |
| WO | WO-2007005612 A2 | 1/2007 |
| WO | WO-2007021841 A2 | 2/2007 |
| WO | WO-2007024249 A2 | 3/2007 |
| WO | WO-2007041635 A2 | 4/2007 |
| WO | WO-2007047291 A2 | 4/2007 |
| WO | WO-2007059782 A1 | 5/2007 |
| WO | WO-2007137170 A2 | 11/2007 |
| WO | WO-2008032217 A2 | 3/2008 |
| WO | WO-2008046085 A2 | 4/2008 |
| WO | WO-2008092117 A2 | 7/2008 |
| WO | WO-2009041062 A1 | 4/2009 |
| WO | WO-2009086320 A1 | 7/2009 |
| WO | WO-2009116659 A1 | 9/2009 |
| WO | WO-2009122667 A1 | 10/2009 |
| WO | WO-2009140242 A1 | 11/2009 |
| WO | WO2011057034 A2 | 5/2011 |
| WO | WO-2012145469 A1 | 10/2012 |
| WO | WO-2013118858 A1 | 8/2013 |
| WO | WO-2013127465 A1 | 9/2013 |
| WO | WO2013181543 A1 | 12/2013 |
| WO | WO-2014097648 A1 | 6/2014 |

OTHER PUBLICATIONS

Rudikoff et al., Proc. Natl. Acad. Sci. USA, 79(6):1979-1983. (Year: 1982).*
Colman, Research in Immunology, 145:33-36. (Year: 1994).*
Gluck et al., Clin. Cancer Res., 10: 2253-2264 (Year: 2004).*
Hatjiharissi et al., Blood, 106, Abstract 776. (Year: 2005).*
Hatjiharissi et al., Blood, 110(7): 2561-2564. (Year: 2007).*
Tefferi et al., Mayo Clin Proc., 80(7): 923-936. (Year: 2005).*
Bosire et al., AIDS Research Therapy, 2013, 10:24, pp. 1-7.*
Fischer et al., Experimental Hematology, 2006, 34: 753-759.*
Alley, S.C., et al., "Antibody-drug Conjugates: Targeted Drug Delivery for Cancer," Current Opinion in Chemical Biology 14(4):529-537, Elsevier, England (2010).
Bendig, M.M., "Humanization of Rodent Monoclonal Antibodies by CDR Grafting," Methods: A Companion to Methods in Enzymology 8(2):83-93, Academic Press, United States (1995).

(56) References Cited

OTHER PUBLICATIONS

Bigge, J.C., et al., "Nonselective and Efficient Fluorescent Labeling of Glycans Using 2-Amino Benzamide and Anthranilic Acid," Analytical Biochemistry 230(2):229-238, Academic Press, United States (1995).

Bolognesi, A., et al., "A Comparison of Anti-lymphocyte Immunotoxins Containing Different Ribosome-inactivating Proteins and Antibodies," Clinical and Experimental Immunology 89(3):341-346, Blackwell Scientific Publications, England (1992).

Bosch, F.X., et al., "Primary Liver Cancer: Worldwide Incidence and Trends," Gastroenterology 127(5 Suppl 1):S5-S16, W.B. Saunders, United States (2004).

Capurro, M., et al., "Glypican-3: a Novel Serum and Histochemical Marker for Hepatocellular Carcinoma," Gastroenterology 125(1):89-97, W.B. Saunders, United States (2003).

Capurro, M.I., et al., "Glypican-3 Promotes the Growth of Hepatocellular Carcinoma by Stimulating Canonical Wnt Signaling," Cancer Research 65(14):6245-6254, American Association for Cancer Research, United States (2005).

Casellas, P., et al., "Trichokirin, a Ribosome-inactivating Protein From the Seeds of Trichosanthes Kirilowii Maximowicz. Purification, Partial Characterization and Use for Preparation of Immunotoxins," European Journal of Biochemistry 176(3):581-588, Blackwell Science Ltd, England (1988).

Cheng, A.L., et al., "Efficacy and Safety of Sorafenib in Patients in the Asia-pacific Region with Advanced Hepatocellular Carcinoma: A Phase III Randomised, Double-blind, Placebo-controlled Trial," The Lancet Oncology 10(1):25-34, Lancet Pub. Group, England (2009).

Cheng, W., et al., "Glypican-3-mediated Oncogenesis Involves the Insulin-like Growth Factor-signaling Pathway," Carcinogenesis 29(7):1319-1326, Oxford University Press, England (2008).

Cumber, A.J., et al., "Purification of Immunotoxins Containing the Ribosome-inactivating Proteins Gelonin and Momordin Using High Performance Liquid Immunoaffinity Chromatography Compared With Blue Sepharose CI-6b Affinity Chromatography," Journal of Immunological Methods 135(1-2):15-24, Elsevier, Netherlands (1990).

Davis, J.H., et al., "SEEDbodies: Fusion Proteins Based on Strand-exchange Engineered Domain (SEED) CH3 Heterodimers in an Fc Analogue Platform for Asymmetric Binders or Immunofusions and Bispecific Antibodies.," Protein Engineering, Design & Selection 23(4):195-202, Oxford University Press, England (2010).

De Cat, B., et al., "Processing by Proprotein Convertases Is Required for Glypican-3 Modulation of Cell Survival, Wnt Signaling, and Gastrulation Movements," The Journal of Cell Biology 163(3):625-635, Rockefeller University Press, United States (2003).

Endo, M., "A Novel Molecular Targeted Therapy, Humanized Anti-glypican 3 Antibody (Gc33), for the Treatment of Unresectable Hepatocellular Cancer," Medical Science Digest 39(9):40-43 (2013).

Fischer, L., et al., "The Anti-lymphoma Effect of Antibody-mediated Immunotherapy is Based on an Increased Degranulation of Peripheral Blood Natural Killer (NK) Cells," Experimental Hematology 34(6):753-759, Elsevier Science Inc., Netherlands (2006).

Forster, A.C., et al., "Programming Peptidomimetic Syntheses by Translating Genetic Codes Designed De Novo," Proceedings of the National Academy of Sciences USA 100(11):6353-6357, National Academy of Sciences, United States (2003).

Fulton, R.J., et al., "Purification of Ricin A1, A2, and B Chains and Characterization of Their Toxicity," The Journal of Biological Chemistry 261(12):5314-5319, American Society for Biochemistry and Molecular Biology, United States (1986).

Ghetie, V., et al., "The GLP Large scale Preparation of Immunotoxins Containing Deglycosylated Ricin A Chain and a Hindered Disulfide Bond," Journal of Immunological Methods 142(2):223-230, Elsevier, Netherlands (1991).

Hashiguchi, A., et al., "Using Immunofluorescent Digital Slide Technology to Quantify Protein Expression in Archival Paraffin-embedded Tissue Sections," Pathology International 60(11):720-725, Japanese Society of Pathology, Australia (2010).

Ho, M. and Kim, H., "Glypican-3: A New Target for Cancer Immunotherapy," European Journal of Cancer 47(3):333-338, Elsevier Science Ltd., England (2011).

Houdebine, L.M., "Production of Pharmaceutical Proteins from Transgenic Animals," Journal of Biotechnology 34(3):269-287, Elsevier Science, Netherlands (1994).

Ikeda, M., et al., "Japanese Phase I Study of GC33, a Humanized Antibody Against Glypican-3 for Advanced Hepatocellular Carcinoma," Cancer Science 105(4):455-462, Japanese Cancer Association, England (2014).

International Search Report for International Application No. PCT/JP2015/002352, Japan Patent Office, Tokyo, dated Jul. 28, 2015, 9 pages.

Ishiguro, T., et al., "Anti-Giypican 3 Antibody as a Potential Antitumor Agent for Human Liver Cancer," Cancer Research 68(23):9832-9838, American Association for Cancer Research, United States (2008).

Kamori, H., et al., "Identification of HIA-A2- or HLA-A24-restricted CTL Epitopes Possibly Useful for Glypican-3-specific Immunotherapy of Hepatocellular Carcinoma," Clinical Cancer Research 12(9):2689-2697, The Association, United States (2006).

Kappel, C.A., et al., "Regulating Gene Expression in Transgenic Animals," Current Opinion in Biotechnology 3(5):548-553, Elsevier, England (1992).

Kawaida, M., et al., "Clinicopathological Significance of the Expression of Glypican-3 in Hepatocellular Carcinoma," Proceedings of the Japanese Society of Pathology 104(1):324, The Japanese Society of Pathology, Japan (2015).

Konno, Y., et al., "Fucose Content of Monoclonal Antibodies can be Controlled by Culture Medium Osmolality for High Antibody-dependent Cellular Cytotoxicity," Cytotechnology 64(3):249-265, Kluwer Academic Publishers (2012).

Kunkel, J.P., et al., "Comparisons of the Glycosylation of a Monoclonal Antibody Produced Under Nominally Identical Cell Culture Conditions in Two Different Bioreactors," Biotechnology Progress 16(3):462-470, Wiley-Blackwell, United States (2000).

Kunkel, T.A., et al., "Rapid and Efficient Site-Specific Mutagenesis Without Phenotypic Selection," Proceedings of the National Academy of Sciences USA 82(2):488-492, National Academy of Sciences, United States (1985).

Lage, H., et al., "Expression of a Glypican-related 62-kDa Antigen Is Decreased in Hepatocellular Carcinoma in Correspondence to the Grade of Tumor Differentiation," Virchows Arch 438(6):567-573, Springer International, Germany (2001).

Lazar, G.A., et al., "Engineered Antibody Fc Variants with Enhanced Effector Function," Proceedings of the National Academy of Sciences USA 103(11):4005-4010, National Academy of Sciences, United States (2006).

Llovet, J.M., et al., "Hepatocellular Carcinoma," Lancet 362(9399):1907-1917, Lancet Publishing Group, England (2003).

Llovet, J.M., et al., "Sorafenib in Advanced Hepatocellular Carcinoma," The New England Journal of Medicine 359(4):378-390, Massachusetts Medical Society, United States (2008).

McCarty, K.S., et al., "Use of a Monoclonal Anti-estrogen Receptor Antibody in the Immunohistochemical Evaluation of Human Tumors," Cancer Research 46(8 Suppl):4244s-4248s, American Association for Cancer Research, United States (1986).

Midorikawa, Y., et al., "Glypican-3, Overexpressed in Hepatocellular Carcinoma, Modulates FGF2 and BMP-7 Signaling," International Journal of Cancer 103(4):455-465, Wiley-Liss, United States (2003).

Office Action dated Jan. 19, 2017, in U.S. Appl. No. 14/713,416, Nakano, K. et al., filed May 15, 2015.

Ofuji, K. and Nakatsura, T., "Vaccine Therapy for Hepatic Cancer," Consensus of Cancer Therapy 12(2):114-116, Herusu Shuppan Co., Japan (2013).

Pai, L.H., et al., "Treatment of Advanced Solid Tumors with Immunotoxin LMB-1: An Antibody Linked to Pseudomonas Exotoxin," Nature Medicine 2(3):350-353, Nature Publishing Company, United States (1996).

Paul, W.E., "Structure and Function of Immunoglobulins," in Fundamental Immunology, Third Edition, pp. 292-295, Raven Press, New York, United States (1993).

(56) References Cited

OTHER PUBLICATIONS

Portolano, S., et al., "Lack of Promiscuity in Autoantigen-Specific H and L Chain Combinations as Revealed by Human H and L Chain 'Roulette'," The Journal of Immunology 150(3):880-887, The American Association of Immunologists, United States (1993).
Presta, L.G., "Molecular Engineering and Design of Therapeutic Antibodies," Current Opinion in Immunology 20(4):460-470, Elsevier, England (2008).
Raju, T.S., "Glycosylation Variations with Expression Systems and their Impact on Biological Activity of Therapeutic Immunoglobulins," BioProcess International 44-53 (2003).
Satoh, M., et al., "Non-Fucosylated Therapeutic Antibodies as Next-Generation Therapeutic Antibodies," Expert Opinion on Biological Therapy 6(11):1161-1173, Taylor and Francis, England (2006).
Schenk, B., et al., "MPDU1 Mutations Underlie a Novel Human Congenital Disorder of Glycosylation, Designated Type If," The Journal of Clinical Investigation 108(11):1687-1695, American Society for Clinical Investigation, United States (2001).
Sivam, G., et al., "Immunotoxins to a Human Melanoma-associated Antigen: Comparison of Gelonin with Ricin and other A Chain Conjugates," Cancer Research 47(12):3169-3173, American Association for Cancer Research, United States (1987).
Stirpe, F. and Barbieri, L., "Ribosome-inactivating Proteins Up to Date," FEBS Letters 195(1-2):1-8, John Wiley & Sons Ltd., England (1986).
Strohl, W.R., "Optimization of Fc-mediated Effector Functions of Monoclonal Antibodies," Current Opinion in Biotechnology 20(6):685-691, Elsevier, England (2009).
Sung, Y.K., et al., "Glypican-3 is Overexpressed in Human Hepatocellular Carcinoma," Cancer Science 94(3):259-262, Blackwell Publishing, England (2003).
Takenaka, K., et al., "Results of 280 Liver Resections for Hepatocellular Carcinoma," Archives of Surgery 131:71-76, American Medical Association, United States (1996).
Thorpe, P.E., et al., "New Coupling Agents for the Synthesis of Immunotoxins Containing a Hindered Disulfide Bond with Improved Stability in Vivo," Cancer Research 47(22):5924-5931, American Association for Cancer Research, United States (1987).
Traister, A., et al., "Mammalian Notum Induces the Release of Glypicans and Other Gpi-anchored Proteins From the Cell Surface," The Biochemical Journal 410(3):503-511, Portland Press, England (2008).
Vaupel, P., et al., "Blood Flow, Oxygen and Nutrient Supply, and Metabolic Microenvironment of Human Tumors: A Review," Cancer Research 49(23):6449-6665, American Association for Cancer Research, United States (1989).
Wall, R.J., "Transgenic Livestock: Progress and Prospects for the Future," Theriogenology 45(1):57-68, Elsevier Science Inc., United States (1996).
Wang, L., et al., "Expanding the Genetic Code," Annual Review of Biophysics and Biomolecular Structure 35:225-249, Annual Reviews, United States (2006).
Wang, L., et al., "Quantitating Fluorescence Intensity From Fluorophores: Practical Use of MESF Values," Journal of Research of the National Institute of Standards and Technology 107(4):339-353, National Institute of Standards and Technology, United States (2002).
Wawrzynczak, E.J., et al., "Molecular and Biological Properties of an Abrin a Chain Immunotoxin Designed for Therapy of Human Small Cell Lung Cancer," British Journal of Cancer 66(2):361-366, Nature Publishing Group, England (1992).
Wawrzynczak, E.J., et al., "Pharmacokinetics in the Rat of a Panel of Immunotoxins Made with Abrin A Chain, Ricin A Chain, Gelonin, and Momordin," Cancer Research 50(23):7519-7526, American Association for Cancer Research, United States (1990).
Weitzhandler, M., et al., "Analysis of Carbohydrates On IgG Preparations," Journal of Pharmaceutical Sciences 83(12):1670-1675, American Pharmaceutical Assn, United States (1994).
Weng, W.K., et al., "Two Immunoglobulin G Fragment C Receptor Polymorphisms Independently Predict Response to Rituximab in Patients with Follicular Lymphoma," Journal of Clinical Oncology 21(21):3940-3947, American Society of Clinical Oncology, United States (2003).
Yamane-Ohnuki, N., et al., "Establishment of FUT8 Knockout Chinese Hamster Ovary Cells: An Ideal Host Cell Line For Producing Completely Defucosylated Antibodies with Enhanced Antibody-Dependent Cellular Cytotoxicity," Biotechnology and Bioengineering 87(5):614-622, Wiley, United States (2004).
Yeo, W., et al., "Randomized Phase III Study of Doxorubicin Versus Cisplatin/Interferon alpha—2b/Doxorubicin/Fluorouracil (PIAF) Combination Chemotherapy for Unresectable Hepatocellular Carcinoma," Journal National Cancer Institute 97(20):1532-1538, Oxford University Press, United States (2005).
Zhu, A.X., et al., "First-in-man Phase I Study of GC33, a Novel Recombinant Humanized Antibody Against Glypican-3, in Patients with Advanced Hepatocellular Carcinoma," Clinical Cancer Research 19(4):920-928, The Association, United States (2013).
Declaration of Dr. Greg A. Lazar dated Dec. 27, 2010, in U.S. Appl. No. 11/841,654, Lazar, G.A., et al., filed Aug. 20, 2007, 4 pages.
Hearing Notice in Reference of Application No. 2347/CHENP/2008, dated Mar. 3, 2017, Indian Patent Office, 1 page.
Lund, J., et al., "Multiple Interactions of IgG with its Core Oligosaccharide Can Modulate Recognition by Complement and Human Fcγ Receptor I and Influence the Synthesis of its Oligosaccharide Chains," Journal of Immunology 157(11):4963-4969, American Association of Immunologists, United States (1996).
Office Action dated Apr. 4, 2017, in U.S. Appl. No. 14/505,932, Lazar, G.A., et al., filed Oct. 3, 2014, 50 pages.
Office Action dated Mar. 24, 2017, in U.S. Appl. No. 14/629,967, Igawa, T. et al., filed Feb. 24, 2015, 17 pages.
Ghose, T.I., et al., "Preparation of antibody-linked cytotoxic agents," Methods in Enzymology 93:280-333, Elsevier Inc., United States (1983).
Clinicaltrials.Gov Archive, "A Phase I Study of GC33 in Advances or Metastatic Liver Cancer (Hepatocellular Carcinoma)," NCT00746317, Updated on Nov. 16, 2010, accessed at https://clinicaltrials.gov/archive/NCT00746317/2010_11_16, 4 pages.
Examination Report dated Apr. 12, 2017, from the Government of India, Patent Application No. 6501/CHENP/2010 filed on Oct. 12, 2010, 7 pages.
Llovet, J.M., et al., "A Molecular Signature to Discriminate Dysplastic Nodules From Early Hepatocellular Carcinoma in HCV Cirrhosis," Gastroenterology 131(6):1758-1767, W.B. Saunders, United States (2006).
Nakatsura, T. et al., "Glypican-3, Overexpressed Specifically in Human Hepatocellular Carcinoma, is a Novel Tumor Marker," Biochemical and Biophysical Research Communications 306(1):16-25, Academic Press, New York (2003).
Office Action dated Jan. 9, 2017, in U.S. Appl. No. 14/441,551, Ohtomo, T., et al., filed May 8, 2015, 15 pages.
Ghetie, M.A., et al., "Homodimerization of Tumor-Reactive Monoclonal Antibodies Markedly Increases their Ability to Induce Growth Arrest or Apoptosis of Tumor Cells," Proceedings of the National Academy of Sciences USA 94(14):7509-7514, National Academy of Sciences, United States (1997).
Indian Hearing Notice of Application No. 1929/CHENP/2006, dated Jul. 19, 2017.
Takai, H., et al., "Histopathological analyses of the antitumor activity of anti-glypican-3 antibody (GC33) in human liver cancer xenograft models," Cancer Biology & Therapy 8(10):930-938 (2009).
Yen, C. J., et al., "Randomized phase II trial of intravenous RO5137382/GC33 at 1600 mg every other week in placebo in previously treated patients with unresectable advanced hepatocellular carcinoma (HCC; NCT01507168)," J Clin Oncol 32(15):suppl 4102 (2014), Abstract.
Abou-Alfa, G. K., et al. "Randomized phase II placebo controlled study of codrituzumab in previously treated patients with advanced hepatocellular carcinoma," J Hepatology 65(2):289-295 (2016).
Sawada, Y., et al., "Phase I Trial of a Glypican-3-Derived Peptide Vaccine for Advanced Hepatocellular Carcinoma: Immunologic

(56) References Cited

OTHER PUBLICATIONS

Evidence and Potential for Improving Overall Survival," Clin Cancer Res 18(13):3686-3696 (2012).
Colman, P. M., "Effects of amino acid sequence changes on antibody-antigen interactions," Research in Immunology 145:33-36 (1994).
Gluck, W. L., et al., "Phase I Studies of Interleukin (IL)-2 and Rituximab in B-Cell Non-Hodgkin's Lymphoma: IL-2 Mediated Natural Killer Cell Expansion Correlations with Clinical Response," Clin Cancer Res 10:2253-2264 (2004).
Hatjiharissi, E., et al., "Individuals Expressing FcγRIIIA-158 V/V and V/F Show Increased NK Cell Surface Expression of FcgRIIIA (CD16), Rituximab Binding, and Demonstrate Higher Levels of ADCC Activity in Response to Rituximab," Blood 106:Abstract 776 (2005).
Khantasup, K., et al., "Design and Generation of Humanized Single-chain Fv Derived from Mouse Hybridoma for Potential Targeting Application," Monoclonal Antibodies in Immunodiagnosis and Immunotherapy 34(6):404-417 (2015).
Rudikoff, S., et al., "Single amino acid substitute altering antigen-binding specificity," Proc Natl Acad Sci 79:1979-1983 (1982).
Extended European Search Report in European Patent Application No. 15789676.2 dated Nov. 28, 2017.
Invitation to Respond to Written Opinion in Singaporean Patent Application No. 11201609014T dated Oct. 16, 2017.
Chinese Office Action in Chinese Patent Application No. 201480071111.X dated Oct. 16, 2017.
Final Office Action dated Oct. 16, 2017 in U.S. Appl. No. 14/441,551, Ohtomo, T., et al., filed May 8, 2015.
Japanese Office Action Appl. No. 2015-554492.
Thai Office Action dated Sep. 18, 2019 in Thai Application No. 0501003166.
Almagro, J. C. and Fransson, J., "Humanization of antibodies," Frontiers in Bioscience, 13:1619-1633 (2008).
Amit, A. G., et al., "Three-Dimensional Structure of an Antigen-Antibody Complex at 2.8 Å Resolution," Science, 233(4765):747-753 (1986).
Pre-Examination Written Opinion for Brazilian Application No. PI0506125-3 dated Oct. 16, 2018, 6 pages.
Pre-Examination Written Opinion for Brazilian Application No. PI0617412-4 dated Nov. 7, 2018, 6 pages.
Brown, M., et al., "Tolerance to Single, but Not Multiple, Amino Acid Replacements in Antibody $V_H$ CDR2," J Immunol, 156:3285-3291 (1996).
Capurro, M. I., et al., "Overexpression of Glypican-3 in human hepatocellular carcinomas determined by immunohistochemistry using a monoclonal antibody," Proceedings of the American Association for Cancer Research, 93$^{rd}$ Annual Meeting, Mar. 2002, 93:219, Abstract No. 1097.
Chen, M., et al., "Reevaluation of glypican-3 as a serological marker for hepatocellular carcinoma," Clinical Chimica Acta, 423:105-111 (2013).
Creative Diagnostics, Test and Assay Development, product page (2018).
Extended European Search Report for European Application No. 14874331.3 dated Feb. 7, 2019, 18 pages.
Partial Supplementary European Search Report for European Application No. 14874331.3 dated Nov. 7, 2018, 15 pages.
Extended European Search Report for European Application No. 16818042.0 dated Oct. 24, 2018, 12 pages.
Harlow, E. and Lane, D., Antibodies, A Laboratory Manual, Cold Spring Harbor Laboratory, 25-26 (1988).
Harlow, E. and Lane, D., Antibodies, A Laboratory Manual, Cold Spring Harbor Laboratory, 141-142 (1988).
Haruyama Y. et al., "High preoperative levels of serum glypican-3 containing N-terminal subunit are associated with poor prognosis in patients with hepatocellular carcinoma after partial hepatectomy," International Journal of Cancer, 137:1643-1651 (2015).
Hippo, Y., et al., "Identification of Soluble $NH_2$-Terminal Fragment of Glypican-3 as a Serological Marker for Early-Stage Hepatocellular Carcinoma," Cancer Research, 64:2418-2423 (2004).
Hearing Notice dated Jan. 29, 2018 in Indian Patent Application No. 2357/CHENP/2010.
Kim, M., et al., "Structure of the protein core of the glypican Dally-like and localization of a region important for hedgehog signaling," PNAS, 108(32):13112-13117 (2011).
Lei, J., et al., "Prediction of HLA-A2 restricted cytotoxic T lymphocyte epitope in high expression of tumor antigen glypican-3 in primary liver cancer," Jiefangjun Yiyao Zazhi, Journal, 25(8):26-28 (2013).
Li, S., et al., "Prokaryotic Expression of GPC3/MXR7 and Preparation of Anti-GPC3/MXR7 Antibody," China Journal of Modern Medicine 13(8):15-17 (2003), with English Abstract.
Nakano, K., et al., "Anti-glypican 3 antibodies cause ADCC against human hepatocellular carcinoma cells," Biochem Biophys Res Comm., 378:279-284 (2009).
Office Action for Australian Application No. 2013365430 dated Dec. 13, 2018, 8 pages.
Office Action for Brazilian Application No. PI0909672-8 dated Mar. 16, 2009, 7 pages.
Office Action for Chinese Application No. 201580024198.X dated Sep. 5, 2018, 19 pages.
Office Action for Chinese Application No. 201610183223.5 dated Jan. 9, 2019, 23 pages.
Office Action for Japanese Application No. 2015-554492 dated Jun. 30, 2018, 6 pages.
Office Action for Mexican Application No. MX/a/2015/007714 dated Sep. 26, 2018, 6 pages.
Office Action for Norwegian Application No. 20063539 dated Feb. 8, 2018, 9 pages.
Office Action for Russian Application No. 2015129697 dated Dec. 7, 2017, 12 pages.
Office Action for U.S. Appl. No. 14/713,416 dated Aug. 15, 2018, 16 pages.
Office Action for U.S. Appl. No. 15/107,316 dated May 4, 2018, 50 pages.
Office Action for U.S. Appl. No. 15/288,508 dated Jan. 9, 2018, 52 pages.
Office Action for U.S. Appl. No. 15/288,508 dated Sep. 21, 2018, 23 pages.
Pilia, G., et al., "Mutations in GPC3, a glypican gene, cause the Simpson-Golabi-Behmel overgrowth syndrome," Nature Genetics, 12:241-247 (1996).
Semenova, A. I., "Monitoring treatment efficacy and detecting relapses using biomarkers," Practical Oncology, 12(4):171-177 (2011), with English Abstract.
Sun, C., et al., "Suppression of Glypican 3 Inhibits Growth of Hepatocellular Carcinoma Cells through Up-Regulation of TGF-β2," Neoplasia 13(8):735-747 (2011).
Vajdos, F. F., "Comprehensive Functional Maps of the Antigen-binding Site of an Anti-ErbB2 Antibody Obtained with Shotgun Scanning Mutagenesis," J Mol Biol., 320(2):415-428 (2002).
Van Regenmortel, M. H. V., "Mapping Epitope Structure and Activity: From One-Dimensional Prediction to Four-Dimensional Description of Antigenic Specificity," Methods: A Companion to Methods in Enzymology 9(54):465-472 (1996).
Weisstein, E. W., "Combination," MathWorld—A Wolfram Web Resource (2018).
Yamauchi, N., et al., "The glypican 3 oncofetal protein is a promising disgnostic marker for hepatocellular carcinoma," Modern Pathology, 18:1591-1598 (2005).
Yorita, K., et al., "Prognostic significance of circumferential cell surface immunoreactivity of glypican-3 in hepatocellular carcinoma," Liver International 21(1):120-131 (2011).
Zhang, Q., et al., "Comparision of chemiluminescence enzyme immunoassay based on magnetic microparticles with traditional colorimetric ELISA for the detection of serum α-fetoprotein," Journal Pharmaceutical Analysis, 2(2):130-135 (2012).
Zynger, D. L., et al., "Glypican 3: A Novel Marker in Testicular Germ Cell Tumors," Am J Surg Pathol., 30:1570-1575 (2006).
Beano, A., et al., "Correlation between NK function and response to trastuzumab in metastatic breast cancer patients," J Transl Med., 6(25), 10 pages (2008).

(56) References Cited

OTHER PUBLICATIONS

Roca, L., et al., "Correlation of HER2, FCGR2A, and FCGR3A gene polymorphisms with trastuzumab related cardiac toxicity and efficacy in a subgroup of patients from UNICANCER-PACS04 trial," Breast Cancer Res Treat., 139:789-800 (2013).
Office Action for Brazilian Application No. PI0909672-8 dated April 18, 2018, 7 pages.
Office Action for Japanese Application No. 2015-554492 dated Jun. 19, 2018, 6 pages.
Ffrench, B., et al., "CTC-5: A Novel Digital Pathology Approach to Circulating Tumour Cell Characterisation," Journal of Pathology, 237(Supp 1):S20, Abstract (2015).
Final Office Action dated Mar. 4, 2021 in U.S. Appl. No. 15/741,219, filed Dec. 29, 2017, Ohtomo, et al.
Final Office Action dated Apr. 5, 2021 in U.S. Appl. No. 14/713,416, filed May 15, 2015, Nakano, et al.
Bikoue, A., et al., "Quantitative Analysis of Leukocyte Membrane Antigen Expression: Normal Adult Values," Cytometry (Communications in Clinical Cytometry), 26:137-147 (1996).
Communication pursuant to Article 94(3) EPC from the European Patent Office dated Oct. 9, 2020 in European Application No. 15789676.2, 6 pages.
Notice of Allowance from The Korean Intellectual Property Office dated Nov. 23, 2020 in Korean Application No. 10-2015-7013955, 4 pages.
Patent Examination Report 2 from the New Zealand Intellectual Property Office dated Jun. 25, 2020 in New Zealand Patent No. 707774, 10 pages.
Phung, Y., et al., "High-affinity monoclonal antibodies to cell surface tumor antigen glypican-3 generated through a combination of peptide immunization and flow cytometry screening," mAbs, 4(5):592-599 (2012).

\* cited by examiner

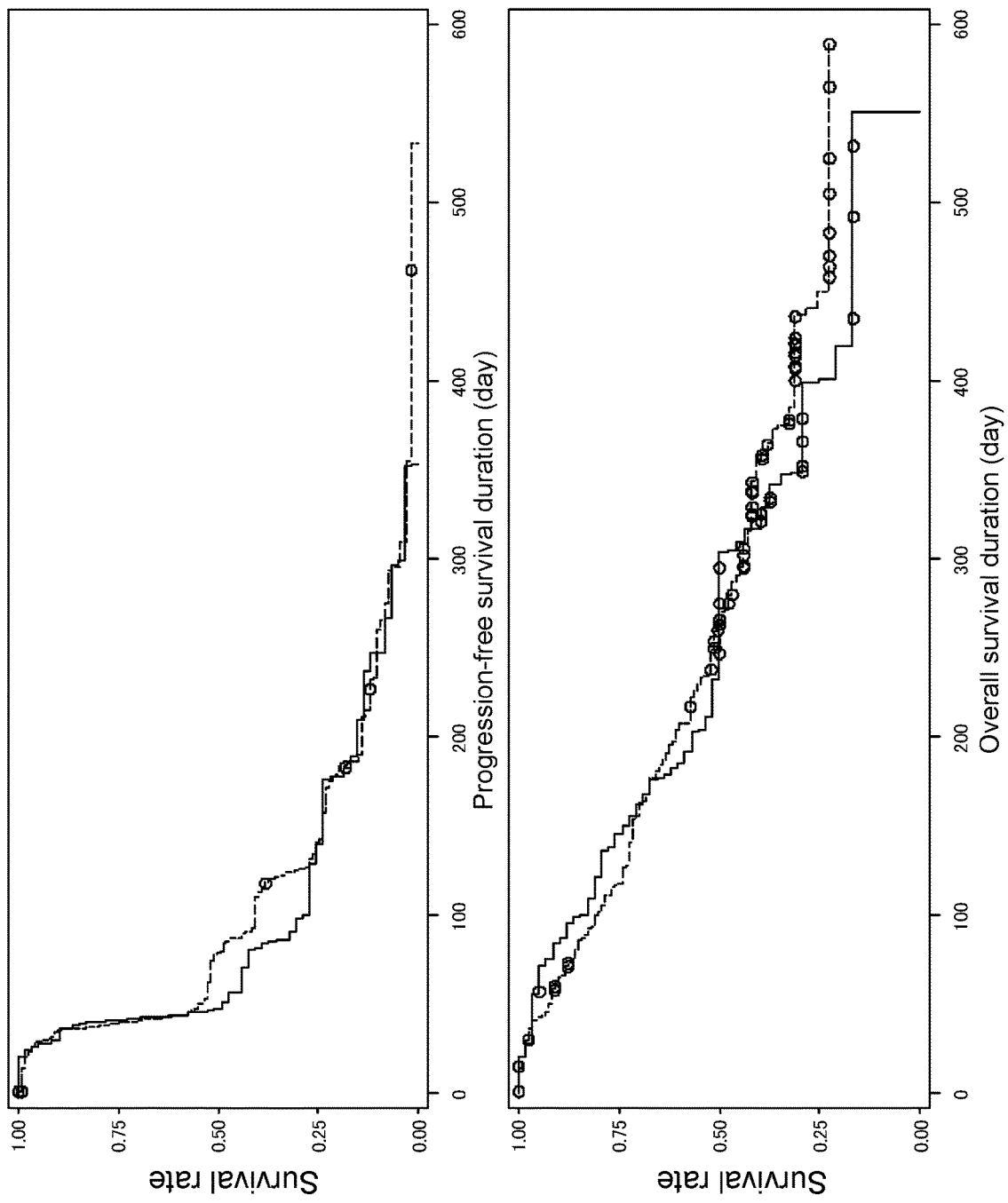
Figure 1  Kaplan-Meier curve (PFS and OS)

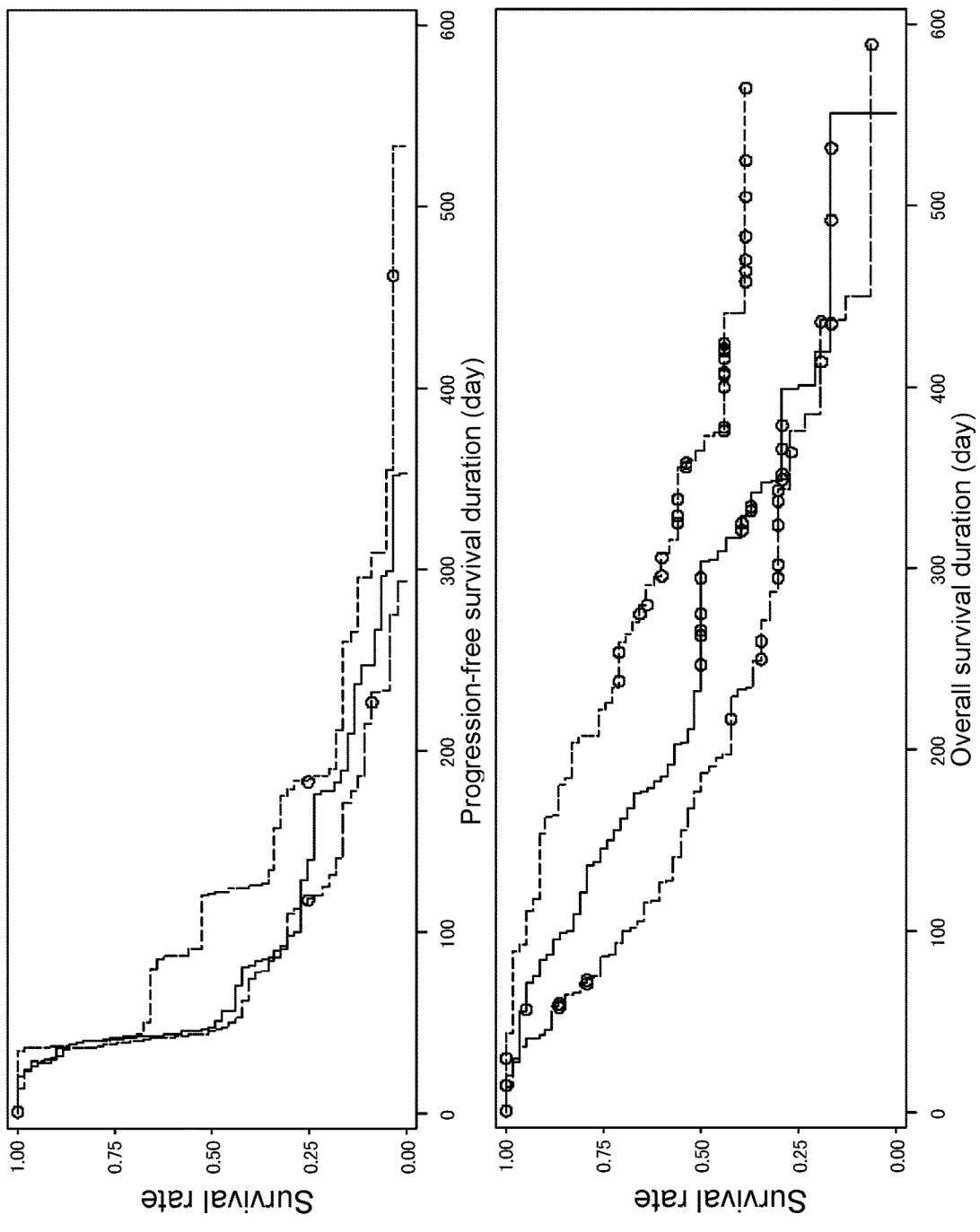
Figure 2 Kaplan-Meier curve (PFS and OS) from patients stratified depending on exposure to GC33

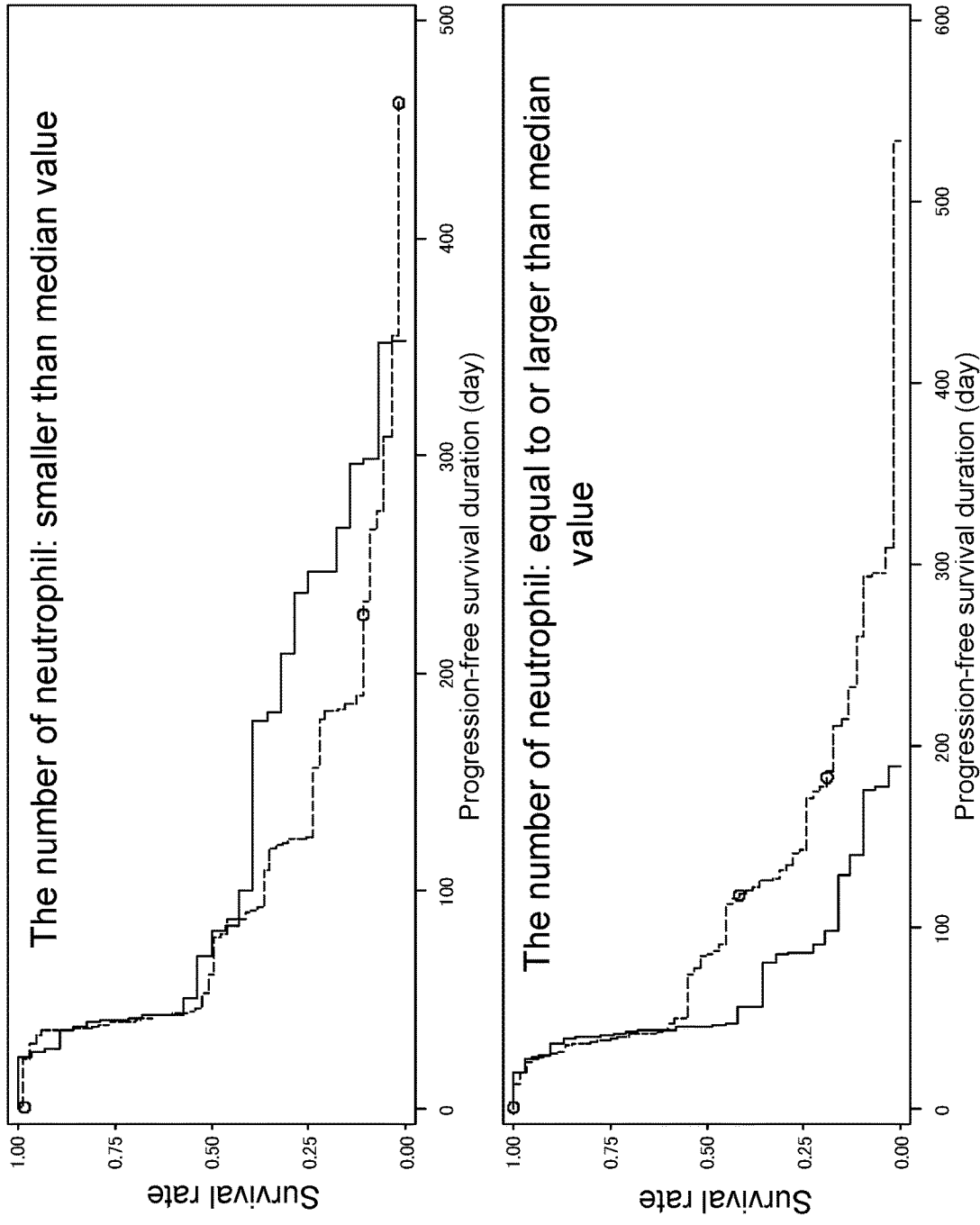
Figure 3 Kaplan-Meier curve (PFS) from patients stratified depending on the number of neutrophil in peripheral blood

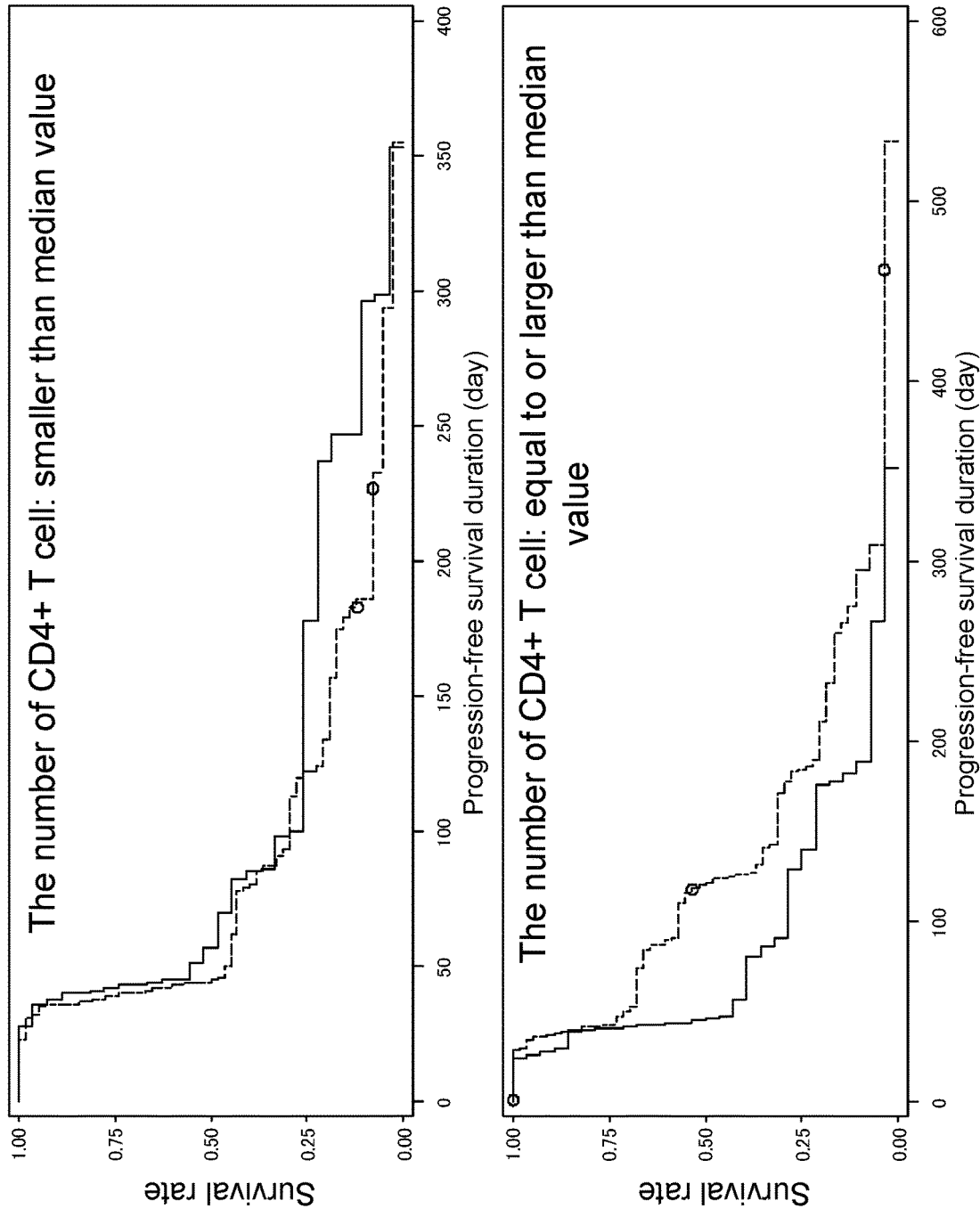
Figure 4  Kaplan-Meier curve (PFS) from patients stratified depending on the number of CD4+ T cell in peripheral blood

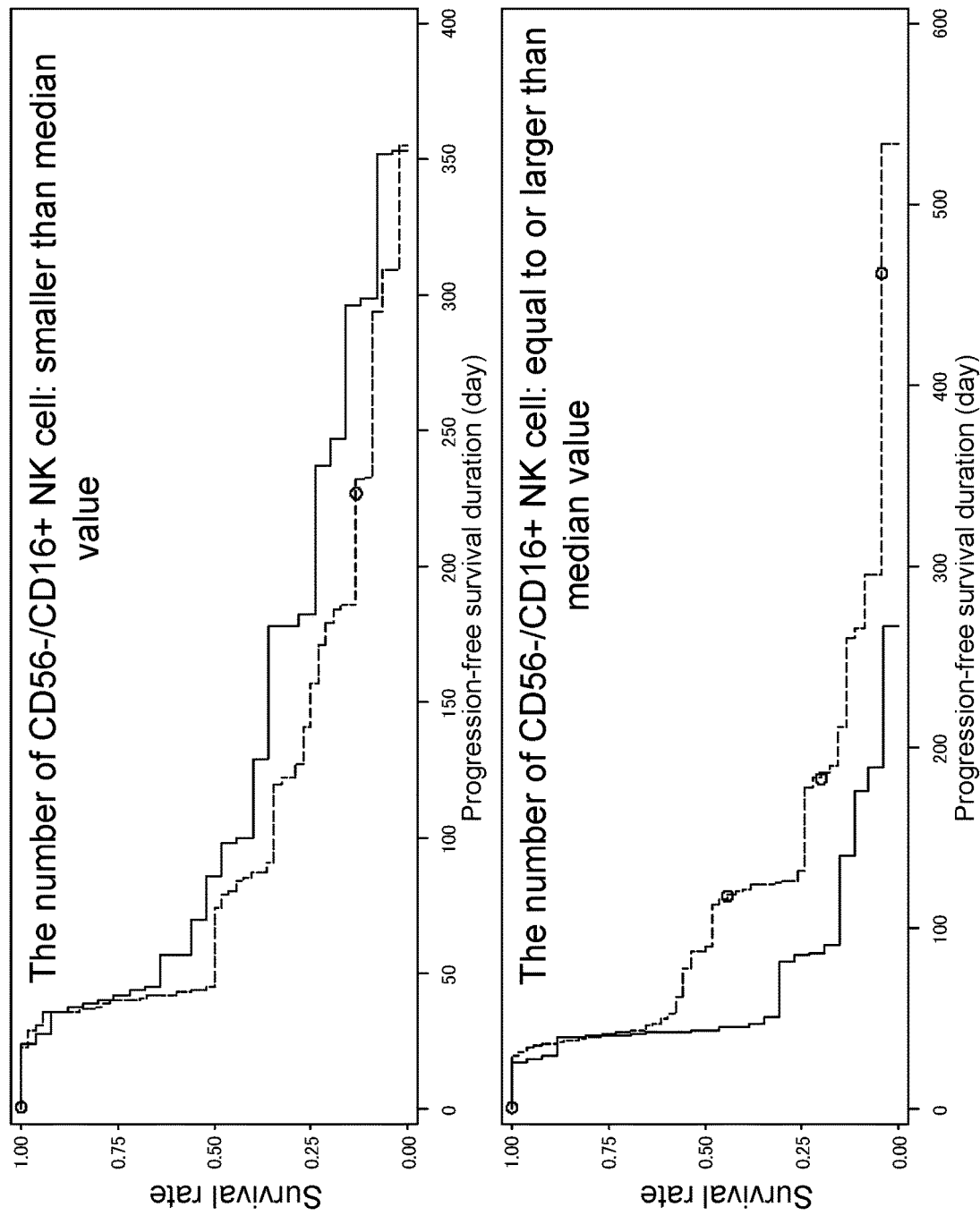
Figure 5  Kaplan-Meier curve (PFS) from patients stratified depending on the number of CD56-/CD16+ NK cell in peripheral blood

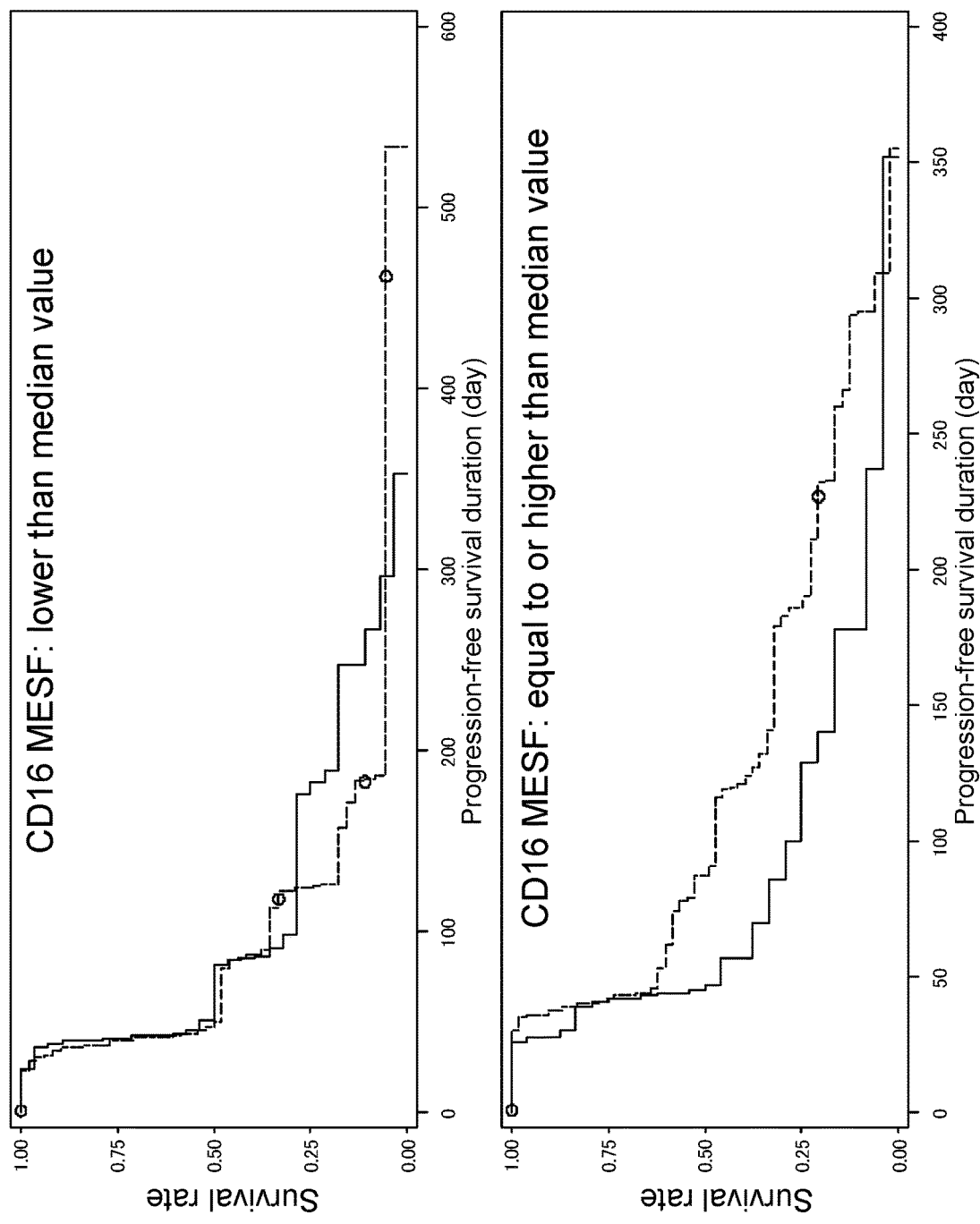
Figure 6  Kaplan-Meier curve (PFS) from patients stratified depending on expression level (MESF) of CD16 on NK cell in peripheral blood

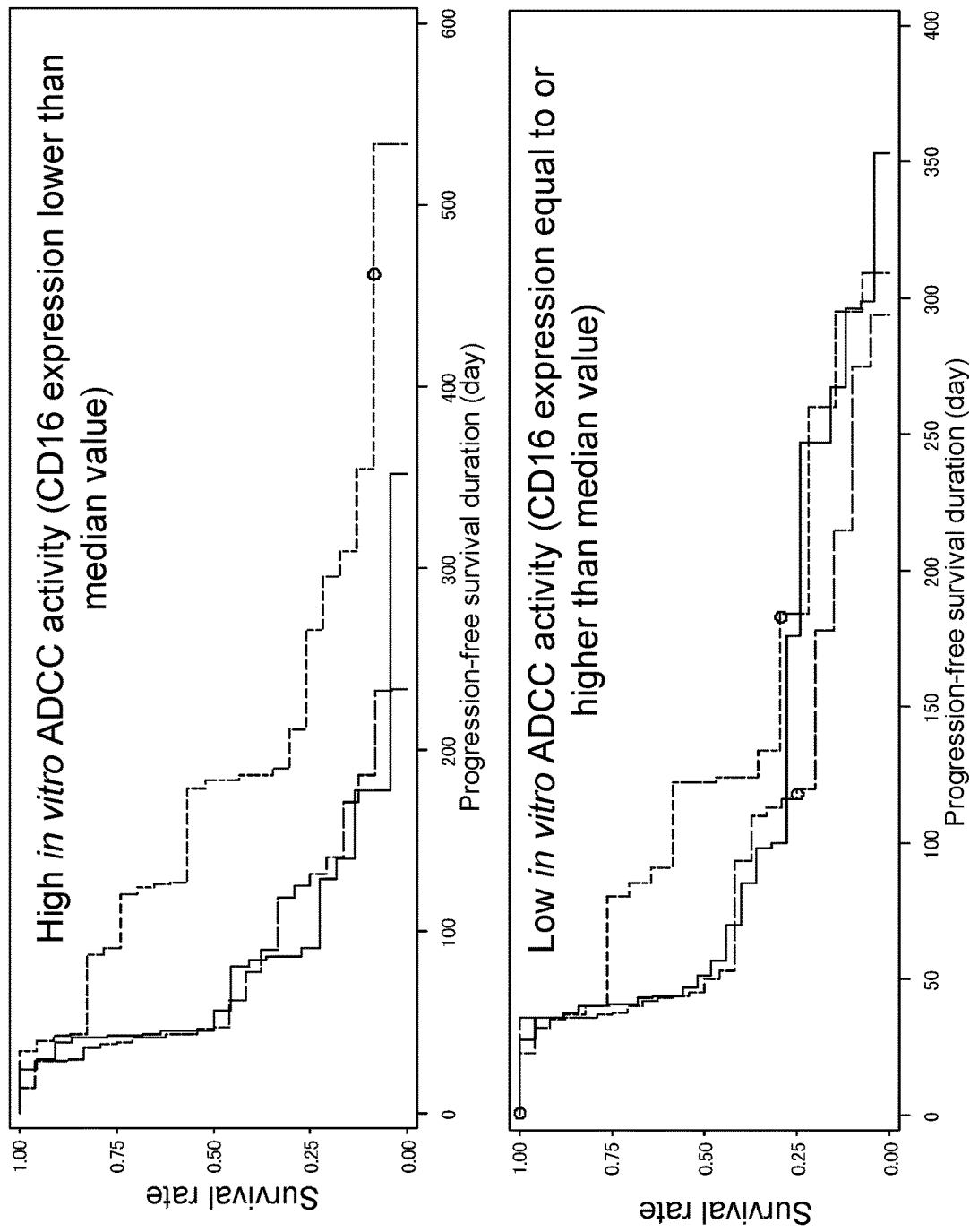
Figure 7 Kaplan-Meier curve (PFS) from patients stratified depending on baseline *in vitro* ADCC activity (CD16 expression)

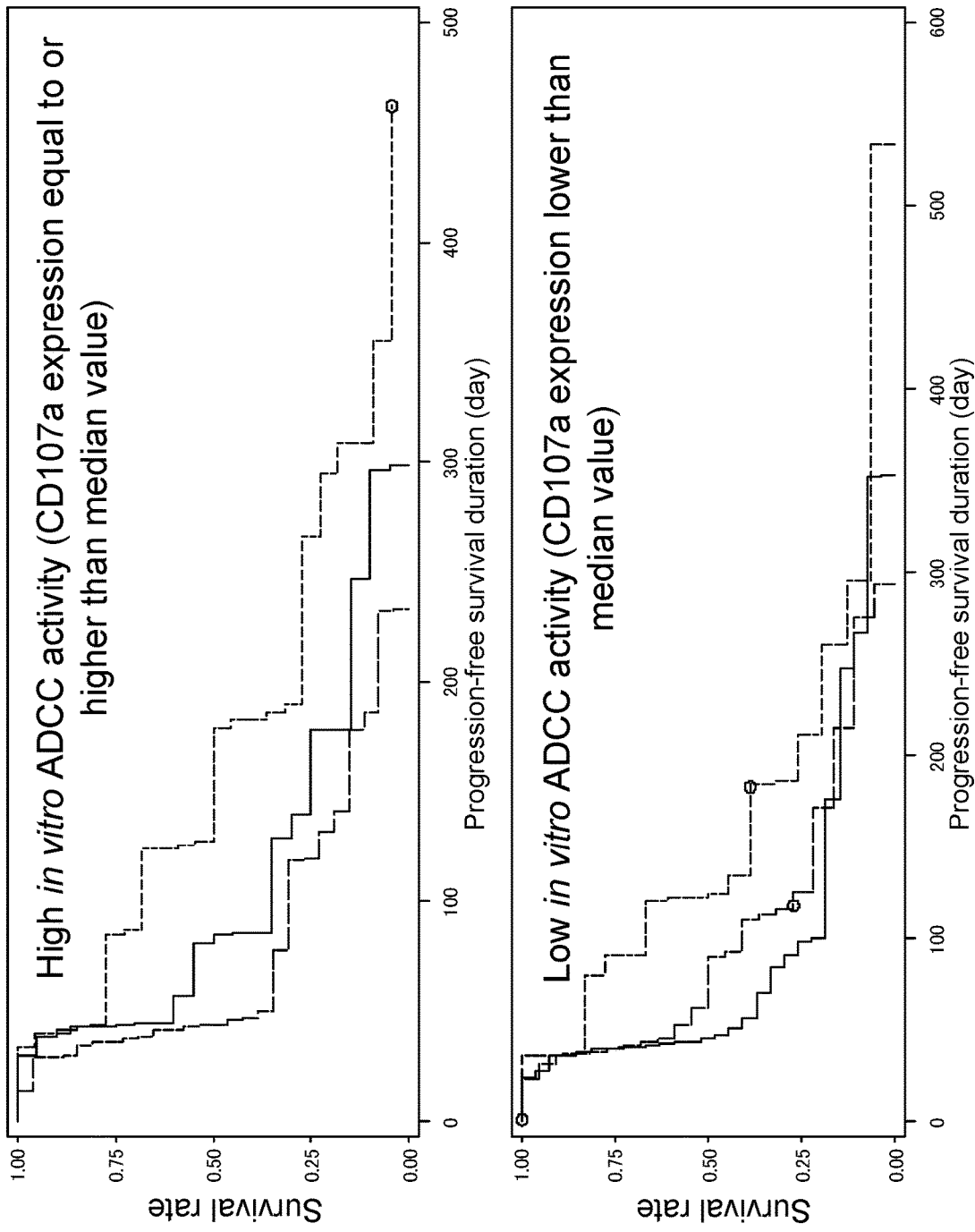
Figure 8 Kaplan-Meier curve (PFS) from patients stratified depending on baseline *in vitro* ADCC activity (CD107a expression)

SEQUENCE LISTING

<160> NUMBER OF SEQ ID NOS: 82

<210> SEQ ID NO 1
<211> LENGTH: 580
<212> TYPE: PRT
<213> ORGANISM: homo sapiens

<400> SEQUENCE: 1

Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Pro Asp
            20                  25                  30

Ala Thr Cys His Gln Val Arg Ser Phe Phe Gln Arg Leu Gln Pro Gly
                35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
        115                 120                 125

Met Phe Lys Asn Asn Tyr Pro Ser Leu Thr Pro Gln Ala Phe Glu Phe
    130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175

Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
        195                 200                 205

Gly Asn Phe Pro Lys Leu Ile Met Thr Gln Val Ser Lys Ser Leu Gln
    210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
                245                 250                 255

Thr Arg Met Trp Tyr Cys Ser Tyr Cys Gln Gly Leu Met Met Val Lys
            260                 265                 270

Pro Cys Gly Gly Tyr Cys Asn Val Val Met Gln Gly Cys Met Ala Gly
        275                 280                 285

Val Val Glu Ile Asp Lys Tyr Trp Arg Glu Tyr Ile Leu Ser Leu Glu
    290                 295                 300

Glu Leu Val Asn Gly Met Tyr Arg Ile Tyr Asp Met Glu Asn Val Leu
305                 310                 315                 320

Leu Gly Leu Phe Ser Thr Ile His Asp Ser Ile Gln Tyr Val Gln Lys
                325                 330                 335

Asn Ala Gly Lys Leu Thr Thr Thr Ile Gly Lys Leu Cys Ala His Ser
            340                 345                 350

Gln Gln Arg Gln Tyr Arg Ser Ala Tyr Tyr Pro Glu Asp Leu Phe Ile
        355                 360                 365

-continued

```
Asp Lys Lys Val Leu Lys Val Ala His Val Glu His Glu Thr Leu
    370                 375                 380
Ser Ser Arg Arg Arg Glu Leu Ile Gln Lys Leu Lys Ser Phe Ile Ser
385                 390                 395                 400
Phe Tyr Ser Ala Leu Pro Gly Tyr Ile Cys Ser His Ser Pro Val Ala
                405                 410                 415
Glu Asn Asp Thr Leu Cys Trp Asn Gly Gln Glu Leu Val Glu Arg Tyr
            420                 425                 430
Ser Gln Lys Ala Ala Arg Asn Gly Met Lys Asn Gln Phe Asn Leu His
        435                 440                 445
Glu Leu Lys Met Lys Gly Pro Glu Pro Val Val Ser Gln Ile Ile Asp
    450                 455                 460
Lys Leu Lys His Ile Asn Gln Leu Leu Arg Thr Met Ser Met Pro Lys
465                 470                 475                 480
Gly Arg Val Leu Asp Lys Asn Leu Asp Glu Glu Gly Phe Glu Ser Gly
                485                 490                 495
Asp Cys Gly Asp Glu Asp Glu Cys Ile Gly Gly Ser Gly Asp Gly
            500                 505                 510
Met Ile Lys Val Lys Asn Gln Leu Arg Phe Leu Ala Glu Leu Ala Tyr
    515                 520                 525
Asp Leu Asp Val Asp Asp Ala Pro Gly Asn Ser Gln Gln Ala Thr Pro
530                 535                 540
Lys Asp Asn Glu Ile Ser Thr Phe His Asn Leu Gly Asn Val His Ser
545                 550                 555                 560
Pro Leu Lys Leu Leu Thr Ser Met Ala Ile Ser Val Val Cys Phe Phe
                565                 570                 575
Phe Leu Val His
            580

<210> SEQ ID NO 2
<211> LENGTH: 9
<212> TYPE: PRT
<213> ORGANISM: homo sapiens

<400> SEQUENCE: 2

Phe Val Gly Glu Phe Phe Thr Asp Val
1               5

<210> SEQ ID NO 3
<211> LENGTH: 9
<212> TYPE: PRT
<213> ORGANISM: homo sapiens

<400> SEQUENCE: 3

Glu Tyr Ile Leu Ser Leu Glu Glu Leu
1               5

<210> SEQ ID NO 4
<211> LENGTH: 5
<212> TYPE: PRT
<213> ORGANISM: Mus musculus

<400> SEQUENCE: 4

Asp Tyr Ser Met His
1               5

<210> SEQ ID NO 5
<211> LENGTH: 17
<212> TYPE: PRT
```

<213> ORGANISM: Mus musculus

<400> SEQUENCE: 5

Trp Ile Asn Thr Glu Thr Gly Glu Pro Thr Tyr Ala Asp Asp Phe Lys
1               5                   10                  15

Gly

<210> SEQ ID NO 6
<211> LENGTH: 2
<212> TYPE: PRT
<213> ORGANISM: Mus musculus

<400> SEQUENCE: 6

Leu Tyr
1

<210> SEQ ID NO 7
<211> LENGTH: 16
<212> TYPE: PRT
<213> ORGANISM: Mus musculus

<400> SEQUENCE: 7

Lys Ser Ser Gln Ser Leu Leu His Ser Asp Gly Lys Thr Phe Leu Asn
1               5                   10                  15

<210> SEQ ID NO 8
<211> LENGTH: 7
<212> TYPE: PRT
<213> ORGANISM: Mus musculus

<400> SEQUENCE: 8

Leu Val Ser Arg Leu Asp Ser
1               5

<210> SEQ ID NO 9
<211> LENGTH: 9
<212> TYPE: PRT
<213> ORGANISM: Mus musculus

<400> SEQUENCE: 9

Cys Gln Gly Thr His Phe Pro Arg Thr
1               5

<210> SEQ ID NO 10
<211> LENGTH: 111
<212> TYPE: PRT
<213> ORGANISM: Mus musculus

<400> SEQUENCE: 10

Gln Ile Gln Leu Glu Gln Ser Gly Pro Glu Leu Lys Lys Pro Gly Glu
1               5                   10                  15

Thr Val Lys Ile Ser Cys Lys Ala Ser Gly Tyr Ile Phe Arg Asp Tyr
                20                  25                  30

Ser Met His Trp Val Lys Gln Ala Pro Gly Lys Gly Leu Lys Trp Met
            35                  40                  45

Gly Trp Ile Asn Thr Glu Thr Gly Glu Pro Thr Tyr Ala Asp Asp Phe
        50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

```
Thr Ser Leu Tyr Trp Gly Gln Gly Thr Leu Val Thr Val Ser Ala
            100                 105                 110
```

<210> SEQ ID NO 11
<211> LENGTH: 112
<212> TYPE: PRT
<213> ORGANISM: Mus musculus

<400> SEQUENCE: 11

```
Asp Val Val Met Thr Gln Thr Pro Leu Thr Leu Ser Val Thr Leu Gly
1               5                   10                  15

Gln Pro Ala Ser Ile Ser Cys Lys Ser Ser Gln Ser Leu Leu His Ser
            20                  25                  30

Asp Gly Lys Thr Phe Leu Asn Trp Leu Leu Gln Arg Pro Gly Gln Ser
        35                  40                  45

Pro Lys Arg Leu Ile Tyr Leu Val Ser Arg Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Cys Gln Gly
                85                  90                  95

Thr His Phe Pro Arg Thr Phe Gly Gly Thr Arg Leu Glu Ile Lys
            100                 105                 110
```

<210> SEQ ID NO 12
<211> LENGTH: 7
<212> TYPE: PRT
<213> ORGANISM: Mus musculus

<400> SEQUENCE: 12

```
Thr Tyr Gly Met Gly Val Gly
1               5
```

<210> SEQ ID NO 13
<211> LENGTH: 16
<212> TYPE: PRT
<213> ORGANISM: Mus musculus

<400> SEQUENCE: 13

```
Asn Ile Trp Trp His Asp Asp Lys Tyr Tyr Asn Ser Ala Leu Lys Ser
1               5                   10                  15
```

<210> SEQ ID NO 14
<211> LENGTH: 14
<212> TYPE: PRT
<213> ORGANISM: Mus musculus

<400> SEQUENCE: 14

```
Ile Ala Pro Arg Tyr Asn Lys Tyr Glu Gly Phe Phe Ala Phe
1               5                   10
```

<210> SEQ ID NO 15
<211> LENGTH: 16
<212> TYPE: PRT
<213> ORGANISM: Mus musculus

<400> SEQUENCE: 15

```
Arg Ser Ser Gln Ser Ile Val His Ser Asn Gly Asn Thr Tyr Leu Glu
1               5                   10                  15
```

<210> SEQ ID NO 16
<211> LENGTH: 7

```
<212> TYPE: PRT
<213> ORGANISM: Mus musculus

<400> SEQUENCE: 16

Lys Val Ser Asn Arg Phe Ser
1               5

<210> SEQ ID NO 17
<211> LENGTH: 9
<212> TYPE: PRT
<213> ORGANISM: Mus musculus

<400> SEQUENCE: 17

Phe Gln Gly Ser His Val Pro Trp Thr
1               5

<210> SEQ ID NO 18
<211> LENGTH: 124
<212> TYPE: PRT
<213> ORGANISM: Mus musculus

<400> SEQUENCE: 18

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Gly Trp Ile Arg Gln Pro Ser Gly Lys Gly Leu Glu
        35                  40                  45

Trp Leu Ala Asn Ile Trp Trp His Asp Asp Lys Tyr Tyr Asn Ser Ala
    50                  55                  60

Leu Lys Ser Arg Leu Thr Ile Ser Lys Asp Ile Ser Asn Asn Gln Val
65                  70                  75                  80

Phe Leu Lys Ile Ser Ser Val Asp Thr Ala Asp Thr Ala Thr Tyr Tyr
                85                  90                  95

Cys Ala Gln Ile Ala Pro Arg Tyr Asn Lys Tyr Glu Gly Phe Phe Ala
            100                 105                 110

Phe Trp Gly Gln Gly Thr Leu Val Thr Val Ser Ala
        115                 120

<210> SEQ ID NO 19
<211> LENGTH: 112
<212> TYPE: PRT
<213> ORGANISM: Mus musculus

<400> SEQUENCE: 19

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110
```

<210> SEQ ID NO 20
<211> LENGTH: 5
<212> TYPE: PRT
<213> ORGANISM: Mus musculus

<400> SEQUENCE: 20

Asp Tyr Glu Met His
1               5

<210> SEQ ID NO 21
<211> LENGTH: 17
<212> TYPE: PRT
<213> ORGANISM: Mus musculus

<400> SEQUENCE: 21

Ala Leu Asp Pro Lys Thr Gly Asp Thr Ala Tyr Ser Gln Lys Phe Lys
1               5                   10                  15

Gly

<210> SEQ ID NO 22
<211> LENGTH: 6
<212> TYPE: PRT
<213> ORGANISM: Mus musculus

<400> SEQUENCE: 22

Phe Tyr Ser Tyr Thr Tyr
1               5

<210> SEQ ID NO 23
<211> LENGTH: 16
<212> TYPE: PRT
<213> ORGANISM: Mus musculus

<400> SEQUENCE: 23

Arg Ser Ser Gln Ser Leu Val His Ser Asn Gly Asn Thr Tyr Leu His
1               5                   10                  15

<210> SEQ ID NO 24
<211> LENGTH: 7
<212> TYPE: PRT
<213> ORGANISM: Mus musculus

<400> SEQUENCE: 24

Lys Val Ser Asn Arg Phe Ser
1               5

<210> SEQ ID NO 25
<211> LENGTH: 9
<212> TYPE: PRT
<213> ORGANISM: Mus musculus

<400> SEQUENCE: 25

Ser Gln Asn Thr His Val Pro Pro Thr
1               5

<210> SEQ ID NO 26
<211> LENGTH: 115
<212> TYPE: PRT
<213> ORGANISM: Mus musculus

<400> SEQUENCE: 26

Gln Val Gln Leu Gln Gln Ser Gly Ala Glu Leu Val Arg Pro Gly Ala
1               5                   10                  15

Ser Val Lys Leu Ser Cys Lys Ala Ser Gly Tyr Thr Phe Thr Asp Tyr
    20                  25                  30

Glu Met His Trp Val Lys Gln Thr Pro Val His Gly Leu Lys Trp Ile
        35                  40                  45

Gly Ala Leu Asp Pro Lys Thr Gly Asp Thr Ala Tyr Ser Gln Lys Phe
 50                  55                  60

Lys Gly Lys Ala Thr Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
            85                  90                  95

Thr Arg Phe Tyr Ser Tyr Thr Tyr Trp Gly Gln Gly Thr Leu Val Thr
            100                 105                 110

Val Ser Ala
    115

<210> SEQ ID NO 27
<211> LENGTH: 112
<212> TYPE: PRT
<213> ORGANISM: Mus musculus

<400> SEQUENCE: 27

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Pro Thr Phe Gly Ser Gly Thr Lys Leu Glu Ile Lys
            100                 105                 110

<210> SEQ ID NO 28
<211> LENGTH: 5
<212> TYPE: PRT
<213> ORGANISM: Mus musculus

<400> SEQUENCE: 28

Ile Asn Ala Met Asn
1               5

<210> SEQ ID NO 29
<211> LENGTH: 19
<212> TYPE: PRT
<213> ORGANISM: Mus musculus

<400> SEQUENCE: 29

Arg Ile Arg Ser Glu Ser Asn Asn Tyr Ala Thr Tyr Tyr Gly Asp Ser
1               5                   10                  15

Val Lys Asp

<210> SEQ ID NO 30
<211> LENGTH: 8
<212> TYPE: PRT

<213> ORGANISM: Mus musculus

<400> SEQUENCE: 30

Glu Val Thr Thr Ser Phe Ala Tyr
1               5

<210> SEQ ID NO 31
<211> LENGTH: 16
<212> TYPE: PRT
<213> ORGANISM: Mus musculus

<400> SEQUENCE: 31

Lys Ser Ser Lys Ser Leu Leu His Ser Asn Gly Asn Thr Tyr Leu Asn
1               5                   10                  15

<210> SEQ ID NO 32
<211> LENGTH: 7
<212> TYPE: PRT
<213> ORGANISM: Mus musculus

<400> SEQUENCE: 32

Trp Met Ser Asn Leu Ala Ser
1               5

<210> SEQ ID NO 33
<211> LENGTH: 9
<212> TYPE: PRT
<213> ORGANISM: Mus musculus

<400> SEQUENCE: 33

Met Gln His Ile Glu Tyr Pro Phe Thr
1               5

<210> SEQ ID NO 34
<211> LENGTH: 119
<212> TYPE: PRT
<213> ORGANISM: Mus musculus

<400> SEQUENCE: 34

Glu Val Gln Leu Val Glu Thr Gly Gly Gly Leu Val Gln Pro Glu Gly
1               5                   10                  15

Ser Leu Lys Leu Ser Cys Ala Ala Ser Gly Phe Ser Phe Asn Ile Asn
                20                  25                  30

Ala Met Asn Trp Val Arg Gln Ala Pro Gly Lys Gly Leu Glu Trp Val
            35                  40                  45

Ala Arg Ile Arg Ser Glu Ser Asn Asn Tyr Ala Thr Tyr Tyr Gly Asp
        50                  55                  60

Ser Val Lys Asp Arg Phe Thr Ile Ser Arg Asp Asp Ser Gln Asn Met
65                  70                  75                  80

Leu Tyr Leu Gln Met Asn Asn Leu Lys Thr Glu Asp Thr Ala Ile Tyr
                85                  90                  95

Tyr Cys Val Arg Glu Val Thr Thr Ser Phe Ala Tyr Trp Gly Gln Gly
            100                 105                 110

Thr Leu Val Thr Val Ser Ala
        115

<210> SEQ ID NO 35
<211> LENGTH: 112
<212> TYPE: PRT
<213> ORGANISM: Mus musculus

<400> SEQUENCE: 35

```
Asp Ile Val Met Thr Gln Ser Ala Pro Ser Val Pro Val Thr Pro Gly
1               5                   10                  15

Glu Ser Val Ser Ile Ser Cys Lys Ser Ser Lys Ser Leu Leu His Ser
            20                  25                  30

Asn Gly Asn Thr Tyr Leu Asn Trp Phe Leu Gln Arg Pro Gly Gln Ser
        35                  40                  45

Pro Gln Leu Leu Ile Tyr Trp Met Ser Asn Leu Ala Ser Gly Val Pro
    50                  55                  60

Asp Arg Phe Ser Gly Ser Gly Ser Gly Thr Ala Phe Thr Leu Arg Ile
65              70                  75                  80

Ser Arg Val Glu Ala Glu Asp Val Gly Val Tyr Tyr Cys Met Gln His
                85                  90                  95

Ile Glu Tyr Pro Phe Thr Phe Gly Thr Gly Thr Lys Leu Glu Ile Lys
                100                 105                 110
```

<210> SEQ ID NO 36
<211> LENGTH: 5
<212> TYPE: PRT
<213> ORGANISM: Mus musculus

<400> SEQUENCE: 36

```
Ala Ser Ala Met Asn
1               5
```

<210> SEQ ID NO 37
<211> LENGTH: 19
<212> TYPE: PRT
<213> ORGANISM: Mus musculus

<400> SEQUENCE: 37

```
Arg Ile Arg Ser Lys Ser Asn Asn Tyr Ala Ile Tyr Tyr Ala Asp Ser
1               5                   10                  15

Val Lys Asp
```

<210> SEQ ID NO 38
<211> LENGTH: 12
<212> TYPE: PRT
<213> ORGANISM: Mus musculus

<400> SEQUENCE: 38

```
Asp Pro Gly Tyr Tyr Gly Asn Pro Trp Phe Ala Tyr
1               5                   10
```

<210> SEQ ID NO 39
<211> LENGTH: 16
<212> TYPE: PRT
<213> ORGANISM: Mus musculus

<400> SEQUENCE: 39

```
Arg Ser Ser Lys Ser Leu Leu His Ser Tyr Asp Ile Thr Tyr Leu Tyr
1               5                   10                  15
```

<210> SEQ ID NO 40
<211> LENGTH: 7
<212> TYPE: PRT
<213> ORGANISM: Mus musculus

<400> SEQUENCE: 40

```
Gln Met Ser Asn Leu Ala Ser
1               5
```

<210> SEQ ID NO 41
<211> LENGTH: 9
<212> TYPE: PRT
<213> ORGANISM: Mus musculus

<400> SEQUENCE: 41

Ala Gln Asn Leu Glu Leu Pro Pro Thr
1               5

<210> SEQ ID NO 42
<211> LENGTH: 123
<212> TYPE: PRT
<213> ORGANISM: Mus musculus

<400> SEQUENCE: 42

Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Ala Ser
                20                  25                  30

Ala Met Asn Trp Val Arg Gln Ala Pro Gly Lys Gly Leu Glu Trp Val
            35                  40                  45

Ala Arg Ile Arg Ser Lys Ser Asn Asn Tyr Ala Ile Tyr Tyr Ala Asp
        50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Asp Pro Gly Tyr Tyr Gly Asn Pro Trp Phe Ala Tyr
            100                 105                 110

Trp Gly Gln Gly Thr Leu Val Thr Val Ser Ala
        115                 120

<210> SEQ ID NO 43
<211> LENGTH: 112
<212> TYPE: PRT
<213> ORGANISM: Mus musculus

<400> SEQUENCE: 43

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
                20                  25                  30

Tyr Asp Ile Thr Tyr Leu Tyr Trp Tyr Leu Gln Lys Pro Gly Gln Ser
            35                  40                  45

Pro Gln Leu Leu Ile Tyr Gln Met Ser Asn Leu Ala Ser Gly Val Pro
        50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Pro Thr Phe Gly Gly Gly Thr Lys Leu Glu Ile Lys
            100                 105                 110

<210> SEQ ID NO 44
<211> LENGTH: 115
<212> TYPE: PRT
<213> ORGANISM: Artificial Sequence
<220> FEATURE:
<223> OTHER INFORMATION: modified antibody fragment

<400> SEQUENCE: 44

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
        50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Tyr Ser Tyr Thr Tyr Trp Gly Gln Gly Thr Leu Val Thr
            100                 105                 110

Val Ser Ser
        115

<210> SEQ ID NO 45
<211> LENGTH: 115
<212> TYPE: PRT
<213> ORGANISM: Artificial Sequence
<220> FEATURE:
<223> OTHER INFORMATION: modified antibody fragment

<400> SEQUENCE: 45

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
        50                  55                  60

Lys Gly Arg Val Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 46
<211> LENGTH: 115
<212> TYPE: PRT
<213> ORGANISM: Artificial Sequence
<220> FEATURE:
<223> OTHER INFORMATION: modified antibody fragment

<400> SEQUENCE: 46

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
            50                  55                  60

Lys Gly Arg Val Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                    85                  90                  95

Thr Arg Phe Tyr Ser Tyr Thr Tyr Trp Gly Gln Gly Thr Leu Val Thr
                100                 105                 110

Val Ser Ser
        115

<210> SEQ ID NO 47
<211> LENGTH: 115
<212> TYPE: PRT
<213> ORGANISM: Artificial Sequence
<220> FEATURE:
<223> OTHER INFORMATION: modified antibody fragment

<400> SEQUENCE: 47

Gln Val Gln Leu Val Glu Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
            50                  55                  60

Lys Gly Arg Val Thr Leu Thr Ala Asp Lys Ser Thr Ser Thr Ala Tyr
 65                  70                  75                  80

Met Glu Leu Ser Ser Leu Thr Ser Glu Asp Thr Ala Val Tyr Tyr Cys
                    85                  90                  95

Thr Arg Phe Tyr Ser Tyr Thr Tyr Trp Gly Gln Gly Thr Leu Val Thr
                100                 105                 110

Val Ser Ser
        115

<210> SEQ ID NO 48
<211> LENGTH: 115
<212> TYPE: PRT
<213> ORGANISM: Artificial Sequence
<220> FEATURE:
<223> OTHER INFORMATION: modified antibody fragment

<400> SEQUENCE: 48

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
            50                  55                  60

Lys Gly Arg Val Thr Leu Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                    85                  90                  95

Thr Arg Phe Tyr Ser Tyr Thr Tyr Trp Gly Gln Gly Thr Leu Val Thr

Val Ser Ser
    115

<210> SEQ ID NO 49
<211> LENGTH: 115
<212> TYPE: PRT
<213> ORGANISM: Artificial Sequence
<220> FEATURE:
<223> OTHER INFORMATION: modified antibody fragment

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
    115

<210> SEQ ID NO 50
<211> LENGTH: 115
<212> TYPE: PRT
<213> ORGANISM: Artificial Sequence
<220> FEATURE:
<223> OTHER INFORMATION: modified antibody fragment

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
    115

<210> SEQ ID NO 51
<211> LENGTH: 112
<212> TYPE: PRT
<213> ORGANISM: Artificial Sequence
<220> FEATURE:

<223> OTHER INFORMATION: modified antibody fragment

<400> SEQUENCE: 51

```
Asp Val Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Val His Ser
            20                  25                  30
Asn Gly Asn Thr Tyr Leu His Trp Tyr Leu Gln Lys Pro Gly Gln Ser
        35                  40                  45
Pro Gln Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Ser Gln Asn
                85                  90                  95
Thr His Val Pro Pro Thr Phe Gly Gln Gly Thr Lys Leu Glu Ile Lys
            100                 105                 110
```

<210> SEQ ID NO 52
<211> LENGTH: 112
<212> TYPE: PRT
<213> ORGANISM: Artificial Sequence
<220> FEATURE:
<223> OTHER INFORMATION: modified antibody fragment

<400> SEQUENCE: 52

```
Asp Val Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Val His Ser
            20                  25                  30
Asn Ala Asn Thr Tyr Leu His Trp Tyr Leu Gln Lys Pro Gly Gln Ser
        35                  40                  45
Pro Gln Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Ser Gln Asn
                85                  90                  95
Thr His Val Pro Pro Thr Phe Gly Gln Gly Thr Lys Leu Glu Ile Lys
            100                 105                 110
```

<210> SEQ ID NO 53
<211> LENGTH: 112
<212> TYPE: PRT
<213> ORGANISM: Artificial Sequence
<220> FEATURE:
<223> OTHER INFORMATION: modified antibody fragment

<400> SEQUENCE: 53

```
Asp Val Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Val His Ser
            20                  25                  30
Asn Asp Asn Thr Tyr Leu His Trp Tyr Leu Gln Lys Pro Gly Gln Ser
        35                  40                  45
Pro Gln Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
```

```
                65                  70                  75                  80
Ser Arg Val Glu Ala Glu Asp Val Gly Val Tyr Tyr Cys Ser Gln Asn
                    85                  90                  95

Thr His Val Pro Pro Thr Phe Gly Gln Gly Thr Lys Leu Glu Ile Lys
                100                 105                 110

<210> SEQ ID NO 54
<211> LENGTH: 112
<212> TYPE: PRT
<213> ORGANISM: Artificial Sequence
<220> FEATURE:
<223> OTHER INFORMATION: modified antibody fragment

<400> SEQUENCE: 54

Asp Val Val Met Thr Gln Ser Pro Leu Ser Leu Pro Val Thr Pro Gly
1               5                   10                  15

Glu Pro Ala Ser Ile Ser Cys Arg Ser Gln Ser Leu Val His Ser
                20                  25                  30

Asn Glu Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                    85                  90                  95

Thr His Val Pro Pro Thr Phe Gly Gln Gly Thr Lys Leu Glu Ile Lys
                100                 105                 110

<210> SEQ ID NO 55
<211> LENGTH: 112
<212> TYPE: PRT
<213> ORGANISM: Artificial Sequence
<220> FEATURE:
<223> OTHER INFORMATION: modified antibody fragment

<400> SEQUENCE: 55

Asp Val Val Met Thr Gln Ser Pro Leu Ser Leu Pro Val Thr Pro Gly
1               5                   10                  15

Glu Pro Ala Ser Ile Ser Cys Arg Ser Gln Ser Leu Val His Ser
                20                  25                  30

Asn Phe Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                    85                  90                  95

Thr His Val Pro Pro Thr Phe Gly Gln Gly Thr Lys Leu Glu Ile Lys
                100                 105                 110

<210> SEQ ID NO 56
<211> LENGTH: 112
<212> TYPE: PRT
<213> ORGANISM: Artificial Sequence
<220> FEATURE:
<223> OTHER INFORMATION: modified antibody fragment

<400> SEQUENCE: 56
```

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn His Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 57
<211> LENGTH: 112
<212> TYPE: PRT
<213> ORGANISM: Artificial Sequence
<220> FEATURE:
<223> OTHER INFORMATION: modified antibody fragment

<400> SEQUENCE: 57

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Asn Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 58
<211> LENGTH: 112
<212> TYPE: PRT
<213> ORGANISM: Artificial Sequence
<220> FEATURE:
<223> OTHER INFORMATION: modified antibody fragment

<400> SEQUENCE: 58

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Thr Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn

```
            85                  90                  95

Thr His Val Pro Pro Thr Phe Gly Gln Gly Thr Lys Leu Glu Ile Lys
            100                 105                 110

<210> SEQ ID NO 59
<211> LENGTH: 112
<212> TYPE: PRT
<213> ORGANISM: Artificial Sequence
<220> FEATURE:
<223> OTHER INFORMATION: modified antibody fragment

<400> SEQUENCE: 59

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gln Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 60
<211> LENGTH: 112
<212> TYPE: PRT
<213> ORGANISM: Artificial Sequence
<220> FEATURE:
<223> OTHER INFORMATION: modified antibody fragment

<400> SEQUENCE: 60

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ile Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 61
<211> LENGTH: 112
<212> TYPE: PRT
<213> ORGANISM: Artificial Sequence
<220> FEATURE:
<223> OTHER INFORMATION: modified antibody fragment

<400> SEQUENCE: 61

Asp Val Val Met Thr Gln Ser Pro Leu Ser Leu Pro Val Thr Pro Gly
1               5                   10                  15
```

Glu Pro Ala Ser Ile Ser Cys Arg Ser Ser Gln Ser Leu Val His Ser
            20                  25                  30

Asn Lys Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 62
<211> LENGTH: 112
<212> TYPE: PRT
<213> ORGANISM: Artificial Sequence
<220> FEATURE:
<223> OTHER INFORMATION: modified antibody fragment

<400> SEQUENCE: 62

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Leu Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 63
<211> LENGTH: 112
<212> TYPE: PRT
<213> ORGANISM: Artificial Sequence
<220> FEATURE:
<223> OTHER INFORMATION: modified antibody fragment

<400> SEQUENCE: 63

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ser Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys

<210> SEQ ID NO 64
<211> LENGTH: 112
<212> TYPE: PRT
<213> ORGANISM: Artificial Sequence
<220> FEATURE:
<223> OTHER INFORMATION: modified antibody fragment

<400> SEQUENCE: 64

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Trp Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 65
<211> LENGTH: 112
<212> TYPE: PRT
<213> ORGANISM: Artificial Sequence
<220> FEATURE:
<223> OTHER INFORMATION: modified antibody fragment

<400> SEQUENCE: 65

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Tyr Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 66
<211> LENGTH: 112
<212> TYPE: PRT
<213> ORGANISM: Artificial Sequence
<220> FEATURE:
<223> OTHER INFORMATION: modified antibody fragment

<400> SEQUENCE: 66

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

```
Asn Arg Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
                100                 105                 110

<210> SEQ ID NO 67
<211> LENGTH: 115
<212> TYPE: PRT
<213> ORGANISM: Artificial Sequence
<220> FEATURE:
<223> OTHER INFORMATION: modified antibody fragment

<400> SEQUENCE: 67

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Glu Met His Trp Ile Arg Gln Pro Pro Gly Lys Gly Leu Glu Trp Ile
            35                  40                  45

Gly Ala Ile Asn Pro Lys Thr Gly Asp Thr Ala Tyr Ser Gln Lys Phe
 50                  55                  60

Lys Gly Arg Val Thr Leu Thr Ala Asp Lys Ser Thr Ser Thr Ala Tyr
 65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Arg Gly Thr Leu Val Thr
                100                 105                 110

Val Ser Ser
        115

<210> SEQ ID NO 68
<211> LENGTH: 112
<212> TYPE: PRT
<213> ORGANISM: Artificial Sequence
<220> FEATURE:
<223> OTHER INFORMATION: modified antibody fragment

<400> SEQUENCE: 68

Asp Ile Val Met Thr Gln Ser Pro Leu Ser Leu Pro Val Thr Pro Gly
 1               5                  10                  15

Gln Pro Ala Ser Ile Ser Cys Arg Ala Ser Arg Ser Leu Val His Ser
                20                  25                  30

Asn Arg Asn Thr Tyr Leu His Trp Tyr Gln Gln Lys Pro Gly Gln Ala
            35                  40                  45

Pro Arg Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Arg Gly Thr Lys Leu Glu Ile Lys
```

<210> SEQ ID NO 69
<211> LENGTH: 115
<212> TYPE: PRT
<213> ORGANISM: Artificial Sequence
<220> FEATURE:
<223> OTHER INFORMATION: modified antibody fragment

<400> SEQUENCE: 69

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Gly Glu Gly Leu Glu Trp Ile
        35                  40                  45

Gly Ala Ile Asp Pro Lys Thr Gly Asp Thr Ala Tyr Ser Gln Ser Phe
    50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 70
<211> LENGTH: 112
<212> TYPE: PRT
<213> ORGANISM: Artificial Sequence
<220> FEATURE:
<223> OTHER INFORMATION: modified antibody fragment

<400> SEQUENCE: 70

Asp Ile Val Met Thr Gln Ser Pro Leu Ser Leu Pro Val Thr Pro Gly
1               5                   10                  15

Glu Pro Ala Ser Ile Ser Cys Arg Ala Ser Gln Ser Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 71
<211> LENGTH: 115
<212> TYPE: PRT
<213> ORGANISM: Artificial Sequence
<220> FEATURE:
<223> OTHER INFORMATION: modified antibody fragment

<400> SEQUENCE: 71

Gln Val Gln Leu Val Gln Ser Gly Ala Glu Val Lys Lys Pro Gly Ala
1               5                   10                  15

```
Ser Val Thr Val Ser Cys Lys Ala Ser Gly Tyr Thr Phe Thr Asp Tyr
            20                  25                  30

Glu Met His Trp Ile Arg Gln Pro Gly Glu Gly Leu Glu Trp Ile
        35                  40                  45

Gly Ala Ile Asp Pro Lys Thr Gly Asp Thr Ala Tyr Ser Glu Ser Phe
 50                  55                  60

Gln Asp Arg Val Thr Leu Thr Ala Asp Lys Ser Thr Ser Thr Ala Tyr
65                   70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
                100                 105                 110

Val Ser Ser
        115

<210> SEQ ID NO 72
<211> LENGTH: 112
<212> TYPE: PRT
<213> ORGANISM: Artificial Sequence
<220> FEATURE:
<223> OTHER INFORMATION: modified antibody fragment

<400> SEQUENCE: 72

Asp Ile Val Met Thr Gln Ser Pro Leu Ser Leu Pro Val Thr Pro Gly
1               5                   10                  15

Glu Pro Ala Ser Ile Ser Cys Gln Ala Ser Glu Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
                100                 105                 110

<210> SEQ ID NO 73
<211> LENGTH: 112
<212> TYPE: PRT
<213> ORGANISM: Artificial Sequence
<220> FEATURE:
<223> OTHER INFORMATION: modified antibody fragment

<400> SEQUENCE: 73

Asp Ile Val Met Thr Gln Ser Pro Leu Ser Leu Pro Val Thr Pro Gly
1               5                   10                  15

Glu Pro Ala Ser Ile Ser Cys Gln Ala Ser Glu Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
```

```
                    85                  90                  95

Thr His Val Pro Pro Thr Phe Gly Gln Gly Thr Lys Val Glu Ile Glu
            100                 105                 110

<210> SEQ ID NO 74
<211> LENGTH: 330
<212> TYPE: PRT
<213> ORGANISM: homo sapiens

<400> SEQUENCE: 74

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 75
<211> LENGTH: 326
```

<212> TYPE: PRT
<213> ORGANISM: homo sapiens

<400> SEQUENCE: 75

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 76
<211> LENGTH: 377
<212> TYPE: PRT
<213> ORGANISM: homo sapiens

<400> SEQUENCE: 76

Ala Ser Thr Lys Gly Pro Ser Val Phe Pro Leu Ala Pro Cys Ser Arg
1               5                   10                  15
```

-continued

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 77
<211> LENGTH: 327
<212> TYPE: PRT
<213> ORGANISM: homo sapiens

<400> SEQUENCE: 77

Ala Ser Thr Lys Gly Pro Ser Val Phe Pro Leu Ala Pro Cys Ser Arg
1               5                   10                  15
```

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 78
<211> LENGTH: 374
<212> TYPE: PRT
<213> ORGANISM: homo sapiens

<400> SEQUENCE: 78

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
            35                  40                  45

Pro Gly Ser Ser Ser Thr Gln Trp Phe Leu Asn Gly Thr Ala Thr Gln

```
                    50                  55                  60
Thr Ser Thr Pro Ser Tyr Arg Ile Thr Ser Ala Ser Val Asn Asp Ser
 65                  70                  75                  80

Gly Glu Tyr Arg Cys Gln Arg Gly Leu Ser Gly Arg Ser Asp Pro Ile
                     85                  90                  95

Gln Leu Glu Ile His Arg Gly Trp Leu Leu Gln Val Ser Ser Arg
                100                 105                 110

Val Phe Thr Glu Gly Glu Pro Leu Ala Leu Arg Cys His Ala Trp Lys
            115                 120                 125

Asp Lys Leu Val Tyr Asn Val Leu Tyr Tyr Arg Asn Gly Lys Ala Phe
            130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
                180                 185                 190

Val Leu Asn Ala Ser Val Thr Ser Pro Leu Leu Glu Gly Asn Leu Val
                195                 200                 205

Thr Leu Ser Cys Glu Thr Lys Leu Leu Leu Gln Arg Pro Gly Leu Gln
                210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
                260                 265                 270

Ser Pro Glu Leu Glu Leu Gln Val Leu Gly Leu Gln Leu Pro Thr Pro
                275                 280                 285

Val Trp Phe His Val Leu Phe Tyr Leu Ala Val Gly Ile Met Phe Leu
                290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Glu Leu Lys
                340                 345                 350

Cys Gln Glu Gln Lys Glu Glu Gln Leu Gln Glu Gly Val His Arg Lys
                355                 360                 365

Glu Pro Gln Gly Ala Thr
                370

<210> SEQ ID NO 79
<211> LENGTH: 316
<212> TYPE: PRT
<213> ORGANISM: homo sapiens

<400> SEQUENCE: 79

Met Thr Met Glu Thr Gln Met Ser Gln Asn Val Cys Pro Arg Asn Leu
 1               5                  10                  15

Trp Leu Leu Gln Pro Leu Thr Val Leu Leu Leu Leu Ala Ser Ala Asp
                 20                  25                  30

Ser Gln Ala Ala Pro Pro Lys Ala Val Leu Lys Leu Glu Pro Pro Trp
             35                  40                  45
```

Ile Asn Val Leu Gln Glu Asp Ser Val Thr Leu Thr Cys Gln Gly Ala
    50                  55                  60

Arg Ser Pro Glu Ser Asp Ser Ile Gln Trp Phe His Asn Gly Asn Leu
65                  70                  75                  80

Ile Pro Thr His Thr Gln Pro Ser Tyr Arg Phe Lys Ala Asn Asn Asn
                85                  90                  95

Asp Ser Gly Glu Tyr Thr Cys Gln Thr Gly Gln Thr Ser Leu Ser Asp
            100                 105                 110

Pro Val His Leu Thr Val Leu Ser Glu Trp Leu Val Leu Gln Thr Pro
        115                 120                 125

His Leu Glu Phe Gln Glu Gly Glu Thr Ile Met Leu Arg Cys His Ser
130                 135                 140

Trp Lys Asp Lys Pro Leu Val Lys Val Thr Phe Phe Gln Asn Gly Lys
145                 150                 155                 160

Ser Gln Lys Phe Ser His Leu Asp Pro Thr Phe Ser Ile Pro Gln Ala
                165                 170                 175

Asn His Ser His Ser Gly Asp Tyr His Cys Thr Gly Asn Ile Gly Tyr
            180                 185                 190

Thr Leu Phe Ser Ser Lys Pro Val Thr Ile Thr Val Gln Val Pro Ser
        195                 200                 205

Met Gly Ser Ser Ser Pro Met Gly Val Ile Val Ala Val Val Ile Ala
    210                 215                 220

Thr Ala Val Ala Ala Ile Val Ala Ala Val Val Ala Leu Ile Tyr Cys
225                 230                 235                 240

Arg Lys Lys Arg Ile Ser Ala Asn Ser Thr Asp Pro Val Lys Ala Ala
                245                 250                 255

Gln Phe Glu Pro Pro Gly Arg Gln Met Ile Ala Ile Arg Lys Arg Gln
            260                 265                 270

Leu Glu Glu Thr Asn Asn Asp Tyr Glu Thr Ala Asp Gly Gly Tyr Met
        275                 280                 285

Thr Leu Asn Pro Arg Ala Pro Thr Asp Asp Asp Lys Asn Ile Tyr Leu
    290                 295                 300

Thr Leu Pro Pro Asn Asp His Val Asn Ser Asn Asn
305                 310                 315

<210> SEQ ID NO 80
<211> LENGTH: 291
<212> TYPE: PRT
<213> ORGANISM: homo sapiens

<400> SEQUENCE: 80

Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
                20                  25                  30

Ala Val Leu Phe Leu Ala Pro Val Ala Gly Thr Pro Ala Ala Pro Pro
            35                  40                  45

Lys Ala Val Leu Lys Leu Glu Pro Gln Trp Ile Asn Val Leu Gln Glu
    50                  55                  60

Asp Ser Val Thr Leu Thr Cys Arg Gly Thr His Ser Pro Glu Ser Asp
65                  70                  75                  80

Ser Ile Gln Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
            100                 105                 110

```
Cys Gln Thr Gly Gln Thr Ser Leu Ser Asp Pro Val His Leu Thr Val
            115                 120                 125

Leu Ser Glu Trp Leu Val Leu Gln Thr Pro His Leu Glu Phe Gln Glu
    130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
        195                 200                 205

Pro Val Thr Ile Thr Val Gln Ala Pro Ser Ser Pro Met Gly Ile
    210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Asn Pro
                245                 250                 255

Thr Asn Pro Asp Glu Ala Asp Lys Val Gly Ala Glu Asn Thr Ile Thr
            260                 265                 270

Tyr Ser Leu Leu Met His Pro Asp Ala Leu Glu Glu Pro Asp Asp Gln
        275                 280                 285

Asn Arg Ile
    290

<210> SEQ ID NO 81
<211> LENGTH: 254
<212> TYPE: PRT
<213> ORGANISM: homo sapiens

<400> SEQUENCE: 81

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Arg Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
```

```
                        180                 185                 190
Gly Leu Ser Val Ser Thr Ile Ser Ser Phe Phe Pro Pro Gly Tyr Gln
            195                 200                 205

Val Ser Phe Cys Leu Val Met Val Leu Leu Phe Ala Val Asp Thr Gly
            210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
            245                 250

<210> SEQ ID NO 82
<211> LENGTH: 233
<212> TYPE: PRT
<213> ORGANISM: homo sapiens

<400> SEQUENCE: 82

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Ser Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
            210                 215                 220

Leu Tyr Phe Ser Val Lys Thr Asn Ile
225                 230
```

GPC3-TARGETING DRUG WHICH IS ADMINISTERED TO PATIENT RESPONSIVE TO GPC3-TARGETING DRUG THERAPY

CROSS-REFERENCE TO RELATED APPLICATIONS

This application is a U.S. National Phase of PCT Application No. PCT/JP2015/002352, filed May 8, 2015, which claims the benefit of U.S. Provisional Patent Application No. 61/990,238, filed May 8, 2014, each of which is incorporated herein by reference.

REFERENCE TO SEQUENCE LISTING SUBMITTED ELECTRONICALLY

The content of the electronically submitted sequence listing (Name: 3467_0230001_SeqListing.txt; Size: 78,581 bytes; and Date of Creation: Nov. 7, 2016) filed on Nov. 7, 2016, is incorporated herein by reference in its entirety.

BACKGROUND OF THE INVENTION

Technical Field

The present invention provides a method for determining the efficacy of GPC3-targeting drug therapy for cancer in a patient or determining the continuation of GPC3-targeting drug therapy for a patient. The present invention also provides a GPC3-targeting drug or a preparation which is to be further administered to a patient for the efficacy of the GPC3-targeting drug therapy has been determined or the continuation of the GPC3-targeting drug therapy has been determined.

Background Art

Hepatocellular cancer is reportedly the fifth leading cause of cancer deaths worldwide, accounting for approximately 600,000 deaths each year (Non Patent Literature 1). Most patients with hepatocellular cancer die within 1 year after being diagnosed with the disease. Unfortunately, hepatocellular cancer cases are frequently diagnosed at a late stage which rarely responds to curative therapy. Still, medical treatments including chemotherapy, chemoembolization, ablation, and proton beam therapy are insufficiently effective for such patients. Many patients exhibit recurrence of the disease with vascular invasion and multiple intrahepatic metastases, which rapidly progresses to the advanced stage. Their 5-year survival rates are only 7% (Non Patent Literature 2). Patients with hepatocellular cancer amenable to the resection of local foci have relatively good prognosis, though their 5-year survival rates still remain at a level of 15% and 39% (Non Patent Literature 3). Thus, there has been a demand in the art for novel therapy for such a malignant disease hepatocellular cancer.

Hepatocellular cancer is reportedly responsible for more than 90% of primary liver cancer cases in Japan. Medical methods for treating such hepatocellular cancer include, for example, chemotherapy-based transcatheter arterial embolization (TAE) therapy, which involves inducing the selective necrosis of the hepatocellular cancer by the injection of a mixture of an oil-based contrast medium (Lipiodol), an anticancer agent, and an obstructing substance (Gelfoam) into the hepatic artery (which serves as a nutrient supply pathway to the tumor) resulting in the obstruction of the nutrient artery. In addition, invasive approaches are used, such as percutaneous ethanol injection, percutaneous microwave coagulation therapy, and radiofrequency ablation. Also, clinical trials have been conducted on systemic chemotherapy using chemotherapeutic agents such as fluorouracil (5-FU), uracil-tegafur (UFT), mitomycin C (MMC), mitoxantrone (DHAD), adriamycin (ADR), epirubicin (EPI), and cisplatin (CDDP) either alone or in combination with interferon (IFN) (Non Patent Literature 4).

Meanwhile, an orally active form of sorafenib (Nexavar, BAY43-9006) has been approved, which is more advantageously effective than the chemotherapeutic agents described above in such a way that this agent blocks the growth of cancer cells by inhibiting Raf kinase in the Raf/MEK/ERK signal transduction while the agent exerts antiangiogenic effects by targeting VEGFR-2, VEGFR-3, and PDGFR-β tyrosine kinases. The efficacy of sorafenib has been studied in two phase-III multicenter placebo-controlled trials (Sorafenib HCC Assessment Randomized Protocol (SHARP) trial and Asia-Pacific trial) targeting advanced hepatocellular cancer. Sorafenib was confirmed to prolong survival durations, with HR of 0.68, in both of these trials. In the SHARP trial, sorafenib prolonged the survival duration to 10.7 months versus 7.9 months with the placebo. In the Asian trial, this agent prolonged the survival duration to 6.5 months versus 4.2 months with the placebo. The agent, however, had a low objective response rate and showed no prolongation of a time to symptomatic progression, though the agent prolonged a time to tumor progression (5.5 months versus 2.8 months in the European and American trial and 2.8 months versus 1.4 months in the Asian trial) on the images. The Asian cohorts exhibited a short duration of life prolongation, which is probably because their treatments were started at a slightly later stage during the disease process in the Asian region compared with Europe and the United States (Non Patent Literatures 5 and 6).

As liver cancer progresses, its specific symptoms associated with liver dysfunction are generally observed, such as anorexia, weight loss, general malaise, palpable right hypochondrial mass, right hypochondrial pain, sense of abdominal fullness, fever, and jaundice. The chemotherapeutic agents (e.g., sorafenib), however, have complications to be overcome, including their inherent adverse reactions such as diarrhea or constipation, anemia, suppression of the immune system to cause infection or sepsis (with lethal severity), hemorrhage, cardiac toxicity, hepatic toxicity, renal toxicity, anorexia, and weight loss.

Although particular early-stage symptoms are not initially observed in liver cancer, its specific symptoms associated with liver dysfunction, such as anorexia, weight loss, general malaise, palpable right hypochondrial mass, right hypochondrial pain, sense of abdominal fullness, fever, and jaundice, are generally observed with progression of the liver cancer. According to clinical observation, such symptoms are enhanced by use of the chemotherapeutic agents. For example, anorexia in a patient with detectable liver cancer cells and symptoms such as weight loss associated with or independent of the anorexia may be more enhanced by the administration of the chemotherapeutic agents to the patient than without the use of the chemotherapeutic agents. In some cases, the use of the chemotherapeutic agents must be discontinued for the patient having such symptoms. These enhanced symptoms are impediments to treatments with the chemotherapeutic agents. Thus, there has been a demand for the establishment of excellent therapy from the viewpoint of, for example, improving therapeutic effects or improving QOL of patients to be treated.

Glypican 3 (GPC3) is frequently expressed at a high level in liver cancer and as such, seems to be useful in the identification of its functions in liver cancer or as a therapeutic or diagnostic target of liver cancer.

Under the circumstances described above, drugs are under development with GPC3 as a therapeutic target of liver cancer. A liver cancer drug comprising an anti-GPC3 antibody as an active ingredient has been developed, the antibody having antibody-dependent-cellular cytotoxicity (hereinafter, referred to as "ADCC") activity and/or complement-dependent-cytotoxicity (hereinafter, referred to as "CDC") activity against cells expressing GPC3 (Patent Literature 1). Also, a GPC3-targeting drug comprising a humanized anti-GPC3 antibody having ADCC activity and CDC activity as an active ingredient has been developed (Patent Literature 2). Further GPC3-targeting drugs have been developed, which comprise a humanized anti-GPC3 antibody with enhanced ADCC activity (Patent Literatures 3 and 4) or an anti-GPC3 antibody having ADCC activity and CDC activity as well as improved plasma dynamics (Patent Literature 5). These anti-GPC3 antibodies in combination therapy with the chemotherapeutic agents such as sorafenib have been found to attenuate the adverse reactions, for example, brought about by the sole therapy of the chemotherapeutic agents (e.g., sorafenib) and also found to exhibit synergistic effects based on these agents (Patent Literature 6). Accordingly, excellent methods for treating liver cancer are in the process of being established using GPC3-targeting drugs as the nucleus from the viewpoint of, for example, improving therapeutic effects or improving QOL of patients to be treated.

Meanwhile, GPC3-targeting methods for diagnosing liver cancer are also under development. GPC3 is known to be processed, at the particular site, by convertase, phospholipase D, Notum, or an unidentified mechanism during or after expression on cell surface (Non Patent Literatures 7 and 8). By use of such a phenomenon, a diagnostic agent or a diagnostic method for liver cancer has been developed, which involves an antibody capable of binding to an epitope in a soluble form of GPC3 secreted into the plasma of a patient after processing (Patent Literature 7). Also, a diagnostic agent or a diagnostic method for liver cancer has been developed, which involves an antibody capable of binding to an epitope in an anchored form of GPC3 still existing on cell surface after processing in a tissue preparation or the like isolated from a patient (Patent Literature 8). These diagnostic agents or diagnostic methods, however, are means for detecting the presence of liver cancer in a patient to be tested. Neither a method for determining the efficacy of GPC3-targeting drug therapy for a patient treated with the GPC3-targeting drug therapy nor a method for determining the continuation of GPC3-targeting drug therapy for the patient has been known yet.

References cited herein are as listed below. The contents described in these literatures are incorporated herein by reference in their entirety. It should be noted that none of these literatures are admitted to be the prior art to the present invention.

CITATION LIST

Patent Literature

Patent Literature 1 WO2003/000883
Patent Literature 2 WO2006/006693
Patent Literature 3 WO2006/046751
Patent Literature 4 WO2007/047291
Patent Literature 5 WO2009/041062
Patent Literature 6 WO2009/122667
Patent Literature 7 WO2004/038420
Patent Literature 8 WO2009/116659

Non Patent Literature

Non Patent Literature 1 Llovet J M, Burroughs A, Bruix J; Lancet (2003), 362, 1907-17
Non Patent Literature 2 Bosch F X, Ribes J, Cleries R; Gastroenterology (2004), 127, S5-16
Non Patent Literature 3 Takenaka K, Kawahara N, Yamamoto K, Kajiyama K, Maeda T, Itasaka H, Shirabe K, Nishizaki T, Yanaga K, Sugimachi K; Arch Surg (1996), 131, 71-6
Non Patent Literature 4 Yeo W, Mok T S, Zee B, Leung T W, Lai P B, Lau W Y, Koh J, Mo F K, Yu S C, Chan A T, Hui P, Ma B, Lam K C, Ho W M, Wong H T, Tang A, Johnson P J; J Natl Cancer Inst (2005), 97, 1532-8
Non Patent Literature 5 Llovet J, Ricci S, Mazzaferro V, Hilgard P, Gane E, et al. Sorafenib in advanced hepatocellular carcinoma. New Eng. J. Med. (2008) 359, 378-90
Non Patent Literature 6 Cheng A L, Chen Z, Tsao C J, Qin S, Kim J S, et al. Efficacy and safety of sorafenib in patients in the Asia-Pacific region with advanced hepatocellular carcinoma: a phase III randomized, double-blind, placebo-controlled trial. Lancet Oncol. (2009) 10, 25-34
Non Patent Literature 7 De Cat B, Muyldermans S-Y, Coomans C, Degeest G, Vanderschueren B, et al. Processing by proprotein convertases is required for glypican-3 modulation of cell survival, Wnt signaling, and gastrulation movements. J. Cell. Biol. (2003) 163, 625-635
Non Patent Literature 8 Traister A, Shi W and Filmus J. Mammalian Notum induces the release of glypicans and other GPI-anchored proteins from the cell surface. Biochem. J. (2008) 410, 503-511

BRIEF SUMMARY OF THE INVENTION

Technical Problem

The present invention has been made in light of the situations as described above, and an object of the present invention is to provide a method for determining the efficacy of GPC3-targeting drug therapy for a patient treated with the GPC3-targeting drug therapy or determining the continuation of GPC3-targeting drug therapy for the patient. Another object of the present invention is to provide a GPC3-targeting drug or a preparation which is to be further administered to a patient for which the efficacy of the GPC3-targeting drug therapy has been determined or the continuation of the GPC3-targeting drug therapy has been determined.

Solution to Problem

The present inventors have conducted diligent studies under the situations as described above and consequently created a method comprising measuring the number of an immunocyte or an expression level of a molecule expressed on the immunocyte in a biological sample isolated from a patient treated with GPC3-targeting drug therapy, wherein when the number of an immunocyte or the expression level is a predetermined value or when the number of an immunocyte or the expression level is a predetermined value as a result of receiving the GPC3-targeting drug therapy, the efficacy of the GPC3-targeting drug therapy is determined or the continuation of the GPC3-targeting drug therapy is determined. The present inventors have also created a GPC3-targeting drug or a preparation which is to be administered to a patient for which the efficacy of the GPC3-targeting drug therapy has been determined or the continuation of the GPC3-targeting drug therapy has been determined.

More specifically, the present invention provides the following aspects:

[1] a method for determining the efficacy of GPC3-targeting drug therapy for cancer in a patient or determining the continuation of GPC3-targeting drug therapy for a patient, comprising measuring the number of an immunocyte or an expression level of a molecule expressed on the immunocyte in a biological sample isolated from the patient before the start of GPC3-targeting drug therapy and/or the patient treated with the GPC3-targeting drug therapy, wherein when the number of an immunocyte or the expression level of a molecule expressed on the immunocyte is a predetermined value, the efficacy of the GPC3-targeting drug therapy is determined or the continuation of the GPC3-targeting drug therapy is determined,

[2] the method according to [1], wherein the biological sample is peripheral blood isolated from the patient,

[3] the method according to [1] or [2], wherein the immunocyte is at least one cell selected from a leukocyte, a monocyte, a neutrophil, and a lymphocyte,

[4] the method according to [3], wherein the lymphocyte is at least one lymphocyte cell selected from a CD45+ lymphocyte, a CD3+ T cell, a CD4+ T cell, and a CD8+ T cell,

[5] the method according to [3], wherein the lymphocyte is at least one lymphocyte cell selected from a CD16+ NK cell, an NKp46+ NK cell, and a CD56−/CD16+ NK cell,

[6] the method according to [1] or [2], wherein the molecule expressed on the immunocyte is CD16 or CD107a,

[7] the method according to any of [1] to [7], wherein the patient has a polymorphism at least one allele having Val at amino acid residue 158 of FcγRIIIA and/or at least one allele having His at amino acid residue 131 of FcγRIIA,

[8] the method according to any of [1] to [7], wherein the cancer is liver cancer,

[9] the method according to any of [1] to [8], wherein the GPC3-targeting drug is administered to achieve a blood trough level of 200 μg/ml or higher in the cancer patient,

[10] the method according to any of [1] to [9], wherein the GPC3-targeting drug comprises an anti-GPC3 antibody as an active ingredient,

[11] the method according to [10], wherein the anti-GPC3 antibody has antibody-dependent cellular cytotoxicity (ADCC) activity and/or complement-dependent cytotoxicity (CDC) activity,

[12] the method according to [10] or [11], wherein the anti-GPC3 antibody is an anti-GPC3 chimeric antibody or a humanized anti-GPC3 antibody comprising any of the following (1) to (5):

(1) heavy chain CDR1, heavy chain CDR2, and heavy chain CDR3 represented by SEQ ID NOs: 4, 5, and 6, respectively, and light chain CDR1, light chain CDR2, and light chain CDR3 represented by SEQ ID NOs: 7, 8, and 9, respectively;

(2) heavy chain CDR1, heavy chain CDR2, and heavy chain CDR3 represented by SEQ ID NOs: 12, 13, and 14, respectively, and light chain CDR1, light chain CDR2, and light chain CDR3 represented by SEQ ID NOs: 15, 16, and 17, respectively;

(3) heavy chain CDR1, heavy chain CDR2, and heavy chain CDR3 represented by SEQ ID NOs: 20, 21, and 22, respectively, and light chain CDR1, light chain CDR2, and light chain CDR3 represented by SEQ ID NOs: 23, 24, and 25, respectively;

(4) heavy chain CDR1, heavy chain CDR2, and heavy chain CDR3 represented by SEQ ID NOs: 28, 29, and 30, respectively, and light chain CDR1, light chain CDR2, and light chain CDR3 represented by SEQ ID NOs: 31, 32, and 33, respectively; and (5) heavy chain CDR1, heavy chain CDR2, and heavy chain CDR3 represented by SEQ ID NOs: 36, 37, and 38, respectively, and light chain CDR1, light chain CDR2, and light chain CDR3 represented by SEQ ID NOs: 39, 40, and 41, respectively,

[13] The method according to any of [10] to [12], wherein the anti-GPC3 antibody comprises any of the following (1) to (6):

(1) a heavy chain variable region selected from the group of heavy chain variable regions represented by SEQ ID NOs: 44, 45, 46, 47, 48, 49, and 50 and a light chain variable region represented by SEQ ID NO: 51;

(2) a heavy chain variable region selected from the group of heavy chain variable regions represented by SEQ ID NOs: 44, 45, 46, 47, 48, 49, and 50 and a light chain variable region selected from the group of light chain variable regions represented by SEQ ID NOs: 52, 53, 54, 55, 56, 57, 58, 59, 60, 61, 62, 63, 64, 65, and 66;

(3) a heavy chain variable region represented by SEQ ID NO: 67 and a light chain variable region represented by SEQ ID NO: 68;

(4) a heavy chain variable region represented by SEQ ID NO: 69 and a light chain variable region represented by SEQ ID NO: 70;

(5) a heavy chain variable region represented by SEQ ID NO: 71 and a light chain variable region represented by SEQ ID NO: 72; and (6) a heavy chain variable region represented by SEQ ID NO: 71 and a light chain variable region represented by SEQ ID NO: 73,

[14] the method according to [10], wherein the GPC3-targeting drug comprises an anti-GPC3 antibody conjugated with a cytotoxic substance,

[15] a GPC3-targeting drug which is to be administered to a cancer patient in which the number of an immunocyte or an expression level of a molecule expressed on the immunocyte is a predetermined value,

[16] the GPC3-targeting drug according to [15], wherein the number of an immunocyte or the expression level of a molecule expressed on the immunocyte is the number of an immunocyte or an expression level of a molecule expressed on the immunocyte in a biological sample isolated from the cancer patient,

[17] the drug according to [16], wherein the biological sample is peripheral blood isolated from the cancer patient,

[18] the drug according to any of [15] to [17], wherein the immunocyte is at least one cell selected from a leukocyte, a monocyte, a neutrophil, and a lymphocyte,

[19] the drug according to [18], wherein the lymphocyte is at least one lymphocyte cell selected from a CD45+ lymphocyte, a CD3+ T cell, a CD4+ T cell, and a CD8+ T cell,

[20] the drug according to [18], wherein the lymphocyte is at least one lymphocyte cell selected from a CD16+ NK cell, an NKp46+ NK cell, and a CD56−/CD16+ NK cell,

[21] the drug according to any of [15] to [17], wherein the molecule expressed on the immunocyte is CD16 or CD107a,

[22] the drug according to any of [15] to [21], wherein the patient has a polymorphism that results in homozygous or heterozygous Val at amino acid residue 158 of FcγRIIIA and/or a polymorphism that results in homozygous or heterozygous His at amino acid residue 131 of FcγRIIA,

[23] the drug according to any of [15] to [22], wherein the cancer patient is a liver cancer patient,

[24] the drug according to any of [15] to [23], wherein the GPC3-targeting drug is administered to achieve a blood trough level of 200 μg/ml or higher in the cancer patient,

[25] the drug according to any of [15] to [24], wherein the GPC3-targeting drug comprises an anti-GPC3 antibody as an active ingredient,

[26] the drug according to [25], wherein the anti-GPC3 antibody has antibody-dependent cellular cytotoxicity (ADCC) activity and/or complement-dependent cytotoxicity (CDC) activity,

[27] the drug according to [25] or [26], wherein the anti-GPC3 antibody is an anti-GPC3 chimeric antibody or a humanized anti-GPC3 antibody comprising any of the following (1) to (5):
  (1) heavy chain CDR1, heavy chain CDR2, and heavy chain CDR3 represented by SEQ ID NOs: 4, 5, and 6, respectively, and light chain CDR1, light chain CDR2, and light chain CDR3 represented by SEQ ID NOs: 7, 8, and 9, respectively;
  (2) heavy chain CDR1, heavy chain CDR2, and heavy chain CDR3 represented by SEQ ID NOs: 12, 13, and 14, respectively, and light chain CDR1, light chain CDR2, and light chain CDR3 represented by SEQ ID NOs: 15, 16, and 17, respectively;
  (3) heavy chain CDR1, heavy chain CDR2, and heavy chain CDR3 represented by SEQ ID NOs: 20, 21, and 22, respectively, and light chain CDR1, light chain CDR2, and light chain CDR3 represented by SEQ ID NOs: 23, 24, and 25, respectively;
  (4) heavy chain CDR1, heavy chain CDR2, and heavy chain CDR3 represented by SEQ ID NOs: 28, 29, and 30, respectively, and light chain CDR1, light chain CDR2, and light chain CDR3 represented by SEQ ID NOs: 31, 32, and 33, respectively; and
  (5) heavy chain CDR1, heavy chain CDR2, and heavy chain CDR3 represented by SEQ ID NOs: 36, 37, and 38, respectively, and light chain CDR1, light chain CDR2, and light chain CDR3 represented by SEQ ID NOs: 39, 40, and 41, respectively,

[28] the drug according to any of [25] to [27], wherein the anti-GPC3 antibody comprises any of the following (1) to (6):
  (1) a heavy chain variable region selected from the group of heavy chain variable regions represented by SEQ ID NOs: 44, 45, 46, 47, 48, 49, and 50 and a light chain variable region represented by SEQ ID NO: 51;
  (2) a heavy chain variable region selected from the group of heavy chain variable regions represented by SEQ ID NOs: 44, 45, 46, 47, 48, 49, and 50 and a light chain variable region selected from the group of light chain variable regions represented by SEQ ID NOs: 52, 53, 54, 55, 56, 57, 58, 59, 60, 61, 62, 63, 64, 65, and 66;
  (3) a heavy chain variable region represented by SEQ ID NO: 67 and a light chain variable region represented by SEQ ID NO: 68;
  (4) a heavy chain variable region represented by SEQ ID NO: 69 and a light chain variable region represented by SEQ ID NO: 70;
  (5) a heavy chain variable region represented by SEQ ID NO: 71 and a light chain variable region represented by SEQ ID NO: 72; and
  (6) a heavy chain variable region represented by SEQ ID NO: 71 and a light chain variable region represented by SEQ ID NO: 73,

[29] the drug according to [25], wherein the GPC3-targeting drug comprises an anti-GPC3 antibody conjugated with a cytotoxic substance,

[30] a preparation for GPC3-targeting treatment, comprising an instruction stating that the preparation is to be further administered to a cancer patient having a predetermined value of the number of an immunocyte or an expression level of a molecule expressed on the immunocyte in a biological sample isolated from the cancer patient before the start of GPC3-targeting drug therapy,

[31] a preparation for GPC3-targeting treatment, comprising an instruction stating that the preparation is to be further administered to a cancer patient having a predetermined value of the number of an immunocyte or an expression level of a molecule expressed on the immunocyte in a biological sample isolated from the cancer patient after the start of GPC3-targeting drug therapy,

[32] the preparation according to [30] or [31], wherein the biological sample is peripheral blood isolated from the cancer patient,

[33] the preparation according to any of [30] to [32], wherein the immunocyte is at least one cell selected from a leukocyte, a monocyte, a neutrophil, and a lymphocyte,

[34] the preparation according to [33], wherein the lymphocyte is at least one lymphocyte cell selected from a CD45+ lymphocyte, a CD3+ T cell, a CD4+ T cell, and a CD8+ T cell,

[35] the preparation according to [33], wherein the lymphocyte is at least one lymphocyte cell selected from a CD16+ NK cell, an NKp46+ NK cell, and a CD56−/CD16+ NK cell,

[36] the preparation according to any of [30] to [32], wherein the molecule expressed on the immunocyte is CD16 or CD107a,

[37] the preparation according to any of [30] to [36], wherein the patient has a polymorphism that results in homozygous or heterozygous Val at amino acid residue 158 of FcγRIIIA and/or a polymorphism that results in homozygous or heterozygous His at amino acid residue 131 of FcγRIIA,

[38] the preparation according to any of [30] to [37], wherein the cancer patient is a liver cancer patient,

[39] the preparation according to any of [30] to [38], wherein the GPC3-targeting drug is administered to achieve a blood trough level of 200 μg/ml or higher in the cancer patient,

[40] the preparation according to any of [30] to [39], wherein the GPC3-targeting drug comprises an anti-GPC3 antibody as an active ingredient,

[41] the preparation according to [40], wherein the anti-GPC3 antibody has antibody-dependent cellular cytotoxicity (ADCC) activity and/or complement-dependent cytotoxicity (CDC) activity,

[42] the preparation according to [40] or [41], wherein the anti-GPC3 antibody is an anti-GPC3 chimeric antibody or a humanized anti-GPC3 antibody comprising any of the following (1) to (5):
  (1) heavy chain CDR1, heavy chain CDR2, and heavy chain CDR3 represented by SEQ ID NOs: 4, 5, and 6, respectively, and light chain CDR1, light chain CDR2, and light chain CDR3 represented by SEQ ID NOs: 7, 8, and 9, respectively;
  (2) heavy chain CDR1, heavy chain CDR2, and heavy chain CDR3 represented by SEQ ID NOs: 12, 13, and 14, respectively, and light chain CDR1, light chain CDR2, and light chain CDR3 represented by SEQ ID NOs: 15, 16, and 17, respectively;
  (3) heavy chain CDR1, heavy chain CDR2, and heavy chain CDR3 represented by SEQ ID NOs: 20, 21, and 22, respectively, and light chain CDR1, light chain CDR2, and light chain CDR3 represented by SEQ ID NOs: 23, 24, and 25, respectively;
  (4) heavy chain CDR1, heavy chain CDR2, and heavy chain CDR3 represented by SEQ ID NOs: 28, 29, and 30, respectively, and light chain CDR1, light chain CDR2, and light chain CDR3 represented by SEQ ID NOs: 31, 32, and 33, respectively; and
  (5) heavy chain CDR1, heavy chain CDR2, and heavy chain CDR3 represented by SEQ ID NOs: 36, 37, and 38, respectively, and light chain CDR1, light chain CDR2, and light chain CDR3 represented by SEQ ID NOs: 39, 40, and 41, respectively,

[43] the preparation according to any of [40] to [42], wherein the anti-GPC3 antibody comprises any of the following (1) to (6):
  (1) a heavy chain variable region selected from the group of heavy chain variable regions represented by SEQ ID NOs: 44, 45, 46, 47, 48, 49, and 50 and a light chain variable region represented by SEQ ID NO: 51;
  (2) a heavy chain variable region selected from the group of heavy chain variable regions represented by SEQ ID NOs: 44, 45, 46, 47, 48, 49, and 50 and a light chain variable region selected from the group of light chain variable regions represented by SEQ ID NOs: 52, 53, 54, 55, 56, 57, 58, 59, 60, 61, 62, 63, 64, 65, and 66;
  (3) a heavy chain variable region represented by SEQ ID NO: 67 and a light chain variable region represented by SEQ ID NO: 68;
  (4) a heavy chain variable region represented by SEQ ID NO: 69 and a light chain variable region represented by SEQ ID NO: 70;
  (5) a heavy chain variable region represented by SEQ ID NO: 71 and a light chain variable region represented by SEQ ID NO: 72; and
  (6) a heavy chain variable region represented by SEQ ID NO: 71 and a light chain variable region represented by SEQ ID NO: 73,

[44] the preparation according to [40], wherein the GPC3-targeting drug comprises an anti-GPC3 antibody conjugated with a cytotoxic substance,

[45] a method for treating cancer, comprising administering a GPC3-targeting drug to a patient determined by a method according to any of [1] to [14].

BRIEF DESCRIPTION OF THE DRAWINGS

FIG. 1 is a diagram showing the progression-free survival duration or overall survival duration of patients treated with GPC3-targeting drug therapy or placebo. The broken line represents the progression-free survival duration or overall survival duration of a GC33-administered group. The solid line represents the progression-free survival duration or overall survival duration of a placebo group.

FIG. 2 is a diagram showing the progression-free survival duration or overall survival duration of patients treated with GPC3-targeting drug therapy or placebo. The solid line represents the progression-free survival duration or overall survival duration of a placebo group. The dotted line represents the progression-free survival duration or overall survival duration of a high-GC33-exposed group. The broken line represents the progression-free survival duration or overall survival duration of a low-GC33-exposed group.

FIG. 3 is a diagram showing the correlation between the number of neutrophils in blood collected from patients before the start of GPC3-targeting drug therapy and the progression-free survival duration of the patients in a group with the number of neutrophils smaller than, or equal or larger than the median value (3,607 cells/μL). The broken line represents the progression-free survival duration of a GC33-administered group. The solid line represents the progression-free survival duration of a placebo group. The hazard ratio of the GC33-administered group to the placebo group among the groups with a smaller number of neutrophils was 1.229 (p=0.369), whereas the hazard ratio of the GC33-administered group to the placebo group among the groups with a larger number of neutrophils was 0.607 (p=0.030).

FIG. 4 is a diagram showing the correlation between the number of CD4-positive T cells in blood collected from patients before the start of GPC3-targeting drug therapy and the progression-free survival duration of the patients in a group with the number of neutrophils smaller than or larger than the median value (490 cells/μL). The broken line represents the progression-free survival duration of a GC33-administered group. The solid line represents the progression-free survival duration of a placebo group. The hazard ratio of the GC33-administered group to the placebo group among the groups with a smaller number of CD4-positive T cells was 1.273 (p=0.307), whereas the hazard ratio of the GC33-administered group to the placebo group among the groups with a larger number of CD4-positive T cells was 0.635 (p=0.05).

FIG. 5 is a diagram showing the correlation between the number of CD56-negative and CD16-positive NK cells in blood collected from patients before the start of GPC3-targeting drug therapy and the progression-free survival duration of the patients in a group with the number of CD56-negative and CD16-positive NK cells smaller than or larger than the median value (6.3 cells/μL). The broken line represents the progression-free survival duration of a GC33-administered group. The solid line represents the progression-free survival duration of a placebo group. The hazard ratio of the GC33-administered group to the placebo group among the groups with a smaller number of CD56-negative and CD16-positive NK cells was 1.259 (p=0.344), whereas the hazard ratio of the GC33-administered group to the placebo group among the groups with a larger number of CD56-negative and CD16-positive NK cells was 0.571 (p=0.022).

FIG. 6 is a diagram showing the correlation between the expression level (MESF) of CD16 on NK cells in blood collected from patients before the start of GPC3-targeting drug therapy and the progression-free survival duration of the patients in a group with the expression level lower than or higher than the median value (372,254 mesf). The broken line represents the progression-free survival duration of a GC33-administered group. The solid line represents the progression-free survival duration of a placebo group. The hazard ratio of the GC33-administered group to the placebo group among the groups with a lower level of CD16 expression was 1.130 (p=0.612), whereas the hazard ratio of the GC33-administered group to the placebo group among the groups with a higher level of CD16 expression was 0.668 (p=0.101).

FIG. 7 is a diagram showing the correlation between the amount of change in CD16 expression and the progression-free survival duration of a group with the amount of change smaller than (high-ADCC activity group) or larger than (low-ADCC activity group) the median value (−64.33%), wherein the amount of change in CD16 expression was obtained by evaluating the level of ADCC activity against blood cells collected from patients before the start of GPC3-targeting drug therapy on the basis of change in CD16 expression level on cell surface. The solid line represents the progression-free survival duration of a placebo group. The dotted line represents the progression-free survival duration of a high-GC33-exposed group. The broken line represents the progression-free survival duration of a low-GC33-exposed group.

FIG. 8 is a diagram showing the correlation between the amount of change in CD107a expression and the progression-free survival duration of a group with the amount of change larger than (high-ADCC activity group) or smaller than (low-ADCC activity group) the median value (34.15%), wherein the amount of change in CD107a expression was obtained by evaluating the level of ADCC activity against blood cells collected from patients before the start of GPC3-targeting drug therapy on the basis of change in CD107a expression level on cell surface. The solid line represents the progression-free survival duration of a placebo group. The dotted line represents the progression-free survival duration of a high-GC33-exposed group. The broken line represents the progression-free survival duration of a low-GC33-exposed group.

DETAILED DESCRIPTION OF THE INVENTION

Definition

Chemical terms and technical terms used in relation to the present invention have meanings generally understood by those skilled in the art, unless otherwise defined herein.

Indefinite Article

In the present invention, the indefinite articles "a" and "an" refer to one or two or more (i.e., at least one) object(s) grammatically represented by the indefinite articles. For example, "a factor" means one factor or two or more factors.

Amino Acid

Each amino acid is indicated herein by single-letter code or three-letter code, or both, as represented by, for example, Ala/A, Leu/L, Arg/R, Lys/K, Asn/N, Met/M, Asp/D, Phe/F, Cys/C, Pro/P, Gln/Q, Ser/S, Glu/E, Thr/T, Gly/G, Trp/W, His/H, Tyr/Y, Ile/I, and Val/V.

Amino Acid Modification

An amino acid in the amino acid sequence of an antigen-binding molecule can be modified by an appropriately adopted method known in the art such as site-directed mutagenesis (Kunkel et al., Proc. Natl. Acad. Sci. USA (1985) 82, 488-492) or overlap extension PCR. Also, a plurality of methods known in the art can be adopted as methods for modifying an amino acid to substitute the amino acid by an amino acid other than natural one (Annu. Rev. Biophys. Biomol. Struct. (2006) 35, 225-249; and Proc. Natl. Acad. Sci. U.S.A. (2003) 100 (11), 6353-6357). For example, a tRNA-containing cell-free translation system (Clover Direct (Protein Express, an R & D oriented company)) comprising a non-natural amino acid bound with an amber suppressor tRNA complementary to UAG codon (amber codon), which is a stop codon, is also preferably used.

The term "and/or" used herein to represent amino acid modification sites is meant to include every combination appropriately represented by "and" and "or". Specifically, for example, the phrase "amino acids 43, 52, and/or 105 are substituted" includes the following variations of amino acid modification:

(a) position 43, (b) position 52, (c) position 105, (d) positions 43 and 52, (e) positions 43 and 105, (f) positions 52 and 105, and (g) positions 43, 52, and 105.

EU Numbering and Kabat Numbering

According to a method used in the present invention, amino acid positions assigned to antibody CDRs and FRs are defined by the Kabat method (Sequences of Proteins of Immunological Interest, National Institute of Health, Bethesda, Md., 1987 and 1991). When the antigen-binding molecule described herein is an antibody or an antigen-binding fragment, amino acids in variable and constant regions are indicated according to the Kabat numbering and the EU numbering conforming to the Kabat amino acid positions, respectively.

Biological Sample

In the present invention, the term "biological sample" refers to a sample of a tissue or a fluid isolated from a subject. In a non-limiting aspect, examples of such samples include plasma, serum, spinal fluid, lymph, external sections of skin, respiratory tract, intestinal tract, and genitourinary tract, tear, saliva, sputum, milk, whole blood or any blood fraction, blood derivatives, blood cells, tumor, nervous tissues, organs or any type of tissue, any sample obtained by lavage (e.g., samples derived from the bronchi), and samples of components constituting cell cultures in vitro.

The number of an immunocyte or the expression level of a molecule expressed on the immunocyte can be measured in a biological sample isolated from a patient. In the case of using, for example, blood as the biological sample, peripheral blood is preferred. The number of an immunocyte or the expression level of a molecule expressed on the immunocyte can be measured in isolated peripheral blood. In a non-limiting aspect, the number of an immunocyte in peripheral blood isolated from the patient may be measured using, for example, giemsa-stained leukocyte fractions or an automatic blood cell counter. In another non-limiting aspect, the expression level of a molecule expressed on the immunocyte in peripheral blood isolated from the patient may be measured by, for example, flow cytometry using a specific antibody.

The term "isolated" refers to causing "artificial" change from a natural state, i.e., shifting and/or removing a naturally occurring substance from its original environment. In the present invention, the term "isolated" means that, for example, a cell, a polynucleotide or a polypeptide present in an organism is unisolated, whereas the same cell, polynucleotide or polypeptide thereas is isolated when separated from a material present with the cell, the polynucleotide or the polypeptide in a natural state. A polynucleotide or a polypeptide introduced into an organism by transformation, genetic manipulation, or any other recombination method is in an isolated state even when present in the organism (regardless of being alive or dead).

Immunocyte

In the present invention, the "immunocyte" means a cell involved in in vivo immune response, such as a leukocyte. Specific examples thereof include granulocytes (neutrophils, basophils, and eosinophils), monocytes (macrophages), lymphocytes (T cells, B cells, and NK cells), and dendritic cells.

Method for Measuring the Number of Immunocyte

In the present invention, the method for measuring the number of an immunocyte in the peripheral blood of the patient is not limited. For example, blood is collected as a biological sample from the patient, and the collected blood can be assayed as a sample using an automatic blood cell counter. Alternatively, for example, erythrocytes or leukocytes are counted using a hemacytometer, while blood cells can be stained by giemsa staining and then classified into neutrophils, eosinophils, basophils, monocytes, and lymphocytes depending on the difference in staining pattern or shape. The respective numbers of these cells can be calculated from the ratios thereof. In this context, the biological sample to be collected is not limited as long as the sample permits assay for patient-derived immunocytes. Examples thereof include peripheral blood. Specifically, the assay may be conducted by a method described in, for example, Examples.

Method for Measuring Expression Level of Molecule Expressed on Immunocyte

In the present invention, the method for measuring the expression level of a molecule expressed on the immunocyte of the patient is not limited. For example, blood can be collected as a biological sample from the patient, then reacted with an antibody specific for the molecule expressed on the immunocyte, and assayed using flow cytometry or the like. In addition, molecules of equivalent soluble fluorochrome (MESF) can be set using fluorescently labeled calibration beads to convert the flow cytometry measurement value of fluorescence intensity of a cell population to an MESF value for quantification. Specifically, the expression level (MESF) can be measured according to a method described in, for example, Journal of Research of the National Institute of Standard and Technology, vol. 107, No. 4 (2002) pp. 339-353. In this context, the biological sample to be collected is not limited as long as the sample permits assay for patient-derived immunocytes. Examples thereof include peripheral blood. Specifically, the assay may be conducted by a method described in, for example, Examples.

Confirmation of Fcγ Receptor Gene Polymorphism

In the present invention, the method for confirming the presence or absence of an Fcγ receptor gene polymorphism in the patient is not limited. For example, a biological sample is collected from the patient, and the genomic gene is isolated from the collected sample. The nucleotide sequence of a gene corresponding to the Fcγ receptor can be determined to confirm the presence or absence of the polymorphism. Specifically, this assay can be conducted according to a method described in, for example, Journal of Clinical Oncology, vol. 21, No. 21 (2003) pp. 3940-3947. In this context, the biological sample to be collected is not limited as long as the sample permits obtainment of the patient-derived genomic gene. Examples thereof include peripheral blood and skin sections.

In the present invention, preferred examples of biological samples used for detecting the expression level of GPC3 in tissues include test subject-derived preparations. The test subject-derived preparation is preferably a tissue obtained from the test subject, more preferably a liver cancer or hepatocellular cancer tissue of the test subject. The liver cancer or hepatocellular cancer tissue is collected preferably using a biopsy method known in the art. The liver biopsy refers to a method of directly inserting a thin long needle into the liver from skin surface and collecting liver tissues. The needling site is typically the intercostal space of the right lower chest. The safety of the needling site is confirmed before operation using an ultrasonic examination apparatus. Then, the needling site is disinfected. A region from the skin to the surface of the liver is subjected to anesthesia. After small incision of the skin at the needling site, a puncture needle is inserted thereto.

For microscopic observation by transmitted beams, the tissue preparation is sliced to a degree that allows beams of light for use in the microscope to sufficiently penetrate the tissue slice. At a stage prior to the slicing, the tissue preparation is fixed. Specifically, proteins in tissues or cells are coagulated by dehydration or denaturation to thereby rapidly kill the cells constituting the tissues. The resulting structure is stabilized and insolubilized. First, the tissue preparation to be fixed is cut into a fragment with a size and a shape suitable for the preparation of paraffin-embedded sections by use of a knife such as a surgical knife. Subsequently, the fragment is dipped in a fixative, which is a reagent used for carrying out fixation. Formalin, more preferably neutral buffered formalin, is preferably used as the fixative. The concentration of the neutral buffered formalin is appropriately selected according to the characteristics or physical properties of the tissue preparation. The concentration used may be appropriately changed between 1 and 50%, preferably 5 and 25%, more preferably 10 and 15%. The fixative with the tissue preparation dipped therein is appropriately degassed using a vacuum pump. For fixation, the tissue preparation is left for several hours in the fixative under conditions of ordinary pressure and room temperature. The time required for the fixation can be appropriately selected within the range of 1 hour to 7 days, preferably 2 hours to 3 days, more preferably 3 hours to 24 hours, further preferably 4 hours to 16 hours. The tissue preparation thus fixed is appropriately dipped in a phosphate buffer solution or the like for additional several hours (which can be appropriately selected within the range of 2 hours to 48 hours, preferably 3 hours to 24 hours, more preferably 4 hours to 16 hours).

Next, sections can be preferably prepared by freeze sectioning or paraffin sectioning from the tissue preparation thus fixed. Preferred examples of the freeze sectioning include a method which involves adding tissues into O.C.T. Compound (Miles Inc.), freezing the mixture, and slicing the frozen mixture using a cryostat (frozen section preparation apparatus). In the paraffin sectioning, the fixed tissue preparation is dipped in an embedding agent, which is then solidified to thereby impart thereto uniform and appropriate hardness. Paraffin can be preferably used as the embedding agent. The fixed tissue preparation is dehydrated using ethanol. Specifically, the tissue preparation is dipped in 70% ethanol, 80% ethanol, and 100% ethanol in this order and thereby dehydrated. The time required for the dipping and the number of runs can be appropriately selected within the ranges of 1 hour to several days and 1 to 3 times, respectively. The tissue preparation may be dipped therein at room temperature or 4° C. In the case of dipping at 4° C., a longer dipping time (e.g., overnight) is more preferred. After replacement of the liquid phase with xylene, the tissue preparation is embedded in paraffin. The time required for the replacement of the liquid phase with xylene can be appropriately selected within the range of 1 hour to several hours. This replacement may be performed at room temperature or 4° C. In the case of replacement at 4° C., a longer replacement time (e.g., overnight) is more preferred. The time required for the embedding in paraffin and the number of runs can be appropriately selected within the ranges of 1 hour to several hours and 1 to 4 times, respectively. This embedding may be performed at room temperature or 4° C. In the case of embedding at 4° C., a longer embedding time (e.g., overnight) is more preferred. Alternatively, the tissue preparation may be preferably embedded in paraffin using paraffin embedding apparatus (EG1160, Leica, etc.) that automatically performs paraffin embedding reaction.

The tissue preparation thus paraffin-embedded is bonded to a block base to prepare a "block". This block is sliced into the desired thickness selected from thicknesses of 1 to 20 μm by use of a microtome. The sliced tissue section is left standing on a glass slide as a permeable support and thereby fixed thereon. In this case, the glass slide coated with 0.01% poly-L-lysine (Sigma-Aldrich Corp.) and then dried may be preferably used in order to prevent the tissue section from coming off. The fixed tissue section is dried in air for an appropriate time selected from between several minutes and 1 hour.

Epitope Retrieval

In a preferred aspect, an epitope in an antigen whose reactivity with an antibody has been attenuated due to formalin fixation is retrieved. In the present invention, protease-induced epitope retrieval (PIER) or heat-induced epitope retrieval (HIER) may be applied to the retrieval. In a non-limiting aspect, PIER may be applied to one of "two identifiable tissue preparations" prepared as shown below, while HIER may be applied to the other preparation. In this case, a difference in the degree of staining between these preparations reacted with antibodies can be digitized.

In a non-limiting aspect, a set of two tissue preparations is prepared, which are prepared as shown in the paragraph "Biological sample" and attached onto permeable supports. The tissue preparations are desirably two histologically identifiable tissue preparations. The term "identifiable" means that two tissue preparations to be mutually compared are composed of substantially the same cells or tissues in test subject-derived preparations serving as origins of the tissue preparations. For example, two tissue preparations prepared as adjacent sections correspond to two identifiable tissue preparations. In the present invention as well, the "two identifiable tissue preparations" refer to two tissue preparations prepared as adjacent sections, unless otherwise specified. In addition, two tissue preparations composed of cells or tissues structurally identifiable between the preparations correspond to "two identifiable tissue preparations", even if the tissue preparations are not prepared as adjacent sections. Preferred examples of such two tissue preparations composed of cells or tissues structurally identifiable therebetween include (1) tissue sections containing cells derived from the same cells at the same positions on plane coordinates in the sections, and (2) tissue sections in which at least 50% or more, preferably 60% or more, more preferably 70% or more, further preferably 80% or more, still further preferably 90% or more, particularly preferably 95% or more of the cells are present at the same positions on the plane coordinates.

The heat-induced epitope retrieval appropriately employs, for example, a heating method using microwave, a heating method using an autoclave, or a heating method using boiling treatment. In the case of boiling treatment at an output of 780 W so as to keep a liquid temperature at approximately 98° C., the time required for the retrieval including the treatment is appropriately selected from between 5 minutes and 60 minutes and is, for example, 10 minutes. The epitope retrieval treatment can be performed in a 10 mM sodium citrate buffer solution as well as commercially available Target Retrieval Solution (DakoCytomation), for example. Target Retrieval Solution is used in Examples described below. Any buffer solution or aqueous solution is preferably used as long as an epitope in the antigen that is recognized by an anti-GPC3 antibody acquires the ability to bind to the antibody as a result of the retrieval treatment so that an antigen-antibody complex mentioned later can be detected.

The protease for use in the protease-induced epitope retrieval is not limited by its type or origin. Generally available protease can be appropriately selected for use. Preferred examples of the protease used include pepsin with 0.05% concentration in 0.01 N hydrochloric acid, trypsin with 0.1% concentration further containing $CaCl_2$ with 0.01% concentration in a tris buffer solution (pH 7.6), and protease K with a concentration of 1 to 50 μg/ml in a 10 mM tris-HCl buffer solution (pH 7.8) containing 10 mM EDTA and 0.5% SDS. In the case of using protease K, the pH of the reaction solution is appropriately selected from between 6.5 and 9.5, and an SH reagent, a trypsin inhibitor, or a chymotrypsin inhibitor may be appropriately used. Specific examples of such preferred protease also include protease attached to Histofine HER2 kit (MONO) (Nichirei Biosciences Inc.). The protease-induced epitope retrieval is usually performed at 37° C. The reaction temperature may be appropriately changed within the range of 25° C. to 50° C. The reaction time of the protease-induced epitope retrieval performed at 37° C. is appropriately selected from between, for example, 1 minute and 5 hours and is, for example, 15 minutes, 30 minutes, 45 minutes, 1 hour, 2 hours, 3 hours, or 4 hours. After the completion of the retrieval treatment, the tissue preparation thus treated is washed with a washing buffer solution. Phosphate-buffered saline (PBS) is preferably used as the washing buffer solution. Alternatively, a tris-HCl buffer solution may be preferably used. The washing conditions adopted in this method usually involve three runs of washing at room temperature for 5 minutes. The washing time and temperature may be appropriately changed.

Reaction Between Tissue Preparation and Anti-GPC3 Antibody

The tissue preparation thus treated by the heat-induced epitope retrieval and/or the tissue preparation thus treated by the protease-induced epitope retrieval are reacted with an anti-GPC3 antibody mentioned later as a primary antibody. The reaction is carried out under conditions appropriate for the recognition of an epitope in the antigen by the anti-GPC3 antibody and the subsequent formation of an antigen-antibody complex. The reaction is usually carried out overnight at 4° C. or at 37° C. for 1 hour. The reaction conditions may be appropriately changed within a range appropriate for the recognition of an epitope in the antigen by the antibody and the subsequent formation of an antigen-antibody complex. For example, the reaction temperature may be changed within the range of 4° C. to 50° C., while the reaction time may be changed between 1 minute and 7 days. A longer reaction time is more preferred for the reaction carried out at a low temperature. After the completion of the primary antibody reaction, each tissue preparation is washed with a washing buffer solution. Phosphate-buffered saline (PBS) is preferably used as the washing buffer solution. Alternatively, a tris-HCl buffer solution may be preferably used. The washing conditions adopted in this method usually involve three runs of washing at room temperature for 5 minutes. The washing time and temperature may be appropriately changed.

Subsequently, each tissue preparation thus reacted with the primary antibody is reacted with a secondary antibody that recognizes the primary antibody. A secondary antibody labeled in advance with a labeling material for visualizing the secondary antibody is usually used. Preferred examples of the labeling material include: fluorescent dyes such as fluorescein isothiocyanate (FITC), Cy2 (Amersham Biosciences Corp.), and Alexa 488 (Molecular Probes Inc.); enzymes such as peroxidase and alkaline phosphatase; and gold colloid.

The reaction with the secondary antibody is carried out under conditions appropriate for the formation of an antigen-antibody complex between the anti-GPC3 antibody and the secondary antibody that recognizes the anti-GPC3 antibody. The reaction is usually carried out at room temperature or 37° C. for 30 minutes to 1 hour. The reaction conditions may be appropriately changed within a range appropriate for the formation of an antigen-antibody complex between the anti-GPC3 antibody and the secondary antibody. For example, the reaction temperature may be changed within the range of 4° C. to 50° C., while the reaction time may be changed between 1 minute and 7 days. A longer reaction time is more preferred for the reaction carried out at a low temperature. After the completion of the secondary antibody reaction, each tissue preparation is washed with a washing buffer solution. Phosphate-buffered saline (PBS) is preferably used as the washing buffer solution. Alternatively, a tris-HCl buffer solution may be preferably used. The washing conditions adopted in this method usually involve three runs of washing at room temperature for 5 minutes. The washing time and temperature may be appropriately changed.

Next, each tissue preparation thus reacted with the secondary antibody is reacted with a substance capable of visualizing the labeling material. When peroxidase is used as the labeling material in the secondary antibody, a 0.02% aqueous hydrogen peroxide solution and a diaminobenzidine (DAB) solution concentration-adjusted to 0.1% with a 0.1 M tris-HCl buffer solution (pH 7.2) are mixed in equal amounts immediately before incubation and the tissue preparation is incubated in the resulting reaction solution. A chromogenic substrate such as DAB-Ni or AEC+ (both from Dako Japan Inc.) may be appropriately selected instead of DAB. During the course of incubation, the visualization reaction can be stopped by the dipping of the tissue preparation in PBS at the stage where appropriate color development is confirmed by the occasional microscopic observation of the degree of color development.

When alkaline phosphatase is used as the labeling material in the secondary antibody, each tissue preparation is incubated in a 5-bromo-4-chloro-3-indolyl phosphoric acid (BCIP)/nitro blue tetrazolium (NBT) (Zymed Laboratories, Inc.) substrate solution (solution of NBT and BCIP dissolved at concentrations of 0.4 mM and 0.38 mM, respectively, in a 50 mM sodium carbonate buffer solution (pH 9.8) containing 10 mM $MgCl_2$ and 28 mM NaCl). Alternatively, for example, Permanent Red, Fast Red, or Fuchsin+(all from Dako Japan Inc.) may be appropriately used instead of BCIP and NBT. Prior to the incubation, the tissue preparation may be preincubated at room temperature for 1 minute to several hours with a 0.1 M tris-HCl buffer solution (pH 9.5) containing levamisole chloride (Nacalai Tesque, Inc.), an inhibitor of endogenous alkaline phosphatase, with a concentration of 1 mM, 0.1 M sodium chloride, and 50 mM magnesium chloride. During the course of incubation, the tissue preparation is washed with water or with TBST (TBS containing 0.1% Tween 20) after stop of the reaction by the addition of TBS containing 2% polyvinyl alcohol, at the stage where the deposition of a final reaction product purple formazan is confirmed by occasional microscopic observation. When gold colloid is used as the label in the secondary antibody, metallic silver is attached to gold particles by silver intensification to thereby visualize the gold colloid. The silver intensification method is generally known to those skilled in the art.

When a fluorescent dye such as fluorescein isothiocyanate (FITC), Cy2 (Amersham Biosciences Corp.), or Alexa 488 (Molecular Probes Inc.) is used as the labeling material in the secondary antibody, the reaction step of the visualizing substance is unnecessary. Each tissue preparation is irradiated with light at an excitation wavelength for the fluorescent material. Emitted light can be appropriately detected using a fluorescence microscope.

Immunohistochemical Staining Score

In a non-limiting aspect, the present invention also provides a method for determining the efficacy of GPC3-targeting drug therapy or determining the continuation of GPC3-targeting drug therapy from the concentration of free GPC3 as well as the expression level of GPC3 detected in tissues by the method described above. In a non-limiting aspect, the expression of GPC3 detected in tissues by the method described above is digitized by, for example, a non-limiting method exemplified below. In the present invention, such a digitized expression level of GPC3 in tissues is referred to as an "immunohistochemical staining score of GPC3".

The respective scores of positive cell rate (PR), staining intensity of cytoplasm (SI-cp) or staining intensity of cell membrane (SI-cm), and staining pattern of cell membrane (Sp-cm) are calculated according to the criteria shown in Table 1 by a method described in WO2009116659 and added on the basis of calculation expressions 1 and 2. The resulting score is exemplified as the non-limiting immunohistochemical staining score of GPC3 (referred to as "composite score 1" for the sake of convenience) of the present invention.

TABLE 1-1

| Criterion | Evaluation | Score |
|---|---|---|
| Positive cell rate (PR) | 0 | 0 |
| | 1% or more and less than 20% | 1 |
| | 20% or more and less than 50% | 2 |
| | 50% or more | 3 |
| Staining intensity (SI) Cytoplasm (SI-cp) Cell membrane (SI-cm) | Slightly positive | 0 |
| | Weakly positive | 1 |
| | Moderately positive and/or weakly positive with strong positivity | 2 |
| | Moderately positive | 3 |
| | Strongly positive | 4 |

TABLE 1-1-continued

| Criterion | Evaluation | Score |
|---|---|---|
| Staining pattern of cell membrane (SP-cm) | Negative | 0 |
| | When only a portion of the cell membranes of cells was stained | 1 |
| | When a portion of the cell membranes of most of these cells was stained and the cell membranes of some of the cells were circumferentially stained | 2 |
| | When the cell membranes of most of these cells were circumferentially stained | 3 |

(Sp-cm scores were calculated by the evaluation of cell staining in the visual field under microscope using an objective lens with a magnification of 4 or 10.)

IHC total=PR+SI-Cp+SI-Cm+Sp-Cm      Expression 1

IHC cm=PR+SI-Cm+Sp-Cm      Expression 2

TABLE 1-2

| Composite score 1 | IHC total score |
|---|---|
| High expression | 7 or higher |
| Low or moderate expression | Lower than 7 |

In addition, the H-score is known (literature: KS. McCarty Jr. et al., Use of a monoclonal anti-Estrogen receptor antibody in the immunohistochemical evaluation of human tumors. Cancer Res. Suppl. (1986) 46, 4244s-4248s), which is calculated on the basis of the proportion of cells that exhibit each staining intensity (staining intensity of cell membrane or cytoplasm) classified into 0 to 3.

Another example of the immunohistochemical staining score includes the following scoring algorithm for classification of 0 to 3+ on the basis of the staining intensity of membrane, the staining intensity of cytoplasm, and the degree of staining, and an evaluation score based on the algorithm (composite score 2).

TABLE 2

| Score (Composite score 2) | Evaluation |
|---|---|
| 0 | When cell membranes were not stained |
| | When less than 10% of tumor cells exhibited intracytoplasmic staining |
| 1+ | When less than 10% of tumor cells exhibited cell membrane staining |
| | and/or |
| | When 10% or more of tumor cells exhibited intracytoplasmic staining (note that strong intracytoplasmic staining, if any, remains at less than 50% of the tumor cells) |
| 2+ | When 10% or more of tumor cells exhibited weak or moderate cell membrane staining (note that strong cell membrane staining, if any, remains at less than 10% of the tumor cells) regardless of the presence or absence of intracytoplasmic staining in 10% or more of the tumor cells (note that intracytoplasmic staining, if any, remains at less than 50% of the tumor cells) |
| 3+ | When 10% or more of tumor cells exhibited strong cell membrane staining regardless of the presence or absence of intracytoplasmic staining |
| | or |
| | When 50% or more of tumor cells exhibited strong intracytoplasmic staining |

In the present invention, for example, the composite score 1, the H-score, and the composite score 2 may be used alone or in combination as the "immunohistochemical staining score of GPC3". In a non-limiting aspect, the composite score 1 may be used as the "immunohistochemical staining score of GPC3". In another non-limiting aspect, the composite score 2 may be used as the "immunohistochemical staining score of GPC3".

GPC3-Targeting Drug

In the present invention, the term "GPC3-targeting drug" refers to every molecule that blocks, suppresses, inhibits, or reduces the biological activity of GPC3 including a signal pathway mediated by GPC3 or is cytotoxic to cells expressing GPC3. The term "targeting treatment" does not suggest a certain mechanism having biological effects and conceptually includes every possible effect of the pharmacological, physiological, and biochemical interactions of GPC3. Examples of the GPC3-targeting drug include: (1) antagonistic or non-antagonistic inhibitors of the binding of GPC3 to a GPC3-binding ligand, i.e., active substances that interfere with the binding of GPC3 to its ligand; (2) active substances that do not interfere with the binding of GPC3 to its ligand but instead inhibit or decrease activity brought about by the binding of GPC3 to its ligand; (3) active substances that decrease GPC3 expression; and (4) active substances capable of eliciting cytotoxic activity against cells expressing GPC3. In a non-limiting aspect, examples of the ligand can include wnt (Cancer Res. (2005) 65, 6245-6254), IGF-II (Carcinogenesis (2008) 29 (7), 1319-1326), and fibroblast growth factor 2 (Int. J. Cancer (2003) 103 (4), 455-465). In a non-limiting aspect, such active substances can include, for example, antibodies (including their antigen-binding domains), nucleic acid molecules (antisense or RNAi molecules, etc.), peptides, non-peptidic low-molecular-weight organic materials.

In a non-limiting aspect, examples of the non-peptidic low-molecular-weight organic material that may be used as the GPC3-targeting drug of the present invention include non-peptidic low-molecular-weight quinoline derivatives (WO2008/046085) which act on methylation suppressor genes. Further examples thereof can include HLA-A2-restricted GPC3 peptide 144-152 (SEQ ID NO: 2) and HLA-A24-restricted GPC3 peptide 298-306 (SEQ ID NO: 3) (Clin. Cancer Res. (2006) 12 (9), 2689-2697) which elicit the cytotoxic activity of cytotoxic T cells.

Anti-GPC3 Antibody

In a non-limiting aspect, examples of the anti-GPC3 antibody that may be used as the GPC3-targeting drug of the present invention can include an antibody-drug conjugate (ADC) (WO2007/137170) comprising a 1G12 antibody (WO2003/100429) (sold under catalog No. B0134R by BioMosaics Inc.) conjugated with a cytotoxic substance.

In an alternative non-limiting aspect, examples of the anti-GPC3 antibody include a humanized anti-GPC3 antibody described in WO2006/006693 or WO2009/041062. Specifically, a humanized anti-GPC3 antibody comprising heavy chain CDR1, heavy chain CDR2, and heavy chain CDR3 represented by SEQ ID NOs: 4, 5, and 6, respectively, and light chain CDR1, light chain CDR2, and light chain CDR3 represented by SEQ ID NOs: 7, 8, and 9, respectively, can be used as the GPC3-targeting drug of the present invention. The humanized anti-GPC3 antibody can be prepared using, as templates for humanization, appropriately selected human framework sequences having high sequence identity to a heavy chain framework sequence represented by SEQ ID NO: 10 or a light chain framework sequence represented by SEQ ID NO: 11.

In a further alternative non-limiting aspect, an anti-GPC3 chimeric antibody or a humanized anti-GPC3 antibody comprising heavy chain CDR1, heavy chain CDR2, and heavy chain CDR3 represented by SEQ ID NOs: 12, 13, and 14, respectively, and light chain CDR1, light chain CDR2, and light chain CDR3 represented by SEQ ID NOs: 15, 16, and 17, respectively, can be used as the GPC3-targeting drug of the present invention. The humanized anti-GPC3 antibody can be prepared using, as templates for humanization, appropriately selected human framework sequences having high sequence identity to a heavy chain framework sequence represented by SEQ ID NO: 18 or a light chain framework sequence represented by SEQ ID NO: 19.

In an alternative non-limiting aspect, an anti-GPC3 chimeric antibody or a humanized anti-GPC3 antibody comprising heavy chain CDR1, heavy chain CDR2, and heavy chain CDR3 represented by SEQ ID NOs: 20, 21, and 22, respectively, and light chain CDR1, light chain CDR2, and light chain CDR3 represented by SEQ ID NOs: 23, 24, and 25, respectively, can be used as the GPC3-targeting drug of the present invention. The humanized anti-GPC3 antibody can be prepared using, as templates for humanization, appropriately selected human framework sequences having high sequence identity to a heavy chain framework sequence represented by SEQ ID NO: 26 or a light chain framework sequence represented by SEQ ID NO: 27.

In a further alternative non-limiting aspect, an anti-GPC3 chimeric antibody or a humanized anti-GPC3 antibody comprising heavy chain CDR1, heavy chain CDR2, and heavy chain CDR3 represented by SEQ ID NOs: 28, 29, and 30, respectively, and light chain CDR1, light chain CDR2, and light chain CDR3 represented by SEQ ID NOs: 31, 32, and 33, respectively, can be used as the GPC3-targeting drug of the present invention. The humanized anti-GPC3 antibody can be prepared using, as templates for humanization, appropriately selected human framework sequences having high sequence identity to a heavy chain framework sequence represented by SEQ ID NO: 34 or a light chain framework sequence represented by SEQ ID NO: 35.

In an alternative non-limiting aspect, an anti-GPC3 chimeric antibody or a humanized anti-GPC3 antibody comprising heavy chain CDR1, heavy chain CDR2, and heavy chain CDR3 represented by SEQ ID NOs: 36, 37, and 38, respectively, and light chain CDR1, light chain CDR2, and light chain CDR3 represented by SEQ ID NOs: 39, 40, and 41, respectively, can be used as the GPC3-targeting drug of the present invention. The humanized anti-GPC3 antibody can be prepared using, as templates for humanization, appropriately selected human framework sequences having high sequence identity to a heavy chain framework sequence represented by SEQ ID NO: 42 or a light chain framework sequence represented by SEQ ID NO: 43.

In a further alternative non-limiting aspect, a humanized anti-GPC3 antibody comprising a heavy chain variable region selected from the group of heavy chain variable regions represented by SEQ ID NOs: 44, 45, 46, 47, 48, 49, and 50 and a light chain variable region represented by SEQ ID NO: 51 can be used as the GPC3-targeting drug of the present invention. In a further alternative non-limiting aspect, a humanized anti-GPC3 antibody comprising a heavy chain variable region selected from the group of heavy chain variable regions represented by SEQ ID NOs: 44, 45, 46, 47, 48, 49, and 50 and a light chain variable region selected from the group of light chain variable regions represented by SEQ ID NOs: 52, 53, 54, 55, 56, 57, 58, 59, 60, 61, 62, 63, 64, 65, and 66 can be used as the GPC3-targeting drug of the present invention.

In a further alternative non-limiting aspect, a humanized anti-GPC3 antibody comprising a heavy chain variable region represented by SEQ ID NO: 67 and a light chain variable region represented by SEQ ID NO: 68, a humanized anti-GPC3 antibody comprising a heavy chain variable region represented by SEQ ID NO: 69 and a light chain variable region represented by SEQ ID NO: 70, a humanized anti-GPC3 antibody comprising a heavy chain variable region represented by SEQ ID NO: 71 and a light chain variable region represented by SEQ ID NO: 72, or a humanized anti-GPC3 antibody comprising a heavy chain variable region represented by SEQ ID NO: 71 and a light chain variable region represented by SEQ ID NO: 73 can also be used as the GPC3-targeting drug of the present invention.

Cytotoxic Activity

Alternative examples of the anti-GPC3 antibody of the present invention include an anti-GPC3 antibody having cytotoxic activity. In the present invention, non-limiting examples of the cytotoxic activity include antibody-dependent cell-mediated cytotoxicity or antibody-dependent cellular cytotoxicity (ADCC) activity, complement-dependent cytotoxicity (CDC) activity, and cytotoxic activity based on T cells. In the present invention, the CDC activity means cytotoxic activity brought about by the complement system. On the other hand, the ADCC activity means the activity of damaging target cells by, for example, immunocytes, through the binding of the immunocytes via Fcγ receptors expressed on the immunocytes to the Fc regions of antigen-binding molecules comprising antigen-binding domains capable of binding to membrane molecules expressed on the cell membranes of the target cells. Whether or not the antigen-binding molecule of interest has ADCC activity or has CDC activity can be determined by a method known in the art (e.g., Current protocols in Immunology, Chapter 7. Immunologic studies in humans, Coligan et al., ed. (1993)).

Specifically, effector cells, a complement solution, and target cells are first prepared.

(1) Preparation of Effector Cells

The spleens are excised from CBA/N mice or the like, and spleen cells are separated therefrom in an RPMI1640 medium (Invitrogen Corp.). The spleen cells can be washed with this medium containing 10% fetal bovine serum (FBS, HyClone Laboratories, Inc.) and then concentration-adjusted to $5 \times 10^6$ cells/mL to prepare the effector cells.

(2) Preparation of Complement Solution

Baby Rabbit Complement (CEDARLANE Laboratories Ltd.) can be diluted 10-fold with a medium (Invitrogen Corp.) containing 10% FBS to prepare the complement solution.

(3) Preparation of Target Cells

Antigen-expressing cells can be cultured at 37° C. for 1 hour, together with 0.2 mCi $^{51}$Cr-sodium chromate (GE Healthcare Bio-Sciences Corp.), in a DMEM medium containing 10% FBS to thereby radiolabel the target cells. The cells thus radiolabeled can be washed three times with an RPMI1640 medium containing 10% FBS and then concentration-adjusted to $2 \times 10^5$ cells/mL to prepare the target cells.

The ADCC or CDC activity can be assayed by a method described below. For the ADCC activity assay, the target cells and the antigen-binding molecule (each 50 μl/well) are added to a U-bottom 96-well plate (Becton, Dickinson and Company) and reacted for 15 minutes on ice. Then, 100 μl of the effector cells is added to each well, and the plate is left standing for 4 hours in a $CO_2$ incubator. The final concentration of the antibody (antigen-binding molecule) can be set to, for example, 0 or 10 μg/ml. The radioactivity of 100 μl of the supernatant recovered from each well of the plate thus left standing is measured using a gamma counter (COBRA II AUTO-GAMMA, MODEL D5005, Packard Instrument Company). The cytotoxic activity (%) can be calculated on the basis of the calculation expression (A–C)/(B–C)×100 using the measurement value, wherein A represents radioactivity (cpm) from each sample; B represents radioactivity (cpm) from a sample supplemented with 1% NP-40 (Nacalai Tesque, Inc.); and C represents radioactivity (cpm) from a sample containing only the target cells.

For the CDC activity assay, the target cells and the antigen-binding molecule (each 50 µl/well) are added to a flat-bottomed 96-well plate (Becton, Dickinson and Company) and reacted for 15 minutes on ice. Then, 100 µl of the complement solution is added to each well, and the plate is left standing for 4 hours in a $CO_2$ incubator. The final concentration of the antibody (antigen-binding molecule) can be set to, for example, 0 or 3 µg/ml. The radioactivity of 100 µl of the supernatant recovered from each well of the plate thus left standing is measured using a gamma counter. The cytotoxic activity based on the CDC activity can be calculated in the same way as in the ADCC activity assay.

Cytotoxic Substance

In a non-limiting aspect, alternative examples of the anti-GPC3 antibody of the present invention include an anti-GPC3 antibody conjugated with a cytotoxic substance. Such an anti-GPC3 antibody-drug conjugate (ADC) is specifically disclosed in, for example, WO2007/137170, though the conjugate of the present invention is not limited to those described therein. Specifically, the cytotoxic substance may be any of chemotherapeutic agents listed below or may be a compound disclosed in Alley et al. (Curr. Opin. Chem. Biol. (2010) 14, 529-537) or WO2009/140242. Antigen-binding molecules are conjugated with these compounds via appropriate linkers or the like.

Examples of chemotherapeutic agents that may be conjugated to the anti-GPC3 antibody of the present invention can include the following: azaribine, anastrozole, azacytidine, bleomycin, bortezomib, bryostatin-1, busulfan, camptothecin, 10-hydroxycamptothecin, carmustine, Celebrex, chlorambucil, cisplatin, irinotecan, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin, ethinyl estradiol, estramustine, etoposide, etoposide glucuronide, floxuridine, fludarabine, flutamide, fluorouracil, fluoxymesterone, gemcitabine, hydroxyprogesterone caproate, hydroxyurea, idarubicin, ifosfamide, leucovorin, lomustine, maytansinoid, mechlorethamine, medroxyprogesterone acetate, megestrol acetate, melphalan, mercaptopurine, methotrexate, mitoxantrone, mithramycin, mitomycin, mitotane, phenylbutyrate, prednisone, procarbazine, paclitaxel, pentostatin, semustine, streptozocin, tamoxifen, taxanes, Taxol, testosterone propionate, thalidomide, thioguanine, thiotepa, teniposide, topotecan, uracil mustard, vinblastine, vinorelbine, and vincristine.

In the present invention, a preferred chemotherapeutic agent is a low-molecular-weight chemotherapeutic agent. The low-molecular-weight chemotherapeutic agent is unlikely to interfere with the functions of the anti-GPC3 antibody even after forming the anti-GPC3 antibody-drug conjugate of the present invention. In the present invention, the low-molecular-weight chemotherapeutic agent has a molecular weight of usually 100 to 2000, preferably 200 to 1000. All of the chemotherapeutic agents listed herein are low-molecular-weight chemotherapeutic agents. These chemotherapeutic agents according to the present invention include prodrugs that are converted to active chemotherapeutic agents in vivo. The prodrugs may be activated through enzymatic conversion or nonenzymatic conversion.

Alternative examples of the conjugated cytotoxic substance in the anti-GPC3 antibody-drug conjugate of the present invention can include toxic peptides (toxins) such as *Pseudomonas* exotoxin A, saporin-s6, diphtheria toxin, and cnidarian toxin, radioiodine, and photosensitizers. Examples of the toxic peptides preferably include the following: diphtheria toxin A chain (Langone et al., Methods in Enzymology (1983) 93, 307-308); *Pseudomonas* exotoxin (Nature Medicine (1996) 2, 350-353); ricin A chain (Fulton et al., J. Biol. Chem. (1986) 261, 5314-5319; Sivam et al., Cancer Res. (1987) 47, 3169-3173; Cumber et al., J. Immunol. Methods (1990) 135, 15-24; Wawrzynczak et al., Cancer Res. (1990) 50, 7519-7562; and Gheeite et al., J. Immunol. Methods (1991) 142, 223-230); deglycosylated ricin A chain (Thorpe et al., Cancer Res. (1987) 47, 5924-5931); abrin A chain (Wawrzynczak et al., Br. J. Cancer (1992) 66, 361-366; Wawrzynczak et al., Cancer Res. (1990) 50, 7519-7562; Sivam et al., Cancer Res. (1987) 47, 3169-3173; and Thorpe et al., Cancer Res. (1987) 47, 5924-5931); gelonin (Sivam et al., Cancer Res. (1987) 47, 3169-3173; Cumber et al., J. Immunol. Methods (1990) 135, 15-24; Wawrzynczak et al., Cancer Res., (1990) 50, 7519-7562; and Bolognesi et al., Clin. exp. Immunol. (1992) 89, 341-346); pokeweed anti-viral protein from seeds (PAP-s) (Bolognesi et al., Clin. exp. Immunol. (1992) 89, 341-346); bryodin (Bolognesi et al., Clin. exp. Immunol. (1992) 89, 341-346); saporin (Bolognesi et al., Clin. exp. Immunol. (1992) 89, 341-346); momordin (Cumber et al., J. Immunol. Methods (1990) 135, 15-24; Wawrzynczak et al., Cancer Res. (1990) 50, 7519-7562; and Bolognesi et al., Clin. exp. Immunol. (1992) 89, 341-346); momorcochin (Bolognesi et al., Clin. exp. Immunol. (1992) 89, 341-346); dianthin 32 (Bolognesi et al., Clin. exp. Immunol. (1992) 89, 341-346); dianthin 30 (Stirpe F., Barbieri L., FEBS letter (1986) 195, 1-8); modeccin (Stirpe F., Barbieri L., FEBS letter (1986) 195, 1-8); viscumin (Stirpe F., Barbieri L., FEBS letter (1986) 195, 1-8); volkensin (Stirpe F., Barbieri L., FEBS letter (1986) 195, 1-8); dodecandrin (Stirpe F., Barbieri L., FEBS letter (1986) 195, 1-8); tritin (Stirpe F., Barbieri L., FEBS letter (1986) 195, 1-8); luffin (Stirpe F., Barbieri L., FEBS letter (1986) 195, 1-8); and trichokirin (Casellas et al., Eur. J. Biochem. (1988) 176, 581-588; and Bolognesi et al., Clin. exp. Immunol., (1992) 89, 341-346).

In the case of assaying the cytotoxic activity of the anti-GPC3 antibody-drug conjugate of the present invention, the target cells and the anti-GPC3 antibody-drug conjugate (each 50 µl/well) are added to a flat-bottomed 96-well plate (Becton, Dickinson and Company) and reacted for 15 minutes on ice. The plate is incubated for 1 to 4 hours in a $CO_2$ incubator. The anti-GPC3 antibody-drug conjugate can be appropriately used at a final concentration ranging from 0 to 3 µg/ml. After the culture, 100 µl of the supernatant is recovered from each well, and the radioactivity of the supernatant is measured using a gamma counter. The cytotoxic activity can be calculated in the same way as in the ADCC activity assay.

Fc Region

An Fc region contained in a constant region contained in the anti-GPC3 antibody of the present invention may be obtained from human IgG, though the Fc region of the present invention is not limited by a particular subclass of IgG. The Fc region refers to an antibody heavy chain constant region comprising a hinge region and CH2 and CH3 domains from the hinge region N terminus which is a papain cleavage site (about amino acid 216 based on the EU numbering). Preferred examples of the Fc region include Fc regions having binding activity against Fcγ receptors as mentioned later. In a non-limiting aspect, examples of such Fc regions include Fc regions contained in constant regions represented by SEQ ID NO: 74 for human IgG1, SEQ ID NO: 75 for IgG2, SEQ ID NO: 76 for IgG3, and SEQ ID NO: 77 for IgG4.

Fcγ Receptor (FcγR)

The Fcγ receptor (also referred to as FcγR) refers to a receptor capable of binding to the Fc region of an IgG1, IgG2, IgG3, or IgG4 monoclonal antibody and substantially means even any member of protein family encoded by Fcγ receptor genes. In humans, this family includes, but not limited to: FcγRI (CD64) including isoforms FcγRIa, FcγRIb, and FcγRIc; FcγRII (CD32) including isoforms FcγRIIa (including allotypes H131 and R131; i.e., FcγRIIa (H) and FcγRIIa (R)), FcγRIIb (including FcγRIIb-1 and FcγRIIb-2), and FcγRIIc; FcγRIII (CD16) including isoforms FcγRIIIa (including allotypes V158 and F158; i.e., FcγRIIIa (V) and FcγRIIIa (F)) and FcγRIIIb (including allotypes FcγRIIIb-NA1 and FcγRIIIb-NA2); and even any unfound human FcγR or FcγR isoform or allotype. FcγR includes human, mouse, rat, rabbit, and monkey Fcγ receptors. The FcγR of the present invention is not limited to these receptors and may be derived from any organism. The mouse FcγR includes, but not limited to, FcγRI (CD64), FcγRII (CD32), FcγRIII (CD16), and FcγRIII-2 (FcγRIV, CD16-2), and even any unfound mouse FcγR or FcγR isoform or allotype. Preferred examples of such Fcγ receptors include human FcγRI (CD64), FcγRIIa (CD32), FcγRIIb (CD32), FcγRIIIa (CD16), and/or FcγRIIIb (CD16). The polypeptide sequence of human FcγRI is described in SEQ ID NO: 78 (NP 000557.1); the polypeptide sequence of human FcγRIIa (allotype H131) is described in SEQ ID NO: 79 (AAH20823.1) (allotype R131 has a sequence with substitution by Arg at amino acid 166 in SEQ ID NO: 79); the polypeptide sequence of FcγRIIb is described in SEQ ID NO: 80 (AAI46679.1); the polypeptide sequence of FcγRIIIa is described in SEQ ID NO: 81 (AAH33678.1); and the polypeptide sequence of FcγRIIIb is described in SEQ ID NO: 82 (AAI28563.1) (registration numbers of a database such as RefSeq are shown within the parentheses). Whether or not the Fcγ receptor has binding activity against the Fc region of an IgG1, IgG2, IgG3, or IgG4 monoclonal antibody can be confirmed by a method known in the art such as FACS or ELISA formats as well as BIACORE method using amplified luminescent proximity homogeneous assay (ALPHA) screening or surface plasmon resonance (SPR) phenomena (Proc. Natl. Acad. Sci. U.S.A. (2006) 103 (11), 4005-4010).

In FcγRI (CD64) including isoforms FcγRIa, FcγRIb, and FcγRIc and FcγRIII (CD16) including isoforms FcγRIIIa (including allotypes V158 and F158) and FcγRIIIb (including allotypes FcγRIIIb-NA1 and FcγRIIIb-NA2), an α chain capable of binding to the IgG Fc region associates with a common γ chain having ITAM that transduces activating signals into cells. On the other hand, FcγRII (CD32) including isoforms FcγRIIa (including allotypes H131 and R131) and FcγRIIc contains ITAM in its cytoplasmic domain. These receptors are expressed in many immunocytes, such as macrophages, mast cells, and antigen-displaying cells. These receptors bind to IgG Fc regions and thereby transduce activating signals, which in turn promote the phagocytic capacity of macrophages, the production of inflammatory cytokines, the degranulation of mast cells, and the increased function of antigen-displaying cells. The Fcγ receptors that are able to transduce activating signals as described above are referred to as active Fcγ receptors herein.

On the other hand, FcγRIIb (including FcγRIIb-1 and FcγRIIb-2) contains ITIM that transduces inhibitory signals, in its intracytoplasmic domain. In B cells, activating signals from B cell receptors (BCRs) are inhibited by the cross-linking of BCR with FcγRIIb, resulting in the suppressed antibody production of BCR. The phagocytic capacity of macrophages or their ability to produce inflammatory cytokines is suppressed by the cross-linking of FcγRIII and FcγRIIb. The Fcγ receptors that are able to transduce inhibitory signals as described above are referred to as inhibitory Fcγ receptors herein.

Binding Activity of Fc Region Against FcγR

As mentioned above, examples of the Fc region contained in the anti-GPC3 antibody of the present invention include Fc regions having binding activity against Fcγ receptors. In a non-limiting aspect, examples of such Fc regions include Fc regions contained in constant regions represented by SEQ ID NO: 74 for human IgG1, SEQ ID NO: 75 for IgG2, SEQ ID NO: 76 for IgG3, and SEQ ID NO: 77 for IgG4. Whether or not the Fcγ receptor has binding activity against the Fc region of an IgG1, IgG2, IgG3, or IgG4 monoclonal antibody can be confirmed by a method known in the art such as FACS or ELISA formats as well as BIACORE method using amplified luminescent proximity homogeneous assay (ALPHA) screening or surface plasmon resonance (SPR) phenomena (Proc. Natl. Acad. Sci. U.S.A. (2006) 103 (11), 4005-4010).

The ALPHA screening is carried out on the basis of the following principles according to ALPHA technology using two beads, a donor and an acceptor. Luminescence signals are detected only when these two beads are located in proximity through the biological interaction between a molecule bound with the donor bead and a molecule bound with the acceptor bead. A laser-excited photosensitizer in the donor bead converts ambient oxygen to singlet oxygen in an excited state. The singlet oxygen diffuses around the donor bead and reaches the acceptor bead located in proximity thereto to thereby cause chemiluminescent reaction in the bead, which finally emits light. In the absence of the interaction between the molecule bound with the donor bead and the molecule bound with the acceptor bead, singlet oxygen produced by the donor bead does not reach the acceptor bead. Thus, no chemiluminescent reaction occurs.

For example, a biotin-labeled anti-GPC3 antibody comprising the Fc region is bound to the donor bead, while a glutathione S transferase (GST)-tagged Fcγ receptor is bound to the acceptor bead. In the absence of a competing anti-GPC3 antibody comprising a modified Fc region, the anti-GPC3 antibody having the native Fc region interacts with the Fcγ receptor to generate signals of 520 to 620 nm. An anti-GPC3 antibody comprising an untagged modified Fc region competes with the anti-GPC3 antibody having the native Fc region for the interaction with the Fcγ receptor. Decrease in fluorescence caused as a result of the competition can be quantified to thereby determine relative binding affinity. The antibody biotinylation using sulfo-NHS-biotin or the like is known in the art. The Fcγ receptor can be tagged with GST by an appropriately adopted method which involves, for example: fusing a polynucleotide encoding the Fcγ receptor in flame with a polynucleotide encoding GST; operably ligating the resulting fusion gene with a vector; and allowing cells or the like carrying the vector to express the GST-tagged Fcγ receptor, which is then purified using a glutathione column. The obtained signals are preferably analyzed using, for example, software GRAPHPAD PRISM (GraphPad Software, Inc., San Diego) adapted to a one-site competition model based on nonlinear regression analysis.

One (ligand) of the substances between which the interaction is to be observed is immobilized on a thin gold film of a sensor chip. The sensor chip is irradiated with light from the back such that total reflection occurs at the interface between the thin gold film and glass. As a result, a site having a drop in reflection intensity (SPR signal) is formed in a portion of reflected light. The other (analyte) of the substances between which the interaction is to be observed is flowed on the surface of the sensor chip and bound to the ligand so that the mass of the immobilized ligand molecule is increased to change the refractive index of the solvent on the sensor chip surface. This change in the refractive index shifts the position of the SPR signal (on the contrary, the dissociation of the bound molecules gets the signal back to the original position). The Biacore system plots on the ordinate the amount of the shift, i.e., change in mass on the sensor chip surface, and displays time-dependent change in mass as assay data (sensorgram). Kinetics: an association rate constant (ka) and a dissociation rate constant (kd) can be determined from the curve of the sensorgram, and affinity (KD) can be determined from the ratio between these constants. Inhibition assay is also preferably used in the BIACORE method. Examples of the inhibition assay are described in Lazor et al. (Proc. Natl. Acad. Sci. U.S.A. (2006) 103 (11), 4005-4010).

Fcγ Receptor (FcγR)-Binding Modified Fc Region

In addition to the Fc regions contained in constant regions represented by SEQ ID NO: 74 for human IgG1, SEQ ID NO: 75 for IgG2, SEQ ID NO: 76 for IgG3, and SEQ ID NO: 77 for IgG4, an FcγR-binding modified Fc region having higher binding activity against Fcγ receptors than that of the Fc region of native human IgG against Fcγ receptors may be appropriately used as the Fc region contained in the anti-GPC3 antibody of the present invention. The "Fc region of native human IgG" described herein means an Fc region having a fucose-containing sugar chain as a sugar chain bound to position 297 (EU numbering) of the Fc region contained in the human IgG1, IgG2, IgG3, or IgG4 constant region represented by SEQ ID NO: 74, 75, 76, or 77. Such an FcγR-binding modified Fc region can be prepared by the amino acid modification of the native human IgG Fc region. Whether or not the FcγR-binding modified Fc region has higher binding activity against FcγR than that of the native human IgG Fc region against FcγR can be appropriately confirmed by a method known in the art such as FACS or ELISA formats as well as BIACORE method using amplified luminescent proximity homogeneous assay (ALPHA) screening or surface plasmon resonance (SPR) phenomena as described above.

In the present invention, the "modification of amino acid(s)" or "amino acid modification" of the Fc region includes modification to an amino acid sequence different from the amino acid sequence of the starting Fc region. Any Fc region can be used as the starting Fc region as long as the modified form of the starting Fc region can bind to the human Fcγ receptor in a neutral region of pH. Alternatively, an Fc region further modified from an already modified Fc region as the starting Fc region may be preferably used as the Fc region of the present invention. The starting Fc region may mean the polypeptide itself, a composition containing the starting Fc region, or an amino acid sequence encoding the starting Fc region. The starting Fc region can include Fc regions known in the art produced by recombination reviewed in the paragraph about the antibody. The starting Fc region is not limited by its origin and can be obtained from an arbitrary nonhuman animal organism or a human. Preferred examples of the arbitrary organism include an organism selected from mice, rats, guinea pigs, hamsters, gerbils, cats, rabbits, dog, goats, sheep, cattle, horses, camels, and nonhuman primates. In another aspect, the starting Fc region may be obtained from a cynomolgus monkey, a marmoset, a rhesus monkey, a chimpanzee, or a human. Preferably, the starting Fc region can be obtained from human IgG1, though the starting Fc region of the present invention is not limited by a particular class of IgG. This means that the Fc region of human IgG1, IgG2, IgG3, or IgG4 can be appropriately used as the starting Fc region. Likewise, this means herein that the Fc region of arbitrary IgG class or subclass from the arbitrary organism can be preferably used as the starting Fc region. Examples of variants of naturally occurring IgG or manipulated forms thereof are described in literatures known in the art (Curr. Opin. Biotechnol. (2009) 20 (6), 685-91; Curr. Opin. Immunol. (2008) 20 (4), 460-470; Protein Eng. Des. Sel. (2010) 23 (4), 195-202; and International Publication Nos. WO2009/086320, WO2008/092117, WO2007/041635, and WO2006/105338), though the variants or the manipulated forms of the present invention are not limited to those described therein.

Examples of the modification include one or more variations, for example, a variation that substitutes amino acid(s) in the starting Fc region by amino acid residue(s) different therefrom, the insertion of one or more amino acid residues into the amino acid sequence of the starting Fc region, and/or the deletion of one or more amino acids from the amino acid sequence of the starting Fc region. Preferably, the amino acid sequence of the Fc region thus modified comprises an amino acid sequence containing at least a nonnatural portion of the Fc region. Such a variant inevitably has less than 100% sequence identity or similarity to the starting Fc region. In a preferred embodiment, the variant has an amino acid sequence with approximately 75% to less than 100% sequence identity or similarity, more preferably approximately 80% to less than 100%, further preferably approximately 85% to less than 100%, still further preferably approximately 90% to less than 100%, most preferably approximately 95% to less than 100% sequence identity or similarity to the amino acid sequence of the starting Fc region. In a non-limiting aspect of the present invention, the starting Fc region and the FcγR-binding modified Fc region of the present invention differ by at least one amino acid. The difference in amino acid between the starting Fc region and the FcγR-binding modified Fc region of the present invention may be preferably determined by a difference in amino acid with the identified position of its amino acid residue defined particularly by the EU numbering.

The amino acid(s) in the Fc region can be modified by an appropriately adopted method known in the art such as site-directed mutagenesis (Kunkel et al., Proc. Natl. Acad. Sci. USA (1985) 82, 488-492) or overlap extension PCR. Also, a plurality of methods known in the art can be adopted as methods for modifying an amino acid to substitute the amino acid by an amino acid other than natural one (Annu. Rev. Biophys. Biomol. Struct. (2006) 35, 225-249; and Proc. Natl. Acad. Sci. U.S.A. (2003) 100 (11), 6353-6357). For example, a tRNA-containing cell-free translation system (Clover Direct (Protein Express, an R & D oriented company)) comprising a non-natural amino acid bound with an amber suppressor tRNA complementary to UAG codon (amber codon), which is a stop codon, is also preferably used.

The FcγR-binding modified Fc region (contained in the antigen-binding molecule of the present invention) having higher binding activity against Fcγ receptors than that of the native human IgG Fc region against Fcγ receptors can be obtained by any method. Specifically, the FcγR-binding modified Fc region can be obtained by the amino acid modification of a human IgG immunoglobulin Fc region used as the starting Fc region. Examples of the IgG immunoglobulin Fc region preferred for the modification include Fc regions contained in human IgG (IgG1, IgG2, IgG3, and IgG4, and modified forms thereof) constant regions represented by SEQ ID NOs: 74, 75, 76, and 77.

The modification to other amino acids can include amino acid modification at any position as long as the resulting Fc region has higher binding activity against Fcγ receptors than that of the native human IgG Fc region against Fcγ receptors. When the antigen-binding molecule contains a human IgG1 Fc region as a human Fc region, the modification preferably allows the Fc region to contain a fucose-containing sugar chain as a sugar chain bound to position 297 (EU numbering) and is effective for producing higher binding activity against Fcγ receptors than that of the native human IgG Fc region against Fcγ receptors. Such amino acid modification has been reported in, for example, International Publication Nos. WO2007/024249, WO2007/021841, WO2006/031370, WO2000/042072, WO2004/029207, WO2004/099249, WO2006/105338, WO2007/041635, WO2008/092117, WO2005/070963, WO2006/020114, WO2006/116260, and WO2006/023403.

Examples of amino acids that may undergo such modification include at least one or more amino acids selected from the group consisting of
position 221, position 222, position 223, position 224, position 225, position 227, position 228, position 230, position 231, position 232, position 233, position 234, position 235, position 236, position 237, position 238, position 239, position 240, position 241, position 243, position 244, position 245, position 246, position 247, position 249, position 250, position 251, position 254, position 255, position 256, position 258, position 260, position 262, position 263, position 264, position 265, position 266, position 267, position 268, position 269, position 270, position 271, position 272, position 273, position 274, position 275, position 276, position 278, position 279, position 280, position 281, position 282, position 283, position 284, position 285, position 286, position 288, position 290, position 291, position 292, position 293, position 294, position 295, position 296, position 297, position 298, position 299, position 300, position 301, position 302, position 303, position 304, position 305, position 311, position 313, position 315, position 317, position 318, position 320, position 322, position 323, position 324, position 325, position 326, position 327, position 328, position 329, position 330, position 331, position 332, position 333, position 334, position 335, position 336, position 337, position 339, position 376, position 377, position 378, position 379, position 380, position 382, position 385, position 392, position 396, position 421, position 427, position 428, position 429, position 434, position 436 and position 440 based on the EU numbering. The modification of these amino acids can yield the Fc region (FcγR-binding modified Fc region) having higher binding activity against Fcγ receptors than that of the native human IgG Fc region against Fcγ receptors.

Examples of particularly preferred modification for use in the present invention include at least one or more amino acid modifications selected from the group consisting of modifications of amino acid 221 to Lys or Tyr,
amino acid 222 to Phe, Trp, Glu, or Tyr,
amino acid 223 to Phe, Trp, Glu, or Lys,
amino acid 224 to Phe, Trp, Glu, or Tyr,
amino acid 225 to Glu, Lys, or Trp,
amino acid 227 to Glu, Gly, Lys, or Tyr,
amino acid 228 to Glu, Gly, Lys, or Tyr,
amino acid 230 to Ala, Glu, Gly, or Tyr,
amino acid 231 to Glu, Gly, Lys, Pro, or Tyr,
amino acid 232 to Glu, Gly, Lys, or Tyr,
amino acid 233 to Ala, Asp, Phe, Gly, His, Ile, Lys, Leu, Met, Asn, Gln, Arg, Ser, Thr, Val, Trp, or Tyr,
amino acid 234 to Ala, Asp, Glu, Phe, Gly, His, Ile, Lys, Met, Asn, Pro, Gln, Arg, Ser, Thr, Val, Trp, or Tyr,
amino acid 235 to Ala, Asp, Glu, Phe, Gly, His, Ile, Lys, Met, Asn, Pro, Gln, Arg, Ser, Thr, Val, Trp, or Tyr,
amino acid 236 to Ala, Asp, Glu, Phe, His, Ile, Lys, Leu, Met, Asn, Pro, Gln, Arg, Ser, Thr, Val, Trp, or Tyr,
amino acid 237 to Asp, Glu, Phe, His, Ile, Lys, Leu, Met, Asn, Pro, Gln, Arg, Ser, Thr, Val, Trp, or Tyr,
amino acid 238 to Asp, Glu, Phe, Gly, His, Ile, Lys, Leu, Met, Asn, Gln, Arg, Ser, Thr, Val, Trp, or Tyr,
amino acid 239 to Asp, Glu, Phe, Gly, His, Ile, Lys, Leu, Met, Asn, Pro, Gln, Arg, Thr, Val, Trp, or Tyr,
amino acid 240 to Ala, Ile, Met, or Thr,
amino acid 241 to Asp, Glu, Leu, Arg, Trp, or Tyr,
amino acid 243 to Leu, Glu, Leu, Gln, Arg, Trp, or Tyr,
amino acid 244 to His,
amino acid 245 to Ala,
amino acid 246 to Asp, Glu, His, or Tyr,
amino acid 247 to Ala, Phe, Gly, His, Ile, Leu, Met, Thr, Val, or Tyr,
amino acid 249 to Glu, His, Gln, or Tyr,
amino acid 250 to Glu, or Gln,
amino acid 251 to Phe,
amino acid 254 to Phe, Met, or Tyr,
amino acid 255 to Glu, Leu, or Tyr,
amino acid 256 to Ala, Met, or Pro,
amino acid 258 to Asp, Glu, His, Ser, or Tyr,
amino acid 260 to Asp, Glu, His, or Tyr,
amino acid 262 to Ala, Glu, Phe, Ile, or Thr,
amino acid 263 to Ala, Ile, Met, or Thr,
amino acid 264 to Asp, Glu, Phe, Gly, His, Ile, Lys, Leu, Met, Asn, Pro, Gln, Arg, Ser, Thr, Trp, or Tyr,
amino acid 265 to Ala, Leu, Phe, Gly, His, Ile, Lys, Leu, Met, Asn, Pro, Gln, Arg, Ser, Thr, Val, Trp, or Tyr,
amino acid 266 to Ala, Ile, Met, or Thr,
amino acid 267 to Asp, Glu, Phe, His, Ile, Lys, Leu, Met, Asn, Pro, Gln, Arg, Thr, Val, Trp, or Tyr,
amino acid 268 to Asp, Glu, Phe, Gly, Ile, Lys, Leu, Met, Pro, Gln, Arg, Thr, Val, or Trp,
amino acid 269 to Phe, Gly, His, Ile, Lys, Leu, Met, Asn, Pro, Arg, Ser, Thr, Val, Trp, or Tyr,
amino acid 270 to Glu, Phe, Gly, His, Ile, Leu, Met, Pro, Gln, Arg, Ser, Thr, Trp, or Tyr,
amino acid 271 to Ala, Asp, Glu, Phe, Gly, His, Ile, Lys, Leu, Met, Asn, Gln, Arg, Ser, Thr, Val, Trp, or Tyr,
amino acid 272 to Asp, Phe, Gly, His, Ile, Lys, Leu, Met, Pro, Arg, Ser, Thr, Val, Trp, or Tyr,
amino acid 273 to Phe, or Ile,
amino acid 274 to Asp, Glu, Phe, Gly, His, Ile, Leu, Met, Asn, Pro, Arg, Ser, Thr, Val, Trp, or Tyr,
amino acid 275 to Leu, or Trp,
amino acid 276 to Asp, Glu, Phe, Gly, His, Ile, Leu, Met, Pro, Arg, Ser, Thr, Val, Trp, or Tyr,
amino acid 278 to Asp, Glu, Gly, His, Ile, Lys, Leu, Met, Asn, Pro, Gln, Arg, Ser, Thr, Val, or Trp,
amino acid 279 to Ala,
amino acid 280 to Ala, Gly, His, Lys, Leu, Pro, Gln, Trp, or Tyr, amino acid 281 to Asp, Lys, Pro, or Tyr,
amino acid 282 to Glu, Gly, Lys, Pro, or Tyr,
amino acid 283 to Ala, Gly, His, Ile, Lys, Leu, Met, Pro, Arg, or Tyr,
amino acid 284 to Asp, Glu, Leu, Asn, Thr, or Tyr,
amino acid 285 to Asp, Glu, Lys, Gln, Trp, or Tyr,
amino acid 286 to Glu, Gly, Pro, or Tyr,
amino acid 288 to Asn, Asp, Glu, or Tyr,
amino acid 290 to Asp, Gly, His, Leu, Asn, Ser, Thr, Trp, or Tyr,
amino acid 291 to Asp, Glu, Gly, His, Ile, Gln, or Thr,
amino acid 292 to Ala, Asp, Glu, Pro, Thr, or Tyr,
amino acid 293 to Phe, Gly, His, Ile, Leu, Met, Asn, Pro, Arg, Ser, Thr, Val, Trp, or Tyr,
amino acid 294 to Phe, Gly, His, Ile, Lys, Leu, Met, Asn, Pro, Arg, Ser, Thr, Val, Trp, or Tyr,
amino acid 295 to Asp, Glu, Phe, Gly, His, Ile, Lys, Met, Asn, Pro, Arg, Ser, Thr, Val, Trp, or Tyr,
amino acid 296 to Ala, Asp, Glu, Gly, His, Ile, Lys, Leu, Met, Asn, Gln, Arg, Ser, Thr, or Val,
amino acid 297 to Asp, Glu, Phe, Gly, His, Ile, Lys, Leu, Met, Pro, Gln, Arg, Ser, Thr, Val, Trp, or Tyr,
amino acid 298 to Ala, Asp, Glu, Phe, His, Ile, Lys, Met, Asn, Gln, Arg, Thr, Val, Trp, or Tyr,
amino acid 299 to Ala, Asp, Glu, Phe, Gly, His, Ile, Lys, Leu, Met, Asn, Pro, Gln, Arg, Ser, Val, Trp, or Tyr,
amino acid 300 to Ala, Asp, Glu, Gly, His, Ile, Lys, Leu, Met, Asn, Pro, Gln, Arg, Ser, Thr, Val, or Trp,
amino acid 301 to Asp, Glu, His, or Tyr,
amino acid 302 to Ile,
amino acid 303 to Asp, Gly, or Tyr,
amino acid 304 to Asp, His, Leu, Asn, or Thr,
amino acid 305 to Glu, Ile, Thr, or Tyr,
amino acid 311 to Ala, Asp, Asn, Thr, Val, or Tyr,
amino acid 313 to Phe,
amino acid 315 to Leu,
amino acid 317 to Glu or Gln,
amino acid 318 to His, Leu, Asn, Pro, Gln, Arg, Thr, Val, or Tyr,
amino acid 320 to Asp, Phe, Gly, His, Ile, Leu, Asn, Pro, Ser, Thr, Val, Trp, or Tyr,
amino acid 322 to Ala, Asp, Phe, Gly, His, Ile, Pro, Ser, Thr, Val, Trp, or Tyr,
amino acid 323 to Ile,
amino acid 324 to Asp, Phe, Gly, His, Ile, Leu, Met, Pro, Arg, Thr, Val, Trp, or Tyr,
amino acid 325 to Ala, Asp, Glu, Phe, Gly, His, Ile, Lys, Leu, Met, Pro, Gln, Arg, Ser, Thr, Val, Trp, or Tyr,
amino acid 326 to Ala, Asp, Glu, Gly, Ile, Leu, Met, Asn, Pro, Gln, Ser, Thr, Val, Trp, or Tyr,
amino acid 327 to Ala, Asp, Glu, Phe, Gly, His, Ile, Lys, Leu, Met, Asn, Pro, Arg, Thr, Val, Trp, or Tyr,
amino acid 328 to Ala, Asp, Glu, Phe, Gly, His, Ile, Lys, Met, Asn, Pro, Gln, Arg, Ser, Thr, Val, Trp, or Tyr,
amino acid 329 to Asp, Glu, Phe, Gly, His, Ile, Lys, Leu, Met, Asn, Gln, Arg, Ser, Thr, Val, Trp, or Tyr,
amino acid 330 to Cys, Glu, Phe, Gly, His, Ile, Lys, Leu, Met, Asn, Pro, Arg, Ser, Thr, Val, Trp, or Tyr,
amino acid 331 to Asp, Phe, His, Ile, Leu, Met, Gln, Arg, Thr, Val, Trp, or Tyr,
amino acid 332 to Ala, Asp, Glu, Phe, Gly, His, Lys, Leu, Met, Asn, Pro, Gln, Arg, Ser, Thr, Val, Trp, or Tyr,
amino acid 333 to Ala, Asp, Glu, Phe, Gly, His, Ile, Leu, Met, Pro, Ser, Thr, Val, or Tyr,
amino acid 334 to Ala, Glu, Phe, Ile, Leu, Pro, or Thr,
amino acid 335 to Asp, Phe, Gly, His, Ile, Leu, Met, Asn, Pro, Arg, Ser, Val, Trp, or Tyr,
amino acid 336 to Glu, Lys, or Tyr,
amino acid 337 to Glu, His, or Asn,
amino acid 339 to Asp, Phe, Gly, Ile, Lys, Met, Asn, Gln, Arg, Ser, or Thr,
amino acid 376 to Ala, or Val,
amino acid 377 to Gly, or Lys,
amino acid 378 to Asp,
amino acid 379 to Asn,
amino acid 380 to Ala, Asn, or Ser,
amino acid 382 to Ala, or Ile,
amino acid 385 to Glu,
amino acid 392 to Thr,
amino acid 396 to Leu,
amino acid 421 to Lys,
amino acid 427 to Asn,
amino acid 428 to Phe, or Leu,
amino acid 429 to Met,
amino acid 434 to Trp,
amino acid 436 to Ile, or
amino acid 440 to Gly, His, Ile, Leu, or Tyr based on the EU numbering in the Fc region. The number of amino acids to be modified is not limited. Only one amino acid may be modified, or two or more amino acids may be modified. Examples of combinations of amino acid modifications at two or more positions include combinations as described in Table 3 (Tables 3-1 to 3-3). Also, WO2007/047291 discloses specific examples of the anti-GPC3 antibody comprising the FcγR-binding modified Fc region having higher binding activity against Fcγ receptors than that of the native human IgG Fc region against Fcγ receptors.

TABLE 3-1

| ds | |
|---|---|
| K370E/P396L/D270E | S239Q/I332Q |
| Q419H/P396L/D270E | S267D/I332E |
| V240A/P3996L/D270E | S267E/I332E |
| R255L/P396L/D270E | S267L/A327S |
| R255L/P396L/D270E | S267Q/A327S |
| R255L/P396L/D270E/R292G | S298A/I332E |
| R255L/P396L/D270E | S304T/I332E |
| R255L/P396L/D270E/Y300L | S324G/I332D |
| F243L/D270E/K392N/P396L | S324G/I332E |
| F243L/R255L/D270E/P396L | S324I/I332D |
| F243L/R292P/Y300L/V305I/P396L | S324I/I332E |
| F243L/R292P/Y300L/P396L | T260H/I332E |
| F243L/R292P/Y300L | T335D/I332E |
| F243L/R292P/P396L | V240I/V266I |
| F243L/R292P/V305I | V264I/I332E |
| F243L/R292P | D265F/N297E/I332E |
| S298A/E333A/K334A | D265Y/N297D/I332E |
| E380A/T307A | F243L/V262I/V264W |
| K326M/E333S | N297D/A330Y/I332E |
| K326A/E333A | N297D/T299E/I332E |
| S317A/K353A | N297D/T299F/I332E |
| A327D/I332E | N297D/T299H/I332E |
| A330L/I332E | N297D/T299I/I332E |
| A330Y/I332E | N297D/T299L/I332E |
| E258H/I332E | N297D/T299V/I332E |
| E272H/I332E | P230A/E233D/I332E |
| E272I/N276D | P244H/P245A/P247V |
| E272R/I332E | S239D/A330L/I332E |
| E283H/I332E | S239D/A330Y/I332E |
| E293R/I332E | S239D/H268E/A330Y |
| F241L/V262I | S239D/I332E/A327A |
| F241W/F243W | S239D/I332E/A330I |
| F243L/V264I | S239D/N297D/I332E |
| H268D/A330Y | S239D/S298A/I332E |
| H268E/A330Y | S239D/V264I/I332E |
| K246H/I332E | S239E/N297D/I332E |
| L234D/I332E | S239E/V264I/I332E |

TABLE 3-1-continued

| ds | |
|---|---|
| L234E/I332E | S239N/A330L/I332E |
| L234G/I332E | S239N/A330Y/I332E |
| L234I/I332E | S239N/S298A/I332E |
| L234I/L235D | S239Q/V264I/I332E |
| L234Y/I332E | V264E/N297D/I332E |
| L235D/I332E | V264I/A330L/I332E |
| L235E/I332E | V264I/A330Y/I332E |
| L235I/I332E | V264I/S298A/I332E |
| L235S/I332E | Y296D/N297D/I332E |
| L328A/I332D | Y296E/N297D/I332E |
| L328D/I332D | Y296H/N297D/I332E |
| L328D/I332E | Y296N/N297D/I332E |
| L328E/I332D | Y296Q/N297D/I332E |
| L328E/I332E | Y296T/N297D/I332E |
| L328F/I332D | D265Y/N297D/T299L/I332E |
| L328F/I332E | F241E/F243Q/V262T/V264E |
| L328H/I332E | F241E/F243R/V262E/V264R |
| L328I/I332D | F241E/F243Y/V262T/V264R |
| L328I/I332E | F241L/F243L/V262I/V264I |
| L328M/I332D | F241R/F243Q/V262T/V264R |
| L328M/I332E | F241S/F243H/V262T/V264T |
| L328N/I332D | F241W/F243W/V262A/V264A |
| L328N/I332E | F241Y/F243Y/V262T/V264T |
| L328Q/I332D | I332E/A330Y/H268E/A327A |
| L328Q/I332E | N297D/I332E/S239D/A330L |
| L328T/I332D | N297D/S298A/A330Y/I332E |
| L328T/I332E | S239D/A330Y/I332E/K326E |
| L328V/I332D | S239D/A330Y/I332E/K326T |
| L328V/I332E | S239D/A330Y/I332E/L234I |
| L328Y/I332D | S239D/A330Y/I332E/L235D |
| L328Y/I332E | S239D/A330Y/I332E/V240I |
| N297D/I332E | S239D/A330Y/I332E/V264T |
| N297E/I332E | S239D/A330Y/I332E/V266I |
| N297S/I322E | S239D/D265F/N297D/I332E |
| P227G/I332E | S239D/D265H/N297D/I332E |
| P230A/E233D | S239D/D265I/N297D/I332E |
| Q295E/I332E | S239D/D265L/N297D/I332E |
| R255Y/I332E | S239D/D265T/N297D/I332E |
| S239D/I332D | S239D/D265V/N297D/I332E |
| S239D/I332E | S239D/D265Y/N297D/I332E |
| S239D/I332N | S239D/I332E/A330Y/A327A |
| S239D/I332Q | S239D/I332E/H268E/A327A |
| S239E/D265G | S239D/I332E/H268E/A330Y |
| S239E/D265N | S239D/N297D/I332E/A330Y |
| S239E/D265Q | S239D/N297D/I332E/K326E |
| S239E/I332D | S239D/N297D/I332E/L235D |
| S239E/I332E | S239D/V264I/A330L/I332E |
| S239E/I332N | S239D/V264I/S298A/I332E |
| S239E/I332Q | S239E/V264I/A330Y/I332E |
| S239N/I332D | F241E/F243Q/V262T/V264E/I332E |
| S239N/I332E | F241E/F243R/V262E/V264R/I332E |
| S239N/I332N | F241E/F243Y/V262T/V264R/I332E |
| S239N/I332Q | F241R/F243Q/V262T/V264R/I332E |
| S239Q/I332D | S239D/I332E/H268E/A330Y/A327A |
| S239Q/I332E | S239E/V264I/S298A/A330Y/I332E |
| S239Q/I332N | F241Y/F243Y/V262T/V264T/N297D/I332E |
| S267E/L328F | G236D/S267E |
| S239D/S267E | |

The Fcγ receptor-binding domain contained in the anti-GPC3 antibody of the present invention can be assayed for its binding activity against the Fcγ receptor appropriately using pH conditions selected from acidic to neutral regions of pH. The acidic to neutral regions of pH as the conditions under which the Fcγ receptor-binding domain contained in the antigen-binding molecule of the present invention is assayed for its binding activity against the Fcγ receptor usually mean pH 5.8 to pH 8.0. The pH range is preferably indicated by arbitrary pH values from pH 6.0 to pH 7.4 and is preferably selected from pH 6.0, 6.1, 6.2, 6.3, 6.4, 6.5, 6.6, 6.7, 6.8, 6.9, 7.0, 7.1, 7.2, 7.3, and 7.4. Particularly, a pH range of 6.15 to 7.4, which is close to the pH of cancer tissues, is preferred (Vaupel et al., Cancer Res. (1989) 49, 6449-6665). The binding affinity of the Fc region for the human Fcγ receptor can be evaluated under assay conditions involving an arbitrary temperature of 10° C. to 50° C. Preferably, a temperature of 15° C. to 40° C. is used for determining the binding affinity of the Fc region for the human Fcγ receptor. More preferably, an arbitrary temperature of 20° C. to 35° C., for example, any one temperature of 20, 21, 22, 23, 24, 25, 26, 27, 28, 29, 30, 31, 32, 33, 34, and 35° C., is also used for determining the binding affinity of the Fc region for the Fcγ receptor. The temperature 25° C. is one non-limiting example in an aspect of the present invention.

The phrase "FcγR-binding modified Fc region having higher binding activity against Fcγ receptors than that of the native Fc region against Fcγ receptors" described herein means that the FcγR-binding modified Fc region has higher binding activity against any of the human Fcγ receptors FcγRI, FcγRIIa, FcγRIIb, FcγRIIIa, and/or FcγRIIIb than that of the native Fc region against the human Fcγ receptor. The phrase means that, for example, on the basis of the analysis method described above, the anti-GPC3 antibody comprising the FcγR-binding modified Fc region exhibits 105% or more, preferably 110% or more, 115% or more, 120% or more, or 125% or more, particularly preferably 130% or more, 135% or more, 140% or more, 145% or more, 150% or more, 155% or more, 160% or more, 165% or more, 170% or more, 175% or more, 180% or more, 185% or more, 190% or more, 195% or more, 2 times or more, 2.5 times or more, 3 times or more, 3.5 times or more, 4 times or more, 4.5 times or more, 5 times or more, 7.5 times or more, 10 times or more, 20 times or more, 30 times or more, 40 times or more, 50 times or more, 60 times or more, 70 times or more, 80 times or more, 90 times or more, 100 times or more binding activity compared with the binding activity of an anti-GPC3 antibody comprising the native Fc region of human IgG serving as a control. The native Fc region used may be the starting Fc region or may be the native Fc region of an antibody of the same subclass as the anti-GPC antibody concerned.

In the present invention, a native human IgG Fc region having a fucose-containing sugar chain as a sugar chain bound to amino acid 297 (EU numbering) is preferably used as the native Fc region of human IgG serving as a control. Whether or not the sugar chain bound to amino acid 297 (EU numbering) is a fucose-containing sugar chain can be confirmed using an approach known in the art. Whether or not the sugar chain bound to the native human IgG Fc region is a fucose-containing sugar chain can be determined by, for example, a method as shown below. The native human IgG to be tested liberates a sugar chain through reaction with N-Glycosidase F (Roche Diagnostics K.K.) (Weitzhandler et al., J. Pharma. Sciences (1994) 83, 12, 1670-1675). Next, proteins are removed through reaction with ethanol, and the resulting reaction solution (Schenk et al., J. Clin. Investigation (2001) 108 (11) 1687-1695) is evaporated to dryness and then fluorescently labeled with 2-aminobenzamide (Bigge et al., Anal. Biochem. (1995) 230 (2) 229-238). After removal of the reagent by solid-phase extraction using a cellulose cartridge, the 2-AB-fluorescently labeled sugar chain is analyzed by normal-phase chromatography. The detected peak in the chromatogram can be observed to thereby determine whether or not the sugar chain bound to the native Fc region of human IgG is a fucose-containing sugar chain.

An anti-GPC3 antibody having an IgG monoclonal antibody Fc region can be appropriately used as the anti-GPC3 antibody comprising the native Fc region of an antibody of the same subclass serving as a control. Structural examples of the Fc region include Fc regions contained in constant regions represented by SEQ ID NOs: 74 (having A added to the N terminus of the sequence of database registration No. AAC82527.1), 75 (having A added to the N terminus of the sequence of database registration No. AAB59393.1), 76 (database registration No. CAA27268.1), and 77 (having A added to the N terminus of the sequence of database registration No. AAB59394.1). In the case of using a certain isotype of anti-GPC3 antibody as a test substance, the anti-GPC3 antibody comprising the Fc region to be tested is studied for its effect of binding activity against Fcγ receptors by use of an anti-GPC3 antibody of the certain isotype as a control. The anti-GPC3 antibody comprising the Fc region thus confirmed to have higher binding activity against Fcγ receptors is appropriately selected.

Fc region having higher binding activity against active Fcγ receptor than its binding activity against inhibitory Fcγ receptor.

As described above, preferred examples of the active Fcγ receptors include FcγRI (CD64) including FcγRIa, FcγRIb, and FcγRIc, FcγRIIa, and FcγRIII (CD16) including isoforms FcγRIIIa (including allotypes V158 and F158) and FcγRIIIb (including allotypes FcγRIIIb-NA1 and FcγRIIIb-NA2). Preferred examples of the inhibitory Fcγ receptors include FcγRIIb (including FcγRIIb-1 and FcγRIIb-2).

In a non-limiting aspect, alternative examples of the anti-GPC3 antibody of the present invention include an anti-GPC3 antibody comprising an Fc region having higher binding activity against active Fcγ receptors than its binding activity against inhibitory Fcγ receptors. In this case, the phrase "having higher binding activity against active Fcγ receptors than its binding activity against inhibitory Fcγ receptors" means that the Fc region has higher binding activity against any of the human Fcγ receptors FcγRIa, FcγRIIa, FcγRIIIa, and/or FcγRIIIb than its binding activity against FcγRIIb. The phrase means that, for example, on the basis of the analysis method described above, the antigen-binding molecule comprising the Fc region exhibits 105% or more, preferably 110% or more, 120% or more, 130% or more, or 140% or more, particularly preferably 150% or more, 160% or more, 170% or more, 180% or more, 190% or more, 200% or more, 250% or more, 300% or more, 350% or more, 400% or more, 450% or more, 500% or more, 750% or more, 10 times or more, 20 times or more, 30 times or more, 40 times or more, 50 times, 60 times, 70 times, 80 times, 90 times, or 100 times or more binding activity against any of the human Fcγ receptors FcγRIa, FcγRIIa, FcγRIIIa, and/or FcγRIIIb compared with its binding activity against FcγRIIb. The IgG antibody comprising such an Fc region is known to have enhancement in the ADCC activity. Thus, the anti-GPC3 antibody comprising the Fc region is useful as the GPC3-targeting drug of the present invention.

In a non-limiting aspect of the present invention, examples of the Fc region having higher binding activity against active Fcγ receptors than its binding activity against inhibitory Fcγ receptors (having selective binding activity against active Fcγ receptors) preferably include Fc regions in which at least one or more amino acids selected from the group consisting of position 221, position 222, position 223, position 224, position 225, position 227, position 228, position 230, position 231, position 232, position 233, position 234, position 235, position 236, position 237, position 238, position 239, position 240, position 241, position 243, position 244, position 245, position 246, position 247, position 249, position 250, position 251, position 254, position 255, position 256, position 258, position 260, position 262, position 263, position 264, position 265, position 266, position 267, position 268, position 269, position 270, position 271, position 272, position 273, position 274, position 275, position 276, position 278, position 279, position 280, position 281, position 282, position 283, position 284, position 285, position 286, position 288, position 290, position 291, position 292, position 293, position 294, position 295, position 296, position 297, position 298, position 299, position 300, position 301, position 302, position 303, position 304, position 305, position 311, position 313, position 315, position 317, position 318, position 320, position 322, position 323, position 324, position 325, position 326, position 327, position 328, position 329, position 330, position 331, position 332, position 333, position 334, position 335, position 336, position 337, position 339, position 376, position 377, position 378, position 379, position 380, position 382, position 385, position 392, position 396, position 421, position 427, position 428, position 429, position 434, position 436 and position 440 (EU numbering) are modified to amino acids different from those in the native Fc region.

In a non-limiting aspect of the present invention, further examples of the Fc region having higher binding activity against active Fcγ receptors than its binding activity against inhibitory Fcγ receptors (having selective binding activity against active Fcγ receptors) preferably include Fc regions in which a plurality of amino acids described in Tables 3-1 to 3-3 are modified to amino acids different from those in the native Fc region.

Fc Region Having Modified Sugar Chain

The Fc region contained in the anti-GPC3 antibody provided by the present invention can also include an Fc region modified such that a higher proportion of fucose-deficient sugar chains is bound to the Fc region or a higher proportion of bisecting N-acetylglucosamine is added to the Fc region in the composition of sugar chains bound to the Fc region. The removal of a fucose residue from N-acetylglucosamine at the reducing end of a N-glycoside-linked complex sugar chain bound to an antibody Fc region is known to enhance its affinity for FcγRIIIa (Sato et al., Expert Opin. Biol. Ther. (2006) 6 (11), 1161-1173). An IgG1 antibody comprising such an Fc region is known to have enhancement in the ADCC activity. Thus, the antigen-binding molecule comprising the Fc region is also useful as the antigen-binding molecule contained in the pharmaceutical composition of the present invention. Examples of an antibody that lacks a fucose residue in N-acetylglucosamine at the reducing end of a N-glycoside-linked complex sugar chain bound to the antibody Fc region include the following antibodies:

glycosylated antibodies (e.g., International Publication No. WO1999/054342); and antibodies deficient in fucose added to the sugar chain (e.g., International Publication Nos. WO2000/061739, WO2002/031140, and WO2006/067913).

Also, WO2006/046751 and WO2009/041062 disclose specific examples of the anti-GPC3 antibody comprising the Fc region modified such that a higher proportion of fucose-deficient sugar chains is bound to the Fc region or a higher proportion of bisecting N-acetylglucosamine is added to the Fc region in the composition of sugar chains bound to the Fc region.

More specifically, in an alternative non-limiting aspect of the antibody that lacks a fucose residue in N-acetylglucosamine at the reducing end of a N-glycoside-linked complex sugar chain bound to the antibody Fc region, the antibody deficient in fucose added to the sugar chain (e.g., International Publication Nos. WO2000/061739, WO2002/031140, and WO2006/067913) may be prepared. For this purpose, host cells less able to add fucose to sugar chains are prepared as a result of altering the activity of forming the sugar chain structures of polypeptides that undergo sugar chain modification. The host cells are allowed to express the desired antibody gene, and the antibody deficient in fucose in its sugar chain can be recovered from the culture solution of the host cells. Non-limiting preferred examples of the activity of forming the sugar chain structures of polypeptides can include the activity of an enzyme or a transporter selected from the group consisting of fucosyltransferase (EC 2.4.1.152), fucose transporter (SLC35C1), GDP-mannose 4,6-dehydratase (GMD) (EC 4.2.1.47), GDP-keto-6-deoxymannose 3,5-epimerase/4-reductase (Fx) (EC 1.1.1.271), and GDP-β-L-fucose pyrophosphorylase (GFPP) (EC 2.7.7.30). These enzymes or transporters are not necessarily limited by their structures as long as the enzymes or the transporters can exert their activity. These proteins capable of exerting such activity are referred to as functional proteins herein. In a non-limiting aspect, examples of methods for altering the activity include the deletion of the activity. Host cells that lack the activity can be prepared by an appropriately adopted method known in the art such as a method which involves disrupting the genes of these functional proteins to render the genes unfunctional (e.g., International Publication Nos. WO2000/061739, WO2002/031140, and WO2006/067913). Such host cells that lack the activity may be prepared by, for example, a method which involves disrupting the endogenous genes of these functional proteins in cells such as CHO cells, BHK cells, NS0 cells, SP2/0 cells, YO myeloma cells, P3X63 mouse myeloma cells, PER cells, PER.C6 cells, HEK293 cells, or hybridoma cells to render the genes unfunctional.

Antibodies containing sugar chains having bisecting GlcNAc (e.g., International Publication No. WO2002/079255) are known in the art. In a non-limiting aspect, host cells expressing genes encoding functional proteins having β-1,4-mannosyl-glycoprotein 4-β-N-acetylglucosaminyltransferase (GnTIII) (EC 2.4.1.144) activity or β-1,4-galactosyltransferase (GalT) (EC 2.4.1.38) activity are prepared in order to prepare such an antibody containing sugar chains having bisecting GlcNAc. In another non-limiting preferred aspect, host cells coexpressing a gene encoding a functional protein having human mannosidase II (ManII) (3.2.1.114) activity, a gene encoding a functional protein having β-1,2-acetylglucosaminyltransferase I (GnTI) (EC 2.4.1.94) activity, a gene encoding a functional protein having β-1,2-acetylglucosaminyltransferase II (GnTII) (EC 2.4.1.143) activity, a gene encoding a functional protein having mannosidase I (ManI) (EC 3.2.1.113) activity, and an α-1,6-fucosyltransferase (EC 2.4.1.68) gene, in addition to the functional proteins described above, are prepared (International Publication Nos. WO2004/065540).

The host cells less able to add fucose to sugar chains and the host cells having the activity of forming sugar chains having bisecting GlcNAc structures as described above can be transformed with antibody gene-containing expression vectors to respectively prepare the antibody that lacks a fucose residue in N-acetylglucosamine at the reducing end of a N-glycoside-linked complex sugar chain bound to the antibody Fc region and the antibody containing sugar chains having bisecting GlcNAc. The methods for producing these antibodies are also applicable to a method for producing the antigen-binding molecule comprising the Fc region modified such that a higher proportion of fucose-deficient sugar chains is bound to the Fc region or a higher proportion of bisecting N-acetylglucosamine is added to the Fc region in the composition of sugar chains bound to the Fc region of the present invention. The composition of sugar chains bound to the Fc region contained in the antigen-binding molecule of the present invention prepared by such a production method can be confirmed by the method described in the paragraph "Fcγ receptor (FcγR)-binding modified Fc region".

Anti-GPC3 Antibody Having Altered Isoelectric Point

In a non-limiting aspect, further examples of the anti-GPC3 antibody that may be used in the present invention include an anti-GPC3 antibody having an amino acid residue modified to alter its isoelectric point (pI). Preferred examples of the "alteration of the electric charge of an amino acid residue" in the anti-GPC3 antibody provided by the present invention are as follows: alteration to increase the pI value can be performed by, for example, at least one substitution selected from the substitution of Q by K at position 43, the substitution of D by N at position 52, and the substitution of Q by R at position 105 based on the Kabat numbering in the anti-GPC3 antibody heavy chain variable region represented by SEQ ID NO: 50, which is consequently modified to, for example, the amino acid sequence represented by SEQ ID NO: 67. Also, this alteration can be performed by, for example, at least one substitution selected from the substitution of E by Q at position 17, the substitution of Q by R at position 27, and the substitution of Q by R at position 105 based on the Kabat numbering in the anti-GPC3 antibody light chain variable region represented by SEQ ID NO: 51 or 66, which is consequently modified to, for example, the amino acid sequence represented by SEQ ID NO: 68. On the other hand, alteration to decrease the pI value can be performed by at least one substitution selected from the substitution of K by T at position 19, the substitution of Q by E at position 43, the substitution of G by E at position 61, the substitution of K by S at position 62, the substitution of K by Q at position 64, and the substitution of G by D at position 65 based on the Kabat numbering in the anti-GPC3 antibody heavy chain variable region represented by SEQ ID NO: 50, which is consequently modified to, for example, the amino acid sequence represented by SEQ ID NO: 69 or 71. Also, this alteration can be performed by, for example, at least one substitution selected from the substitution of R by Q at position 24, the substitution of Q by E at position 27, the substitution of K by T at position 74, the substitution of R by S at position 77, and the substitution of K by E at position 107 based on the Kabat numbering in the anti-GPC3 antibody light chain variable region represented by SEQ ID NO: 51 or 66, which is consequently modified to, for example, the amino acid sequence represented by SEQ ID NO: 70, 72, or 73. Further examples of the alteration to decrease the pI value include the substitution of at least one amino acid selected from amino acids 268, 274, 355, 356, 358, and 419 based on the EU numbering in the heavy chain constant region represented by SEQ ID NO: 74. Preferred examples of these substitutions can include at least one substitution selected from the substitution of H by Q at position 268, the substitution of K by Q at position 274, the substitution of R by Q at position 355, the substitution of D by E at position 356, the substitution of L by M at position 358, and the substitution of Q by E at position 419 based on the EU numbering in the heavy chain constant region represented by SEQ ID NO: 31. As a result of these substitutions, a chimera having human antibody IgG1 and IgG4 constant regions is constructed. Specifically, these substitutions can yield an antibody having the desired pI without influencing the immunogenicity of the modified antibody.

Modification to Reduce Heterogeneity

An IgG constant region deficient in Gly at position 446 and Lys at position 447 based on the EU numbering in the IgG constant region represented by SEQ ID NO: 74, 75, 76, or 77 may also be used as the constant region contained in the anti-GPC3 antibody of the present invention. Deficiency in both of these amino acids can reduce heterogeneity derived from the end of the heavy chain constant region of the antibody.

Antibody Modification

The posttranslational modification of a polypeptide refers to chemical modification given to the polypeptide translated during polypeptide biosynthesis. Since the primary structure of an antibody is composed of a polypeptide, the anti-GPC3 antibody of the present invention also includes a modified form that has received the posttranslational modification of the polypeptide constituting the primary structure of the anti-GPC3 antibody. The posttranslational modification of a polypeptide can be broadly classified into the addition of a functional group, the addition of a polypeptide or a peptide (ISGylation, SUMOylation, or ubiquitination), the conversion of the chemical properties of an amino acid (silylation, deamination, or deamidation), and structural conversion (disulfidation or protease degradation). In a non-limiting aspect, examples of the posttranslational modification according to the present invention include the addition of a peptide or a functional group to an amino acid residue as a unit constituting the polypeptide. Examples of such modification can specifically include phosphorylation (serine, threonine, tyrosine, aspartic acid, etc.), glucosylation (serine, threonine, aspartic acid, etc.), acylation (lysine), acetylation (lysine), hydroxylation (lysine and proline), prenylation (cysteine), palmitoylation (cysteine), alkylation (lysine and arginine), polyglutamylation (glutamic acid), carboxylation (glutamic acid), polyglycylation (glutamic acid), citrullination (arginine), and succinimide formation (aspartic acid). For example, an anti-GPC3 antibody that has received the modification of N-terminal glutamine to pyroglutamic acid by pyroglutamylation is also included in the anti-GPC3 antibody of the present invention, as a matter of course. Also, for example, a posttranslationally modified anti-GPC3 antibody comprising heavy and light chains or heavy chains linked via a "disulfide bond", which means a covalent bond formed between two sulfur atoms is included in the anti-GPC3 antibody of the present invention. A thiol group contained in an amino acid cysteine can form a disulfide bond or crosslink with a second thiol group. In general IgG molecules, CH1 and CL regions are linked via a disulfide bond, and two polypeptides constituting heavy chains are linked via a disulfide bond between cysteine residues at positions 226 and 229 based on the EU numbering. A posttranslationally modified anti-GPC3 antibody having such a linkage via a disulfide bond is also included in the anti-GPC3 antibody of the present invention.

GPC3-Targeting Drug Therapy

The term "GPC3-targeting drug therapy" refers to the administration of a GPC3-targeting drug to a patient.

The phrase "efficacy of GPC3-targeting drug therapy for cancer" or "GPC3-targeting drug therapy has efficacy for cancer" means that the GPC3-targeting drug therapy produces desired or beneficial effects on a patient diagnosed with cancer. The desired or beneficial effects can include: (1) the inhibition of the further growth or diffusion of cancer cells; (2) the killing of cancer cells; (3) the inhibition of cancer recurrence; (4) the alleviation, reduction, mitigation, or inhibition of cancer-related symptoms (pain, etc.) or reduction in the frequency of the symptoms; and (5) improvement in the survival rate of the patient. The inhibition of cancer recurrence includes the inhibition of the growth of cancer already treated by radiation, chemotherapy, surgical operation, or other techniques, at the primary site of the cancer and its neighboring tissues, and the absence of the growth of cancer at a new distal site. The desired or beneficial effects may be subjectively perceived by the patient or may be objectively found. In the case of, for example, a human patient, the human is able to recognize improvement in energy or vitality or reduction in pain as improvement or a therapy-responsive sign perceived by the patient. Alternatively, a clinician is able to notice decrease in tumor size or the amount of tumor tissues on the basis of findings gained by physical examination, experimental parameters, tumor markers, or X-ray photography. Some experimental signs that can be observed by the clinician in response to treatment include normalized test results of, for example, leukocyte counts, erythrocyte counts, platelet counts, erythrocyte sedimentation rates, and levels of various enzymes. The clinician is further able to observe decrease in detectable tumor marker level. Alternatively, other tests, such as sonography, nuclear magnetic resonance test, and positron emission test, may be used for evaluating objective improvement.

Any cancer having high expression of targeted GPC3 corresponds to the cancer to be treated by the GPC3-targeting drug therapy of the present invention. One example of such cancer include cancer selected from breast cancer, uterine cervix cancer, colon cancer, uterine body cancer, head and neck cancer, liver cancer, lung cancer, malignant carcinoid, malignant glioma, malignant lymphoma, malignant melanoma, ovary cancer, pancreatic cancer, prostatic cancer, renal cancer, skin cancer, gastric cancer, testicle cancer, thyroid cancer, urothelial cancer, and the like.

Method for Determining Efficacy of GPC3-Targeting Drug Therapy or Method for Determining Continuation of GPC3-Targeting Drug Therapy In a non-limiting aspect, the present invention provides a method comprising measuring the number of an immunocyte and/or an expression level of a molecule expressed on the immunocyte in a biological sample isolated from a patient before the start of GPC3-targeting drug therapy and/or a patient treated with the GPC3-targeting drug therapy, wherein when the number of an immunocyte and/or the expression level is a predetermined value, the efficacy of the GPC3-targeting drug therapy is determined or the continuation of the GPC3-targeting drug therapy is determined. The "patient before the start of GPC3-targeting drug therapy" refers to a patient diagnosed with cancer, having no history of administration of the GPC3-targeting drug. The patient may be a patient for which the efficacy of the GPC3-targeting drug therapy has been determined from the expression level of GPC3 in the tissues. Further, the "patient treated with GPC3-targeting drug therapy" refers to a patient having a history of administration of the GPC3-targeting drug. The administration route of the GPC3-targeting drug can be appropriately selected from administration routes suitable for the properties, etc., of the GPC3-targeting drug to be administered. Examples of the administration route include parenteral administration. Further examples of the parenteral administration include injection, transnasal administration, transpulmonary administration, and percutaneous administration. Further examples of the injection include systemic or local administration based on intravenous injection, intramuscular injection, intraperitoneal injection, and subcutaneous injection.

In a non-limiting aspect, the method of the present invention comprises measuring the number of an immunocyte in a biological sample isolated from the patient, wherein when the number of an immunocyte is a predetermined value, the efficacy of the GPC3-targeting drug therapy for cancer in the patient is predicted, expected, or determined or the continuation of the therapy is determined. Examples of the immunocyte for the measurement in the present invention include, but not limited to, leukocytes, monocytes, neutrophils, and lymphocytes. Examples of the lymphocytes include CD19+ B cells, CD45+ lymphocytes, CD3+ T cells, CD4+ T cells, CD8+ T cells, CD4+/CD8+ T cells, CD16+ NK cells, NKp46+ NK cells, strongly CD56-positive NK cells, CD56−/CD16+ NK cells, weakly or moderately CD56-positive and CD16-negative NK cells, and weakly or moderately CD56-positive and strongly CD16-positive NK cells. The number of any one type of these cells may be measured and used as an index for predicting, expecting, or determining the efficacy of the GPC3-targeting drug therapy for cancer. Alternatively, the numbers of two or more types of these cells in combination may be used as an index.

The predetermined value can be regarded as a predetermined value at which the effect of the GPC3-targeting drug therapy can be expected, for example, provided that this value falls within a range higher than the average number of an immunocyte in a patient group for which the effect of the GPC3-targeting drug therapy on cancer cannot be confirmed among a plurality of cancer patients treated with the GPC3-targeting drug therapy. For example, the predetermined value can also be determined on the basis of the average number of an immunocyte in a patient group showing a tendency toward significantly prolonged PFS or significantly prolonged OS among a plurality of cancer patients treated with the GPC3-targeting drug therapy. For example, a predetermined value for selecting with a high probability a patient showing a tendency toward significantly prolonged PFS or significantly prolonged OS as a result of GPC3-targeting drug therapy can be determined by measuring the numbers of immunocytes in a plurality of cancer patients and setting the predetermined value to a value higher than the median value thereof. In this context, a plurality of cancer patients may be any number of cancer patients as long as the predetermined value for the number of an immunocyte serving as a criterion for determining the efficacy of GPC3-targeting drug therapy or the continuation of the therapy can be calculated as a significant value. The number of cancer patients is preferably 100 or more, more preferably 150 or more. Specifically, the predetermined value can be determined from a value higher than a particular value such as 2500 cells/μL, 3000 cells/μL, 3500 cells/μL, 4000 cells/μL, 4350 cells/μL, 4500 cells/μL, 4750 cells/μL, 5000 cells/μL, 5250 cells/μL, 5500 cells/μL, 5750 cells/μL, 6000 cells/μL, 6500 cells/μL, 7000 cells/μL, 7500 cells/μL, 8000 cells/μL, 8500 cells/μL, or 9000 cells/μL, for example, in terms of the number of leukocytes. The particular value can be appropriately selected from a numerical range from, for example, 2500 cells/μL to 9000 cells/μL. The numerical range is preferably, for example, from 3000 cells/μL to 8000 cells/μL. The numerical range is more preferably, for example, from 3500 cells/μL to 7000 cells/μL, further preferably, for example, from 4000 cells/μL to 6000 cells/μL, though the numerical range is not limited to these values. A value higher than the particular value selected from the numerical range can be used as the predetermined value.

The predetermined value can be determined from a value higher than a particular value such as 50 cells/μL, 100 cells/μL, 200 cells/μL, 300 cells/μL, 350 cells/μL, 400 cells/μL, 450 cells/μL, 500 cells/μL, 550 cells/μL, 600 cells/μL, 650 cells/μL, 700 cells/μL, 800 cells/μL, 900 cells/μL, 1000 cells/μL, 1100 cells/μL, in terms of the number of monocytes. The particular value can be appropriately selected from a numerical range from, for example, 50 cells/μL to 1100 cells/μL. The numerical range is preferably, for example, from 100 cells/μL to 1000 cells/μL. The numerical range is more preferably, for example, from 200 cells/μL to 900 cells/μL, further preferably, for example, from 400 cells/μL to 800 cells/μL, though the numerical range is not limited to these values. A value higher than the particular value selected from the numerical range can be used as the predetermined value.

The predetermined value can be determined from a value higher than a particular value such as 500 cells/μL, 1000 cells/μL, 1500 cells/μL, 2000 cells/μL, 2500 cells/μL, 3000 cells/μL, 3250 cells/μL, 3500 cells/μL, 3750 cells/μL, 4000 cells/μL, 4250 cells/μL, 4500 cells/μL, 5000 cells/μL, 5500 cells/μL, 6000 cells/μL, 6500 cells/μL, 7000 cells/μL, in terms of the number of neutrophils. The particular value can be appropriately selected from a numerical range from, for example, 500 cells/μL to 7000 cells/μL. The numerical range is preferably, for example, from 1000 cells/μL to 6000 cells/μL. The numerical range is more preferably, for example, from 1500 cells/μL to 5000 cells/μL, further preferably, for example, from 3000 cells/μL to 4000 cells/μL, though the numerical range is not limited to these values. A value higher than the particular value selected from the numerical range can be used as the predetermined value.

The predetermined value can be determined from a value higher than a particular value such as 400 cells/μL, 500 cells/μL, 600 cells/μL, 700 cells/μL, 800 cells/μL, 900 cells/μL, 1000 cells/μL, 1100 cells/μL, 1200 cells/μL, 1250 cells/μL, 1300 cells/μL, 1400 cells/μL, 1500 cells/μL, 1600 cells/μL, 1700 cells/μL, 1800 cells/μL, 1900 cells/μL, 2000 cells/μL, 2100 cells/μL, 2200 cells/μL, 2300 cells/μL, 2400 cells/μL, 2500 cells/μL, 3000 cells/μL, 3500 cells/μL, 4000 cells/μL, in terms of the number of lymphocytes. The particular value can be appropriately selected from a numerical range from, for example, 400 cells/μL to 4000 cells/μL. The numerical range is preferably, for example, from 450 cells/μL to 3000 cells/μL. The numerical range is more preferably, for example, from 500 cells/μL to 2500 cells/μL, further preferably, for example, from 1000 cells/μL to 2000 cells/μL, though the numerical range is not limited to these values. A value higher than the particular value selected from the numerical range can be used as the predetermined value.

The predetermined value can be determined from a value higher than a particular value such as 400 cells/μL, 500 cells/μL, 600 cells/μL, 700 cells/μL, 800 cells/μL, 900 cells/μL, 950 cells/μL, 1000 cells/μL, 1050 cells/μL, 1100 cells/μL, 1200 cells/μL, 1300 cells/μL, 1400 cells/μL, 1500 cells/μL, 1600 cells/μL, 1700 cells/μL, 1800 cells/μL, 1900 cells/μL, 2000 cells/μL, 2100 cells/μL, 2200 cells/μL, 2300 cells/μL, 2400 cells/μL, 2500 cells/μL, 2600 cells/μL, 2700 cells/μL, 2800 cells/μL, 2900 cells/μL, 3000 cells/μL, 3500 cells/μL, or 4000 cells/μL in terms of the number of CD45+ lymphocytes among lymphocytes. The particular value can be appropriately selected from a numerical range from, for example, 400 cells/μL to 4000 cells/μL. The numerical range is preferably, for example, from 450 cells/μL to 3500 cells/μL. The numerical range is more preferably, for example, from 500 cells/μL to 3000 cells/μL, further preferably, for example, from 1000 cells/µL to 1500 cells/µL, though the numerical range is not limited to these values. A value higher than the particular value selected from the numerical range can be used as the predetermined value.

The predetermined value can be determined from a value higher than a particular value such as 250 cells/µL, 300 cells/µL, 400 cells/µL, 500 cells/µL, 600 cells/µL, 700 cells/µL, 800 cells/µL, 900 cells/µL, 1000 cells/µL, 1100 cells/µL, 1200 cells/µL, 1250 cells/µL, 1300 cells/µL, 1400 cells/µL, 1500 cells/µL, 1600 cells/µL, 1700 cells/µL, 1800 cells/µL, 1900 cells/µL, 2000 cells/µL, 2100 cells/µL, 2200 cells/µL, 2300 cells/µL, 2400 cells/µL, 2500 cells/µL, 3000 cells/µL, in terms of the number of CD3+ T cell. The particular value can be appropriately selected from a numerical range from, for example, 250 cells/µL to 3000 cells/µL. The numerical range is preferably, for example, from 300 cells/µL to 2500 cells/µL. The numerical range is more preferably, for example, from 350 cells/µL to 2000 cells/µL, further preferably, for example, from 400 cells/µL to 1000 cells/µL, though the numerical range is not limited to these values. A value higher than the particular value selected from the numerical range can be used as the predetermined value.

The predetermined value can be determined from a value higher than a particular value such as 150 cells/µL, 200 cells/µL, 250 cells/µL, 300 cells/µL, 350 cells/µL, 400 cells/µL, 450 cells/µL, 500 cells/µL, 550 cells/µL, 600 cells/µL, 650 cells/µL, 700 cells/µL, 750 cells/µL, 800 cells/µL, 850 cells/µL, 900 cells/µL, 950 cells/µL, 1000 cells/µL, 1100 cells/µL, 1200 cells/µL, 1300 cells/µL, 1400 cells/µL, 1500 cells/µL, 1600 cells/µL, 1700 cells/µL, in terms of the number of CD4+ T cell. The particular value can be appropriately selected from a numerical range from, for example, 150 cells/µL to 1700 cells/µL. The numerical range is preferably, for example, from 200 cells/µL to 1500 cells/µL. The numerical range is more preferably, for example, from 250 cells/µL to 700 cells/µL, further preferably, for example, from 300 cells/µL to 600 cells/µL, though the numerical range is not limited to these values. A value higher than the particular value selected from the numerical range can be used as the predetermined value.

The predetermined value can be determined from a value higher than a particular value such as 50 cells/µL, 75 cells/µL, 100 cells/µL, 125 cells/µL, 150 cells/µL, 175 cells/µL, 200 cells/µL, 225 cells/µL, 250 cells/µL, 275 cells/µL, 300 cells/µL, 325 cells/µL, 350 cells/µL, 400 cells/µL, 500 cells/µL, in terms of the number of CD8+ T cell. The particular value can be appropriately selected from a numerical range from, for example, 50 cells/µL to 500 cells/µL. The numerical range is preferably, for example, from 50 cells/µL to 300 cells/µL. The numerical range is more preferably, for example, from 75 cells/µL to 275 cells/µL, further preferably, for example, from 100 cells/µL to 250 cells/µL, though the numerical range is not limited to these values. A value higher than the particular value selected from the numerical range can be used as the predetermined value.

The predetermined value can be determined from a value higher than a particular value such as 25 cells/µL, 50 cells/µL, 150 cells/µL, 175 cells/µL, 200 cells/µL, 225 cells/µL, 250 cells/µL, 300 cells/µL, 350 cells/µL, 400 cells/µL, 450 cells/µL, 500 cells/µL, 550 cells/µL, 600 cells/µL, 700 cells/µL, 800 cells/µL, in terms of the number of CD16+ NK cell. The particular value can be appropriately selected from a numerical range from, for example, 25 cells/µL to 800 cells/µL. The numerical range is preferably, for example, from 50 cells/µL to 700 cells/µL. The numerical range is more preferably, for example, from 100 cells/µL to 600 cells/µL, further preferably, for example, from 150 cells/µL to 300 cells/µL, though the numerical range is not limited to these values. A value higher than the particular value selected from the numerical range can be used as the predetermined value.

The predetermined value can be determined from a value higher than a particular value such as 20 cells/µL, 30 cells/µL, 40 cells/µL, 50 cells/µL, 60 cells/µL, 70 cells/µL, 80 cells/µL, 90 cells/µL, 100 cells/µL, 110 cells/µL, 120 cells/µL, 130 cells/µL, 140 cells/µL, 150 cells/µL, 200 cells/µL, 250 cells/µL, 300 cells/µL, 350 cells/µL, 400 cells/µL, in terms of the number of NKp46+ NK cell. The particular value can be appropriately selected from a numerical range from, for example, 20 cells/µL to 400 cells/µL. The numerical range is preferably, for example, from 30 cells/µL to 300 cells/µL. The numerical range is more preferably, for example, from 50 cells/µL to 250 cells/µL, further preferably, for example, from 100 cells/µL to 200 cells/µL, though the numerical range is not limited to these values. A value higher than the particular value selected from the numerical range can be used as the predetermined value.

The predetermined value can be determined from a value higher than a particular value such as 2 cells/µL, 3 cells/µL, 4 cells/µL, 5 cells/µL, 6 cells/µL, 7 cells/µL, 8 cells/µL, 9 cells/µL, 10 cells/µL, 11 cells/µL, 12 cells/µL, 13 cells/µL, 14 cells/µL, 15 cells/µL, 20 cells/µL, 25 cells/µL, 30 cells/µL, 40 cells/µL, in terms of the number of CD56−/CD16+ NK cell. The particular value can be appropriately selected from a numerical range from, for example, 2 cells/µL to 40 cells/µL. The numerical range is preferably, for example, from 2 cells/µL to 30 cells/µL. The numerical range is more preferably, for example, from 2 cells/µL to 20 cells/µL, further preferably, for example, from 3 cells/µL to 10 cells/µL, though the numerical range is not limited to these values. A value higher than the particular value selected from the numerical range can be used as the predetermined value.

In a non-limiting aspect, the method of the present invention comprises measuring an expression level of a molecule expressed on the immunocyte in a biological sample isolated from the patient, wherein when the expression level is a predetermined value, the efficacy of the GPC3-targeting drug therapy for cancer in the patient is predicted, expected, or determined or the continuation of the therapy is determined. Examples of the molecule expressed on the immunocyte for the measurement in the present invention include, but not limited to, CD16. The expression level of any one of such molecules may be measured and used as an index for predicting, expecting, or determining the efficacy of the GPC3-targeting drug therapy for cancer. Alternatively, the expression levels of two or more of these molecules in combination may be used as an index. The predetermined value, for example, for CD16, can be regarded as a predetermined value at which the effect of the GPC3-targeting drug therapy can be expected, provided that this value falls within a range higher than the average expression level of CD16 on immunocytes in a patient group for which the effect of the GPC3-targeting drug therapy on cancer cannot be confirmed among a plurality of cancer patients treated with the GPC3-targeting drug therapy. For example, the predetermined value can also be determined on the basis of the average expression level of CD16 in a patient group showing a tendency toward significantly prolonged PFS or significantly prolonged OS among a plurality of cancer patients treated with the GPC3-targeting drug therapy. For example, a predetermined value for selecting with a high probability a patient showing a tendency toward significantly prolonged PFS or significantly prolonged OS as a result of GPC3-targeting drug therapy can be determined by measuring the expression level of CD16 in a plurality of cancer patients and setting the predetermined value to a value higher than the median value thereof. In this context, a plurality of cancer patients may be any number of cancer patients as long as the predetermined value for the expression level of CD16 serving as a criterion for determining the efficacy of GPC3-targeting drug therapy or the continuation of the therapy can be calculated as a significant value. The number of cancer patients is preferably 100 or more, more preferably 150 or more. Specifically, the predetermined value can be determined from a value higher than a particular value such as 150000 mesf, 175000 mesf, 200000 mesf, 225000 mesf, 250000 mesf, 275000 mesf, 300000 mesf, 325000 mesf, 350000 mesf, 375000 mesf, 400000 mesf, 425000 mesf, 450000 mesf, 475000 mesf, 500000 mesf, 525000 mesf, 550000 mesf, 575000 mesf, 600000 mesf, 625000 mesf, 650000 mesf, 675000 mesf, 700000 mesf, 750000 mesf, or 800000 mesf, for example, in terms of the above-described flow cytometry measurement value of fluorescence intensity of CD16 on NK cells. The particular value can be appropriately selected from a numerical range from, for example, 150000 mesf to 800000 mesf. The numerical range is preferably, for example, from 200000 mesf to 700000 mesf. The numerical range is more preferably, for example, from 300000 mesf to 650000 mesf, further preferably, for example, from 350000 mesf to 600000 mesf, though the numerical range is not limited to these values. A value higher than the particular value selected from the numerical range can be used as the predetermined value.

In a non-limiting aspect, the method of the present invention comprises measuring ADCC activity against GPC3-expressing cells using an immunocyte in a biological sample isolated from the patient, wherein when the expression level of CD16 and/or CD107a on the immunocyte is a predetermined value, the efficacy of the GPC3-targeting drug therapy for cancer in the patient with high ADCC activity is predicted, expected, or determined or the continuation of the therapy is determined. In the present invention, the expression level of any one or both of CD16 and CD107a on the immunocyte may be measured and used as an index for predicting, expecting, or determining the efficacy of the GPC3-targeting drug therapy for cancer.

For example, the expression level of CD16 or CD107a on immunocytes in the biological samples of a patient group for which the effect of the GPC3-targeting drug therapy on cancer cannot be confirmed among a plurality of cancer patients treated with the GPC3-targeting drug therapy is compared between in the presence and in the absence of the GPC3-targeting drug. In the case of CD16, the predetermined value can be regarded as a predetermined value at which the effect of the GPC3-targeting drug therapy can be expected, provided that this value falls within a range lower than the average difference from the expression level in the absence of the GPC3-targeting drug. In the case of CD107a, the predetermined value can be regarded as a predetermined value at which the effect of the GPC3-targeting drug therapy can be expected, provided that this value falls within a range higher than the average difference from the expression level in the absence of the GPC3-targeting drug. For example, the expression level of CD16 or CD107a on immunocytes in the biological samples of a patient group showing a tendency toward significantly prolonged PFS or significantly prolonged OS among a plurality of cancer patients treated with the GPC3-targeting drug therapy is compared between in the presence and in the absence of the GPC3-targeting drug. The predetermined value can be determined on the basis of the average difference from the expression level in the absence of the GPC3-targeting drug. For example, the expression level of CD16 or CD107a on immunocytes in the biological samples of a plurality of cancer patients is compared between in the presence and in the absence of the GPC3-targeting drug. In the case of CD16, the predetermined value can be regarded as a predetermined value at which the effect of the GPC3-targeting drug therapy can be expected, provided that this value falls within a range lower than the median value of the difference from the expression level in the absence of the GPC3-targeting drug. In the case of CD107a, the predetermined value can be regarded as a predetermined value at which the effect of the GPC3-targeting drug therapy can be expected, provided that this value falls within a range higher than the median value of the difference from the expression level in the absence of the GPC3-targeting drug. In this context, a plurality of cancer patients may be any number of cancer patients as long as the predetermined value for the expression level of CD16 or CD107a serving as a criterion for determining the efficacy of GPC3-targeting drug therapy or the continuation of the therapy can be calculated as a significant value. The number of cancer patients is preferably 100 or more, more preferably 150 or more.

In the case of CD16, specific examples of the predetermined value include values lower than a particular value selected from a range from −10% to −95% when the CD16 expression level in the absence of the GPC3-targeting drug is subtracted from the expression level in the presence of the GPC3-targeting drug. The numerical range is preferably, for example, from −20% to −90%, more preferably, for example, from −50% to −90%, though the numerical range is not limited to these values.

In the case of CD107a, specific examples of the predetermined value include values higher than a particular value selected from a range from 5% to 70% when the CD16 expression level in the absence of the GPC3-targeting drug is subtracted from the expression level in the presence of the GPC3-targeting drug. The numerical range is preferably, for example, from 10% to 60%, more preferably, for example, from 25% to 60%, though the numerical range is not limited to these values.

The predetermined value of the number of an immunocyte and an expression level of a molecule expressed on the immunocyte can slightly vary depending on many factors, for example, the assay method used, the type of a sample for free GPC3 assay, storage conditions (e.g., temperature and duration) of the sample, and the ethnic identity of the patient. In the method for predicting, expecting, or determining the efficacy or determining the continuation of the therapy, the number of an immunocyte and an expression level of a molecule expressed on the immunocyte is measured in a biological sample, particularly peripheral blood isolated from the patient.

The number of an immunocyte and an expression level of a molecule expressed on the immunocyte can be measured in a sample isolated before and/or after the start of the GPC3-targeting drug therapy and may be measured in a plurality of samples collected at predetermined time intervals. When the number of an immunocyte and an expression level of a molecule expressed on the immunocyte in any one of the plurality of samples collected at predetermined time intervals is the predetermined number of an immunocyte and/or the expression level, the efficacy of the GPC3- targeting drug therapy for cancer in the patient is predicted, expected, or determined or the continuation of the therapy is determined. The predetermined time intervals are appropriately set. In a non-limiting aspect of the intervals, the samples can be collected at intervals of 1 day, 2 days, 3 days, 4 days, 5 days, 6 days, 7 days (i.e., 1 week), 8 days, 9 days, 10 days, 11 days, 12 days, 13 days, 14 days (i.e., 2 weeks), 15 days, 16 days, 17 days, 18 days, 19 days, 20 days, 21 days (i.e., 3 weeks), 22 days, 23 days, 24 days, 25 days, 26 days, 27 days, 28 days (i.e., 4 weeks), 29 days, 30 days, 1 month, 5 weeks, 6 weeks, 7 weeks, 8 weeks, 9 weeks, 10 weeks, 2 months, 3 months, 4 months, 5 months, or 6 months after the initial administration of the GPC3-targeting drug, or at arbitrary points in time between the start and completion of the therapy, for example, after 1, 2, 3, 4 or more treatment cycles. The dosing intervals, i.e., the treatment cycles, can be appropriately set. One non-limiting example thereof includes 1 day, 2 days, 3 days, 4 days, 5 days, 6 days, 7 days (i.e., 1 week), 8 days, 9 days, 10 days, 11 days, 12 days, 13 days, 14 days (i.e., 2 weeks), 15 days, 16 days, 17 days, 18 days, 19 days, 20 days, 21 days (i.e., 3 weeks), 22 days, 23 days, 24 days, 25 days, 26 days, 27 days, 28 days (i.e., 4 weeks), 29 days, 30 days, 1 month, 5 weeks, 6 weeks, 7 weeks, 8 weeks, 9 weeks, 10 weeks, 2 months, 3 months, 4 months, 5 months, or 6 months.

As described above, when the number of an immunocyte and/or the expression level of a molecule expressed on the immunocyte is a predetermined value, the efficacy of the GPC3-targeting drug therapy is determined. In this procedure, whether the patient has, in the Fcγ receptor type IIA and/or type IIIA genes, a polymorphism that results in homozygous or heterozygous Val at amino acid residue 158 of FcγRIIIA and/or a polymorphism that results in homozygous or heterozygous His at amino acid residue 131 of FcγRIIA may be taken into consideration. Specifically, when the number of an immunocyte and/or the expression level of a molecule expressed on the immunocyte in the patient is a predetermined value and the patient has a polymorphism that results in homozygous or heterozygous Val at amino acid residue 158 of FcγRIIIA and/or a polymorphism that results in homozygous or heterozygous His at amino acid residue 131 of FcγRIIA, the efficacy of the GPC3-targeting drug therapy is determined.

As described above, when the number of an immunocyte and/or the expression level of a molecule expressed on the immunocyte is a predetermined value, the continuation of the GPC3-targeting drug therapy is determined. In this procedure, whether the patient has, in the Fcγ receptor type IIA and/or type IIIA genes, a polymorphism that results in homozygous or heterozygous Val at amino acid residue 158 of FcγRIIIA and/or a polymorphism that results in homozygous or heterozygous His at amino acid residue 131 of FcγRIIA may be taken into consideration. Specifically, when the number of an immunocyte and/or the expression level of a molecule expressed on the immunocyte in the patient is a predetermined value and the patient has a polymorphism that results in homozygous or heterozygous Val at amino acid residue 158 of FcγRIIIA and/or a polymorphism that results in homozygous or heterozygous His at amino acid residue 131 of FcγRIIA, the continuation of the GPC3-targeting drug therapy is determined.

In this context, the phrase "having a polymorphism that results in homozygous or heterozygous Val at amino acid residue 158 of FcγRIIIA" corresponds to the case where the patient has a nucleotide sequence of Val homozygote (V/V) or heterozygote (V/F) when a nucleotide sequence encoding amino acid residue 158 of FcγRIIIA is confirmed according to the method described in the above paragraph "Confirmation of Fcγ receptor gene polymorphism". Also, the phrase "having a polymorphism that results in homozygous or heterozygous His at amino acid residue 131 of FcγRIIA" corresponds to the case where the patient has a nucleotide sequence of His homozygote (H/H) or heterozygote (H/R) when a nucleotide sequence encoding amino acid residue 131 of FcγRIIA is confirmed in the same way as above.

As described above, when the number of an immunocyte and/or the expression level of a molecule expressed on the immunocyte is a predetermined value, the efficacy of the GPC3-targeting drug therapy is determined. In this procedure, the expression level of GPC3 in a tissue, particularly, a cancer tissue (including a liver cancer tissue), isolated from the patient may be further taken into consideration. Specifically, when the expression level of GPC3 in a tissue, particularly, a cancer tissue (including a liver cancer tissue), isolated from the patient is equal to or larger than a particular evaluation score and the number of an immunocyte and/or the expression level of a molecule expressed on the immunocyte in the patient is a predetermined value, the efficacy of the GPC3-targeting drug therapy is determined.

As described above, when the number of an immunocyte and/or the expression level of a molecule expressed on the immunocyte is a predetermined value, the continuation of the GPC3-targeting drug therapy is determined. In this procedure, the expression level of GPC3 in a tissue, particularly, a cancer tissue (including a liver cancer tissue), isolated from the patient may be further taken into consideration. Specifically, when the expression level of GPC3 in a tissue, particularly, a cancer tissue (including a liver cancer tissue), isolated from the patient is equal to or larger than a particular evaluation score and the number of an immunocyte and/or the expression level of a molecule expressed on the immunocyte in the patient is a predetermined value, the continuation of the GPC3-targeting drug therapy is determined.

In a non-limiting aspect, examples of the case where the expression level of GPC3 in a tissue, particularly, a cancer tissue (including a liver cancer tissue), isolated from the patient is equal to or larger than a particular evaluation score can include a case where the expression level of GPC3 is equal to or larger than a predetermined immunohistochemical staining score. In a non-limiting aspect, examples of the case where the expression level of GPC3 is equal to or larger than a predetermined immunohistochemical staining score can include high expression and low or moderate expression (IHC total score: 7 or higher and lower than 7, respectively) in a composite score 1 calculated as a result of staining according to the method as described in WO2009/116659 (staining method 1). In a non-limiting aspect, alternative examples of the case where the expression level of GPC3 is equal to or larger than a predetermined immunohistochemical staining score can include GPC3-IHC scores (Composite score 2) of 1+, 2+, and 3+ calculated as a result of staining according to the staining method used for calculating Composite score 2 (staining method 2).

Drug and Preparation

In the present invention, the drug usually refers to an agent for the treatment or prevention of a disease or for examination or diagnosis. In the present invention, the phrase "GPC3-targeting drug which is to be administered to a cancer patient having a predetermined value of the number of an immunocyte and/or an expression level of a molecule expressed on the immunocyte in a biological sample isolated from the cancer patient before the start of GPC3-targeting drug therapy" may be translated into a "method for treating cancer, comprising administering a GPC3-targeting drug to a cancer patient having a predetermined value of the number of an immunocyte and/or an expression level of a molecule expressed on the immunocyte in a biological sample isolated from the cancer patient before the start of GPC3-targeting drug therapy" or may be translated into "use of a GPC3-targeting drug which is to be administered to a cancer patient having a predetermined value of the number of an immunocyte and/or an expression level of a molecule expressed on the immunocyte in a biological sample isolated from the cancer patient before the start of GPC3-targeting drug therapy, for production of an agent for the treatment of cancer". In the present invention, the phrase "GPC3-targeting drug which is to be further administered to a cancer patient having a predetermined value of the number of an immunocyte and/or an expression level of a molecule expressed on the immunocyte in a biological sample isolated from the cancer patient after the start of GPC3-targeting drug therapy" may be translated into a "method for treating cancer, comprising further administering a GPC3-targeting drug to a cancer patient having a predetermined value of the number of an immunocyte and/or an expression level of a molecule expressed on the immunocyte in a biological sample isolated from the cancer patient after the start of GPC3-targeting drug therapy" or may be translated into "use of a GPC3-targeting drug which is to be further administered to a cancer patient having a predetermined value of the number of an immunocyte and/or an expression level of a molecule expressed on the immunocyte in a biological sample isolated from the cancer patient after the start of GPC3-targeting drug therapy, for production of an agent for the treatment of cancer".

The drug of the present invention can be formulated using a method generally known to those skilled in the art. For example, the drug of the present invention can be parenterally used in the form of an injection in a sterile solution or suspension with water or any other pharmaceutically acceptable solution. For example, the active ingredient can be appropriately combined with pharmacologically acceptable carriers or media, specifically, sterile water or saline, a plant oil, an emulsifier, a suspending agent, a surfactant, a stabilizer, a flavor, an excipient, a vehicle, an antiseptic, a binder, and the like mixed therewith in a unit dosage form required for generally accepted pharmaceutical practice to produce preparations. The amount of the active ingredient in these preparations is set to give an appropriate volume within a prescribed range.

Sterile compositions for injection can be formulated according to usual pharmaceutical practice using a vehicle such as injectable distilled water. Examples of injectable aqueous solutions include saline and isotonic solutions containing glucose or other adjuvants (e.g., D-sorbitol, D-mannose, D-mannitol, and sodium chloride). An appropriate solubilizer, for example, an alcohol (ethanol, etc.), a polyalcohol (propylene glycol, polyethylene glycol, etc.), or a nonionic surfactant (Polysorbate 80™, HCO-50, etc.) may be used in combination therewith.

Examples of oil solutions include sesame oil and soybean oil. Benzyl benzoate and/or benzyl alcohol may be used as a solubilizer in combination therewith. These injectable solutions may be mixed with a buffer (e.g., a phosphate buffer solution and a sodium acetate buffer solution), a soothing agent (e.g., procaine hydrochloride), a stabilizer (e.g., benzyl alcohol and phenol), and an antioxidant. The prepared injections are usually charged into appropriate ampules.

The drug of the present invention is preferably administered by parenteral administration. For example, the drug is administered in a dosage form of an injection, a transnasal agent, a transpulmonary agent, or a percutaneous agent. The drug can be administered systemically or locally by, for example, intravenous injection, intramuscular injection, intraperitoneal injection, or subcutaneous injection.

The administration method can be appropriately selected according to the age and symptoms of the patient. The single dose of a pharmaceutical preparation containing the drug can be set within the range of, for example, 0.0001 mg to 1000 mg per kg body weight. Alternatively, the dose can be set to, for example, 0.001 to 100000 mg per patient, though the dose of the present invention is not necessarily limited to these numeric values. The dose and the administration method vary depending on the body weight, age, symptoms, etc. of the patient. Those skilled in the art can set an appropriate dose and administration method in consideration of these conditions. As a preferred example of the dose and the administration method of the present invention, the drug of the present invention can be administered to achieve a blood trough level equal to or higher than a predetermined level in the patient. Preferred examples of the blood trough level can include 150 µg/mL or higher, 160 µg/mL or higher, 170 µg/mL or higher, 180 µg/mL or higher, 190 µg/mL or higher, 200 µg/mL or higher, 210 µg/mL or higher, 220 µg/mL or higher, 230 µg/mL or higher, 240 µg/mL or higher, 250 µg/mL or higher, 260 µg/mL or higher, 270 µg/mL or higher, 280 µg/mL or higher, 290 µg/mL or higher, 300 µg/mL or higher, and 400 µg/mL or higher. More preferred examples thereof can include 200 µg/mL or higher.

The preparation of the present invention comprises an instruction stating that the preparation is to be further administered to a cancer patient having a predetermined value of the number of an immunocyte and/or an expression level of a molecule expressed on the immunocyte in a biological sample isolated from the cancer patient after the start of GPC3-targeting drug therapy. In another non-limiting aspect, the preparation of the present invention comprises an instruction stating that the preparation is to be further administered to a cancer patient in which the number of an immunocyte and/or an expression level of a molecule expressed on the immunocyte in the biological sample isolated from the cancer patient after the start of GPC3-targeting drug therapy has been increased as a result of receiving the GPC3-targeting drug therapy.

In a non-limiting aspect, the present invention provides the preparation comprising an instruction stating that the patient is selected on the basis of a method comprising measuring the number of an immunocyte and/or an expression level of a molecule expressed on the immunocyte in a biological sample isolated from the patient treated with the GPC3-targeting drug therapy, wherein when the number of an immunocyte and/or an expression level of a molecule expressed on the immunocyte is a predetermined value, the efficacy of the GPC3-targeting drug therapy is determined or the continuation of the therapy is determined.

In a non-limiting aspect, the present invention provides the preparation comprising an instruction stating that the patient is selected on the basis of a method comprising measuring the number of an immunocyte and/or an expression level of a molecule expressed on the immunocyte in a biological sample isolated from the patient, wherein when the number of the immunocyte and/or the expression level are predetermined value, the efficacy of the GPC3-targeting drug therapy for cancer in the patient is predicted, expected, or determined or the continuation of the therapy is determined. In this context, examples of the predetermined value described in the instruction include the predetermined value described in the method for determining the efficacy of GPC3-targeting drug therapy or the method for determining the continuation of GPC3-targeting drug therapy.

The predetermined value of the number of an immunocyte and/or an expression level of a molecule expressed on the immunocyte can slightly vary depending on many factors, for example, the assay method used, the type of a sample for measuring the number of an immunocyte and an expression level of a molecule expressed on the immunocyte, storage conditions (e.g., temperature and duration) of the sample, and the ethnic identity of the patient. In the method for predicting, expecting, or determining the efficacy or determining the continuation of the therapy, a value in a biological sample, particularly peripheral blood isolated from the patient is measured as the predetermined value of the number of an immunocyte and/or an expression level of a molecule expressed on the immunocyte.

The number of an immunocyte and/or an expression level of a molecule expressed on the immunocyte can be measured in a sample isolated before and/or after the start of the GPC3-targeting drug therapy and may be measured in a plurality of samples collected at predetermined time intervals. When the number of an immunocyte and/or an expression level of a molecule expressed on the immunocyte in any one of the plurality of samples collected at predetermined time intervals is the predetermined value, the efficacy of the GPC3-targeting drug therapy for cancer in the patient is predicted, expected, or determined or the continuation of the therapy is determined. The predetermined time intervals at which the sample is collected after the start of the GPC3-targeting drug therapy are appropriately set. In a non-limiting aspect of the intervals, the samples can be collected at intervals of 1 day, 2 days, 3 days, 4 days, 5 days, 6 days, 7 days (i.e., 1 week), 8 days, 9 days, 10 days, 11 days, 12 days, 13 days, 14 days (i.e., 2 weeks), 15 days, 16 days, 17 days, 18 days, 19 days, 20 days, 21 days (i.e., 3 weeks), 22 days, 23 days, 24 days, 25 days, 26 days, 27 days, 28 days (i.e., 4 weeks), 29 days, 30 days, 1 month, 5 weeks, 6 weeks, 7 weeks, 8 weeks, 9 weeks, 10 weeks, 2 months, 3 months, 4 months, 5 months, or 6 months after the initial administration of the GPC3-targeting drug, or at arbitrary points in time between the start and completion of the therapy, for example, after 1, 2, 3, 4 or more treatment cycles. The dosing intervals, i.e., the treatment cycles, can be appropriately set. One non-limiting example thereof includes 1 day, 2 days, 3 days, 4 days, 5 days, 6 days, 7 days (i.e., 1 week), 8 days, 9 days, 10 days, 11 days, 12 days, 13 days, 14 days (i.e., 2 weeks), 15 days, 16 days, 17 days, 18 days, 19 days, 20 days, 21 days (i.e., 3 weeks), 22 days, 23 days, 24 days, 25 days, 26 days, 27 days, 28 days (i.e., 4 weeks), 29 days, 30 days, 1 month, 5 weeks, 6 weeks, 7 weeks, 8 weeks, 9 weeks, 10 weeks, 2 months, 3 months, 4 months, 5 months, or 6 months.

As described above, the instruction states that when the number of an immunocyte and/or the expression level of a molecule expressed on the immunocyte is a predetermined value, the GPC3-targeting drug therapy is effective. In this case, the instruction may state that whether the patient has, in the Fcγ receptor type IIA and/or type IIIA genes, a polymorphism that results in homozygous or heterozygous Val at amino acid residue 158 of FcγRIIIA and/or a polymorphism that results in homozygous or heterozygous His at amino acid residue 131 of FcγRIIA is also taken into consideration. Specifically, the instruction may state that when the number of an immunocyte and/or the expression level of a molecule expressed on the immunocyte in the patient is a predetermined value and the patient has a polymorphism that results in homozygous or heterozygous Val at amino acid residue 158 of FcγRIIIA and/or a polymorphism that results in homozygous or heterozygous His at amino acid residue 131 of FcγRIIA, the efficacy of the GPC3-targeting drug therapy is determined.

As described above, the instruction states that when the number of an immunocyte and/or the expression level of a molecule expressed on the immunocyte is a predetermined value, the continuation of the GPC3-targeting drug therapy is determined. In this case, the instruction may state that whether the patient has, in the Fcγ receptor type IIA and/or type IIIA genes, a polymorphism that results in homozygous or heterozygous Val at amino acid residue 158 of FcγRIIIA and/or a polymorphism that results in homozygous or heterozygous His at amino acid residue 131 of FcγRIIA is also taken into consideration. Specifically, the instruction may state that when the number of an immunocyte and/or the expression level of a molecule expressed on the immunocyte in the patient is a predetermined value and the patient has a polymorphism that results in homozygous or heterozygous Val at amino acid residue 158 of FcγRIIIA and/or a polymorphism that results in homozygous or heterozygous His at amino acid residue 131 of FcγRIIA, the continuation of the GPC3-targeting drug therapy is determined.

In this context, the phrase "having a polymorphism that results in homozygous or heterozygous Val at amino acid residue 158 of FcγRIIIA" corresponds to the case where the patient has a nucleotide sequence of Val homozygote (V/V) or heterozygote (V/F) when a nucleotide sequence encoding amino acid residue 158 of FcγRIIIA is confirmed according to the method described in the above paragraph "Confirmation of Fcγ receptor gene polymorphism". Also, the phrase "having a polymorphism that results in homozygous or heterozygous His at amino acid residue 131 of FcγRIIA" corresponds to the case where the patient has a nucleotide sequence of His homozygote (H/H) or heterozygote (H/R) when a nucleotide sequence encoding amino acid residue 131 of FcγRIIA is confirmed in the same way as above.

As described above, the instruction states that when the number of an immunocyte and/or the expression level of a molecule expressed on the immunocyte is a predetermined value, the efficacy of the GPC3-targeting drug therapy is determined. In this case, the instruction may state that the expression level of GPC3 in a tissue, particularly, a cancer tissue (including a liver cancer tissue), isolated from the patient is further taken into consideration. Specifically, the instruction may state that when the expression level of GPC3 in a tissue, particularly, a cancer tissue (including a liver cancer tissue), isolated from the patient is equal to or larger than a particular evaluation score, particularly, a cancer tissue (including a liver cancer tissue), isolated from the patient is equal to or larger than a particular evaluation score and the number of an immunocyte and/or the expression level of a molecule expressed on the immunocyte in the patient is a predetermined value, the efficacy of the GPC3-targeting drug therapy is determined.

As described above, the instruction states that when the number of an immunocyte and/or the expression level of a molecule expressed on the immunocyte is a predetermined value, the continuation of the GPC3-targeting drug therapy is determined. In this case, the instruction may state that the expression level of GPC3 in a tissue, particularly, a cancer tissue (including a liver cancer tissue), isolated from the patient is further taken into consideration. Specifically, the instruction may state that when the expression level of GPC3 in a tissue, particularly, a cancer tissue (including a liver cancer tissue), isolated from the patient is equal to or larger than a particular evaluation score and the number of an immunocyte and/or the expression level of a molecule expressed on the immunocyte in the patient is a predetermined value, the continuation of the GPC3-targeting drug therapy is determined.

In a non-limiting aspect, examples of the case where the expression level of GPC3 in a tissue, particularly, a cancer tissue (including a liver cancer tissue), isolated from the patient is equal to or larger than a particular evaluation score can include a case where the expression level of GPC3 is equal to or larger than a predetermined immunohistochemical staining score. In a non-limiting aspect, examples of the case where the expression level of GPC3 is equal to or larger than a predetermined immunohistochemical staining score can include high expression and low or moderate expression (IHC total score: 7 or higher and lower than 7, respectively) in a composite score 1 calculated as a result of staining according to the method as described in WO2009/116659 (staining method 1). In a non-limiting aspect, alternative examples of the case where the expression level of GPC3 is equal to or larger than a predetermined immunohistochemical staining score can include GPC3-IHC scores (Composite score 2) of 1+, 2+, and 3+ calculated as a result of staining according to the staining method used for calculating Composite score 2 (staining method 2).

Hereinafter, the present invention will be described specifically with reference to Examples. However, the present invention is not limited by these Examples.

Example 1

GC33 (generic name: codrituzumab) used in the present Examples is a recombinant humanized IgG1 monoclonal antibody capable of binding to human GPC3 with high affinity (WO2006/006693). In order to confirm the effect of GC33 on patients who had advanced and/or recurrent hepatocellular cancer (HCC) and had experienced the progression of the condition after radical cure by systemic therapy with at least a single agent or patients with unresectable advanced and/or metastatic hepatocellular cancer for which medication had been discontinued due to adverse events, a phase-II multicenter randomized double-blind placebo-controlled clinical trial was carried out (NP-27884 test). In this test chiefly aimed at evaluating efficacy on the basis of a progression-free survival duration in the patients with advanced and/or metastatic HCC and secondarily aimed at evaluating efficacy with an overall survival duration, a disease control rate, and a progression-free duration as indexes, evaluating safety and/or tolerability, confirming the pharmacokinetic profile of GC33, and searching for a biomarker, GC33 (1,600 mg) was administered by injection through an intravenous drip to each HCC patient once a week for the first two weeks and once two weeks thereafter.

The HCC patients subjected to the administration had histologically confirmed advanced or metastatic HCC (except for fibrolamellar type) unsuitable for curative therapy (surgical resection, liver transplantation, etc.) and/or local therapy or exacerbated after treatment and had a past history of treatment based on systemic therapy with at least one agent. Eligible patients were at least 18 years old with the capability of providing a tumor sample for GPC3 assay and exhibited Eastern Cooperative Oncology Group Performance Status of 0 or 1 and Child-Pugh class A. The patients also had at least one lesion that was evaluable according to the response evaluation criteria in solid tumors (RECIST).

Appropriate hematopoietic functions (absolute neutrophil count≥1500/μl, platelet≥50000/μl, hemoglobin≥8.0 g/dl), hepatic functions (total bilirubin ≤2 mg/dl, aspartate aminotransferase and alanine aminotransferase ≤5 times the upper limit of the normal level), and renal functions (serum creatinine≤twice the upper limit of the normal level) were evaluated as other criteria. Registrable female subjects were premenopausal female patients confirmed to be negative for a serum pregnancy test conducted within 10 days before the start of administration of the study drug, women without the possibility of pregnancy as a result of surgical contraception or after a lapse of 1 year or longer after menopause, and female patients other than the postmenopausal women (12-month or longer absence of menstruation) or the surgically contracepted women (resection of the ovary and/or the uterus), who consented to use two types of appropriate fertility control methods during clinical trial treatment and for at least 3 months or longer after the completion of administration of the study drug. Registrable male subjects were patients who consented to use fertility control based on the barrier method during clinical trial treatment and for at least 40 days after the completion of administration of the study drug. On the other hand, the registered subjects excluded patients who received major surgical operation within 2 weeks before the administration of the GPC3-targeting drug or did not get over severe disorder, patients confirmed to have brain or leptomeningeal metastasis, patients having a past history of malignant tumor within the last 5 years, patients having active infection requiring treatment except for hepatitis B or hepatitis C, patients having a past history of NCI-CTCAE v4.0 Grade 3 or higher hemorrhage within 4 weeks before the start of administration of the study drug, patients having a past history of organ transplantation including liver transplantation, patients who were scheduled to receive or were receiving the administration of an anticancer agent other than the agent to be administered in this test, patients who received the administration of an anticancer agent within 2 weeks before trial registration, patients who did not completely get over adverse reactions associated with the preceding locoregional or systemic therapy of hepatocellular cancer, patients under interferon therapy, patients who had baseline QTc exceeding 470 ms or exhibited baseline resting bradycardia (less than 45 beads/min.), patients who received the administration of an anticoagulant or a thrombolytic agent for therapeutic purposes within 2 weeks before the start of administration of the study drug (except for the administration of the agent at a low dose for the purpose of removing clogs in a catheter or for preventive purposes), pregnant or nursing patients, HIV-positive patients or patients having an AIDS-related disease, patients having a past history of hypersensitivity for similar agents (monoclonal antibodies, protein-containing preparations, and Chinese hamster ovary-derived preparations), and patients having a serious comorbidity judged by a principal investigator or a sub-investigator as being possibly worsened due to the study drug.

The protocol was carried out according to the guideline of the Good Clinical Practice (GCP) and approved by each participating ethical committee on clinical trials. All patients signed their names on written informed consent before registration. The patients received the continuous administration of GC33 unless the disease progressed or unacceptable toxicity appeared. Tumor was evaluated on the basis of a baseline and evaluated after 4 cycles, 7 cycles, and 10 cycles from the start of administration and then repetitively every four cycles until the disease progressed. Each cycle involved two weeks. The state of the disease was evaluated by principal investigators.

These patients were randomized to a GC33 group (the fixed dose of 1600 mg was administered every other week after administration of two doses at a 1-week interval; n=121 cases) or a placebo group (n=60 cases) at a ratio of 2:1 and stratified to 3 cohorts on the basis of GPC3 expression levels (Composite score 2) (0, 1+, and 2+/3+) by IHC staining using GPC3-IHC kit (manufactured by Ventana Medical Systems, Inc.). Primary analysis was carried out at the time of occurrence of progression-free survival (PFS) events in 128 cases planned in the protocol.

The expression of GPC3 proteins in HCC tumor tissues was evaluated by GPC3 immunohistochemical staining (GPC3-IHC), namely Composite score 2. The median measurement of GPC3-IHC was carried out by Ventana Medical Systems, Inc. (USA). Unstained slides of HCC tumor tissues prepared from tumor blocks formalin-fixed and paraffin-embedded after excision by needle biopsy in each hospital were subjected to immunohistochemical staining. The antibody used was a mouse GC33 antibody (manufactured by Ventana Medical Systems, Inc.).

Example 2

Once the PFS events of 128 cases were obtained from among 121 GC33-administered cases and 60 placebo-administered cases as described above, the effects of administration of GC33 in GPC3-targeting treatment were evaluated on the basis of PFS. In addition, overall survival (OS) was evaluated as a secondary endpoint when reaching 92 events. As a result, the administration of GC33 was confirmed to be not effective for prolonging both PFS and OS (FIG. 1), which was confirmed in the evaluation using each of the GPC-IHC scores (Comosite score 2)

The GC33-administered group was further divided into two groups (a group exposed to GC33 at a lower level than a cutoff value: low-GC33-exposed group, and a group exposed to GC33 at a higher level than a cutoff value: high-GC33-exposed group) using, as the cutoff value, the median value 230 μg/ml of putative blood trough levels of GC33 before administration of day 1 in the 3rd cycle (on the 4th week from the start of initial administration) based on population PK models obtained using the serum GC33 concentration values of this phase-II clinical trial. The progression-free survival duration or progression-free survival (PFS) or the overall survival duration or overall survival (OS) was compared as an index for clinical effects between these groups or between these groups and the placebo group by the Kaplan-Meier method. As a result, the effect of prolonging both PFS and OS was found in the high-GC33-exposed group compared with the placebo group or the low-GC33-exposed group (FIG. 2).

Immunocytes in peripheral blood, a polymorphism in the gene of Fc gamma receptor type IIA or IIIA expressed on immunocytes, and antibody-dependent cellular cytotoxicity activity (ADCC activity) in peripheral blood before the administration of GC33 were further assayed for the purpose of searching for a biomarker associated with the effect of GC33. PFS or OS was compared between groups by the Kaplan-Meier method in the same way as above. The log-rank test was conducted.

Example 3

In order to study the relation of the effect of GC33 to the number of peripheral blood immunocytes measured as a GC33 effect-related biomarker by a usual method (method using an automatic blood cell counter) after blood collection from cases in each center, these cases were divided into high-value groups and low-value groups on the basis of the median values of the numbers of various types of immunocytes in the peripheral blood of the patients before the administration of GC33. PFS and OS were compared between a GC33-administered group and a placebo group. As a result, as shown in Table 4, the administration of GC33 was confirmed to prolong PFS in the groups with a large number of leukocytes, monocytes, or neutrophils compared with the placebo groups. By contrast, no such effect was confirmed in the groups with a small number of each immunocyte (smaller than the median value). Particularly, as for the neutrophils, significantly prolonged PFS was confirmed in the group with a large number of cells (FIG. 3).

Further study was limited to the high-GC33-exposed groups confirmed above to have prolonged PFS and OS compared with the placebo groups. Significantly prolonged PFS as well as prolonged OS was confirmed in all the groups with a large number of leukocytes, monocytes, or neutrophils (the number of leukocytes: 5,680 cells/μL, the number of monocytes: 503 cells/μL, the number of neutrophils: 3,607 cells/μL). As for the number of lymphocytes, a tendency toward prolonged PFS as well as significantly prolonged OS was also confirmed only in the group with a large number of lymphocytes 1,246 cells/μL) (Table 4).

TABLE 4

Effect of GC33 on patients stratified depending on the number of immunocyte in peripheral blood

| | | Placebo vs. GC33 | | | | Placebo group vs. high-GC33-exposed group | | | |
|---|---|---|---|---|---|---|---|---|---|
| | | PFS | | OS | | PFS | | OS | |
| | | Hazard ratio | p value (log-rank) | Hazard ratio | p value (log-rank) | Hazard ratio | p value (log-rank) | Hazard ratio | p value (log-rank) |
| The number of leukocyte | Low value | 1.130 | 0.595 | 0.954 | 0.864 | 0.923 | 0.756 | 0.612 | 0.123 |
| | High value | 0.752 | 0.195 | 0.862 | 0.583 | 0.507 | 0.014 | 0.461 | 0.035 |
| The number of monocyte | Low value | 1.172 | 0.500 | 0.795 | 0.411 | 0.997 | 0.992 | 0.513 | 0.036 |
| | High value | 0.709 | 0.121 | 0.988 | 0.964 | 0.419 | 0.003 | 0.544 | 0.087 |
| The number of neutrophil | Low value | 1.229 | 0.369 | 1.004 | 0.988 | 1.082 | 0.754 | 0.682 | 0.222 |
| | High value | 0.607 | 0.030 | 0.796 | 0.390 | 0.311 | 0.000 | 0.361 | 0.008 |
| The number of lymphocyte | Low value | 0.944 | 0.802 | 1.063 | 0.826 | 0.738 | 0.240 | 0.666 | 0.196 |
| | High value | 0.938 | 0.773 | 0.759 | 0.307 | 0.658 | 0.128 | 0.404 | 0.017 |

Example 4

In order to identify various types of immunocytes in more detail, median measurement was carried out in Covance Inc. by FACS using antibodies against the surface antigens of various types of immunocytes and collected peripheral blood. As shown in Table 5, an antibody against each of lymphocyte markers CD19, CD45, CD3, CD4, and CD8 was mixed with collected whole blood. Lymphocyte subsets were assayed using Trucount tubes (manufactured by Becton, Dickinson and Company) and classified into low-value groups and high-value groups on the basis of the median values of the measurement values. As a result, significantly prolonged PFS was confirmed in the GC33-administered group with a large number of CD4-positive T cells (≥490 cells/μL) compared with the placebo group (FIG. 4).

In addition, a tendency toward prolonged OS was confirmed in the group with a large number of CD45-positive cells (≥1,090 cells/μL); a tendency toward prolonged PFS and OS was confirmed in the group with a large number of CD3-positive T cells (≥752 cells/μL); and a tendency toward prolonged OS was confirmed in the group with a large number of CD4-positive T cells (≥490 cells/μL) (Table 5).

Further study was limited to the high-GC33-exposed groups. Significantly prolonged PFS and OS were confirmed only in all the groups with a large number of CD3-positive or CD4-positive cells (CD3: ≥752 cells/μL, CD4: ≥490 cells/μL) or with a small number of CD8-positive cells (<251 cells/μL) (Table 5). In the other fractions, the significant prolongation of some survival durations or some prolonging effect was observed, though a certain strong tendency was not obtained in the high-value group or the low-value group.

cell fraction, a CD56−/CD16+ NK cell fraction, a CD56dim/CD16− NK cell fraction, and a CD56dim/CD16bright NK cell fraction on the basis of CD16 positivity, NKp46 positivity, and the reactivity of the antibodies against CD56 and CD16.

The influence of GC33 administration on PFS and OS for each NK cell fraction is shown in Table 6. Of these NK cell fractions, a tendency toward significantly prolonged PFS and a prolonged OS by the administration of GC33 was confirmed only in the group with a high CD56−/CD16+ NK cell fraction (≥6.3 cells/μL) (FIG. 5). The effect of prolonging survival durations was further prominent in the comparison between the high-GC33-exposed group and the placebo group. In the other fractions, the significant prolongation of some survival durations or some prolonging effect was observed, though a certain strong tendency was not obtained in the high-value group or the low-value group.

In addition to fractionation based on each marker, the expression level of CD16 or NKp46 on NK cells was measured by FACS (FACSCanto II, manufactured by Becton, Dickinson and Company) in the same way as above. The cases were classified into high-expression groups and low-expression group on the basis of the median values of the measurement results. PFS and OS were compared between a GC33-administered group or a high-GC33-exposed group and a placebo group. For each expression level (mean equivalent soluble fluorescent level (MESF)), an MESF calibration curve was prepared on the basis of the fluorescence intensity of calibration beads (Quantum MESF bead standard, manufactured by Bang Laboratories, Inc.),

TABLE 5

Effect of GC33 on patients stratified depending on peripheral blood immunocyte marker

| | | Placebo vs. GC33 | | | | Placebo group vs. high-GC33-exposed group | | | |
|---|---|---|---|---|---|---|---|---|---|
| | | PFS | | OS | | PFS | | OS | |
| | | Hazard ratio | p value (log-rank) | Hazard ratio | p value (log-rank) | Hazard ratio | p value (log-rank) | Hazard ratio | p value (log-rank) |
| The number of CD19+ B cell | Low value | 0.798 | 0.353 | 1.192 | 0.579 | 0.647 | 0.114 | 0.621 | 0.212 |
| | High value | 0.984 | 0.941 | 0.667 | 0.125 | 0.746 | 0.264 | 0.508 | 0.032 |
| The number of CD45+ lymphocyte | Low value | 1.072 | 0.771 | 1.520 | 0.139 | 0.737 | 0.279 | 0.783 | 0.486 |
| | High value | 0.780 | 0.289 | 0.537 | 0.040 | 0.653 | 0.121 | 0.430 | 0.021 |
| The number of CD3+ T cell | Low value | 1.103 | 0.674 | 1.161 | 0.578 | 0.844 | 0.526 | 0.715 | 0.291 |
| | High value | 0.760 | 0.239 | 0.642 | 0.155 | 0.616 | 0.076 | 0.462 | 0.046 |
| The number of CD4+ T cell | Low value | 1.273 | 0.307 | 1.465 | 0.173 | 1.058 | 0.836 | 1.045 | 0.891 |
| | High value | 0.635 | 0.050 | 0.476 | 0.013 | 0.461 | 0.004 | 0.235 | 0.0002 |
| The number of CD8+ T cell | Low value | 0.849 | 0.490 | 0.924 | 0.776 | 0.586 | 0.052 | 0.506 | 0.041 |
| | High value | 0.932 | 0.762 | 0.779 | 0.387 | 0.815 | 0.451 | 0.622 | 0.176 |

Subsequently, more detailed analysis was carried out on NK cells. In the same way as above, median measurement was carried out in Covance Inc. using peripheral blood collected from patients. Classification based on FACS analysis using antibodies against CD3, CD16, and CD56 was carried out, also including the reactivity of antibodies against NKp46 and CD8. Groups having cells negative for reactivity with CD3 were classified into a CD56bright NK and the expression level (MESF) was calculated from the fluorescence intensity of an NK cell fraction. As a result, as shown in Table 6, a tendency toward significantly prolonged PFS and prolonged OS by the administration of GC33 was confirmed only in the group with a high expression level of CD16 (CD16 MESF) (≥372,254 mesf) (FIG. 6). The effect of prolonging survival durations was further prominent in the comparison between the high-GC33-exposed group and the placebo group.

TABLE 6

Effect of GC33 on patients stratified depending on various surface markers for peripheral blood NK cell

|  |  | Placebo vs. GC33 | | | | Placebo group vs. high-GC33-exposed group | | | |
|---|---|---|---|---|---|---|---|---|---|
|  |  | PFS | | OS | | PFS | | OS | |
|  |  | Hazard ratio | p value (log-rank) | Hazard ratio | p value (log-rank) | Hazard ratio | p value (log-rank) | Hazard ratio | p value (log-rank) |
| The number of CD16+ NK cell | Low value | 0.977 | 0.919 | 1.043 | 0.884 | 0.697 | 0.183 | 0.466 | 0.043 |
|  | High value | 0.743 | 0.244 | 0.727 | 0.309 | 0.618 | 0.101 | 0.595 | 0.148 |
| The number of NKp46+ NK cell | Low value | 1.095 | 0.714 | 1.027 | 0.926 | 0.805 | 0.443 | 0.613 | 0.159 |
|  | High value | 0.768 | 0.256 | 0.781 | 0.401 | 0.594 | 0.062 | 0.502 | 0.065 |
| The number of CD56bright NK cell | Low value | 0.913 | 0.706 | 1.206 | 0.527 | 0.709 | 0.207 | 0.686 | 0.286 |
|  | High value | 0.901 | 0.658 | 0.653 | 0.150 | 0.641 | 0.126 | 0.462 | 0.041 |
| The number of CD56−/CD16+ NK cell | Low value | 1.259 | 0.344 | 1.173 | 0.594 | 0.991 | 0.975 | 0.666 | 0.269 |
|  | High value | 0.571 | 0.022 | 0.615 | 0.110 | 0.405 | 0.002 | 0.425 | 0.020 |
| The number of CD56dim/CD16− NK cell | Low value | 0.935 | 0.780 | 0.932 | 0.811 | 0.684 | 0.166 | 0.499 | 0.053 |
|  | High value | 0.896 | 0.641 | 0.860 | 0.603 | 0.722 | 0.248 | 0.643 | 0.211 |
| The number of CD56dim/CD16bright NK cell | Low value | 0.982 | 0.937 | 0.946 | 0.845 | 0.688 | 0.174 | 0.431 | 0.024 |
|  | High value | 0.768 | 0.288 | 0.839 | 0.579 | 0.645 | 0.124 | 0.682 | 0.290 |
| CD16MESF | Low value | 1.130 | 0.612 | 1.152 | 0.631 | 0.908 | 0.724 | 0.758 | 0.421 |
|  | High value | 0.668 | 0.101 | 0.665 | 0.170 | 0.473 | 0.010 | 0.348 | 0.005 |
| NKp46 MESF | Low value | 0.818 | 0.419 | 0.958 | 0.884 | 0.668 | 0.144 | 0.746 | 0.374 |
|  | High value | 1.004 | 0.987 | 0.781 | 0.395 | 0.642 | 0.133 | 0.281 | 0.004 |

Example 5

The induction of ADCC has been reported as a mechanism of action of GC33 (Ishiguro T. et al., Cancer Res. 2008; 68: 9832-9838). Thus, ADCC activity was measured in patients before the administration of GC33 and studied for its relation to the effect of GC33.

The ADCC activity was studied as follows using peripheral blood collected from patients before the administration of GC33 or placebo: the collected peripheral blood was frozen in liquid nitrogen and stored at −150° C. After thawing of the peripheral blood, an RPMI II medium (manufactured by HyClone Laboratories, Inc.) containing IL-2 (manufactured by PeproTech) was added thereto. GC33 (0.5 μg/mL) and target cells were added to $1×10^5$ peripheral mononuclear cells cultured overnight, followed by culture at 37° C. for 1 hour. Monensin was further added thereto, followed by culture for 2 hours. Then, the peripheral mononuclear cells were harvested, and a mixed solution of antibodies against CD45, CD3, CD16, CD56, and CD107 was added thereto. The expression level of CD16 or CD107a on NK cells was measured by FACS (FACSCanto II, manufactured by Becton, Dickinson and Company). Also, the expression level of CD107a or CD16 on NK cells cultured after the addition of only target cells was used as a negative control, and a difference from the negative control was used as an index for ADCC activity. The target cells used were GPC3-expressing human liver cancer cell line HepG2 cells (ATCC) for assay of ADCC activity, and human chronic myeloid leukemia cell line K562 cells (ATCC) for assay of antibody-independent NK activity. The preparation of any sample and median measurement in the assay were carried out in Covance Inc.

A group with an expression level of CD107a higher than the median value (34.15%) was defined as a high-ADCC activity group, while a group with an expression level thereof lower than the median value was defined as a low-ADCC activity group. Also, a group with an expression level of CD16 lower than the median value (−64.33%) was defined as a high-ADCC activity group, while a group with an expression level thereof higher than the median value was defined as a low-ADCC activity group. PFS and OS were compared among a high-GC33-exposed group, a low-GC33-exposed group, and a placebo group of these groups. As a result, as shown in Table 7, significantly prolonged PFS and OS were confirmed only in the high-ADCC activity groups for both the indexes of CD107a and CD16 (FIGS. 7 and 8).

On the other hand, change in the expression of CD107a or CD16 on the K562 cells (median value of the amount of change in CD107a expression: 9.74%, median value of the amount of change in CD16 expression: −15.76%) was measured as NK activity. Unlike ADCC, significantly prolonged PFS or OS only in either the low-value group or the high-value group of NK activity was not confirmed (Table 7).

TABLE 7

Effect of GC33 on patients stratified depending on NK activity or ADCC activity using peripheral blood before administration

|  |  | Placebo group vs. high-GC33-exposed group | | | |
|---|---|---|---|---|---|
|  |  | PFS | | OS | |
|  |  | Hazard ratio | P value | Hazard ratio | P value |
| ADCC activity | | | | | |
| CD107a | Low | 0.536 | 0.047 | 0.538 | 0.124 |
|  | High | 0.513 | 0.038 | 0.303 | 0.003 |
| CD16 | Low | 0.340 | 0.001 | 0.305 | 0.003 |
|  | High | 0.813 | 0.521 | 0.575 | 0.182 |
| NK activity | | | | | |
| CD107a | Low | 0.555 | 0.085 | 0.338 | 0.013 |
|  | High | 0.601 | 0.127 | 0.406 | 0.048 |
| CD16 | Low | 0.506 | 0.044 | 0.295 | 0.013 |
|  | High | 0.573 | 0.117 | 0.390 | 0.026 |

Example 6

A polymorphism of the gene of an Fc gamma receptor binding to an antibody Fc region is known to influence its binding to the antibody Fc region. Thus, the effect of GC33 was studied for its relation to a polymorphism in Fc gamma receptor type IIA and IIIA genes. The genomic gene was isolated from peripheral blood collected from each patient. A polymorphism in a nucleotide sequence corresponding to amino acid residue 131 of Fc gamma receptor type IIA or a nucleotide sequence corresponding to amino acid residue 158 of type IIIA was measured. Specifically, the genomic DNA isolated using MagNa Pure LC DNA Isolation kit 1 (manufactured by Roche Applied Science) from whole blood collected from each patient was used to perform genotyping by real-time PCR using TaqMan® probe designed to correspond to each SNP.

PFS and OS were compared between a polymorphism that resulted in homozygous or heterozygous Val (V/V or V/F) at amino acid residue 158 of FcγRIIIA and a polymorphism that resulted in homozygous Phe (F/F) at this residue in each of a high-GC33-exposed group, a low-GC33-exposed group, and a placebo group. As a result, as shown in Table 8, significantly prolonged PFS and OS were both confirmed in the high-GC33-exposed group having V/V or V/F compared with the placebo group. By contrast, no such effect was confirmed in the group having F/F.

TABLE 8

Effect of GC33 on patients stratified depending on polymorphism in Fc gamma receptor gene
Placebo group vs. high-GC33-exposed group

| FcγRIIIA-158 | V/V or V/F | | F/F | |
|---|---|---|---|---|
| | Hazard ratio | P value | Hazard ratio | P value |
| PFS | 0.524 | 0.016 | 0.779 | 0.447 |
| OS | 0.442 | 0.039 | 0.628 | 0.288 |

| FcγRIIA-131 | H/H or H/R | | R/R | |
|---|---|---|---|---|
| | Hazard ratio | P value | Hazard ratio | P value |
| PFS | 0.565 | 0.011 | 0.948 | 0.925 |
| OS | 0.436 | 0.009 | 0.457 | 0.350 |

Also, a gene polymorphism related to residue 131 of FcγRIIA was studied in the same way as above. PFS and OS were compared between a polymorphism that resulted in homozygous or heterozygous His (H/H or H/R) at amino acid residue 131 and a polymorphism that resulted in homozygous Arg (R/R) at this residue in each of a high-GC33-exposed group, a low-GC33-exposed group, and a placebo group. As a result, as shown in Table 8, significantly prolonged PFS and OS were both confirmed in the high-GC33-exposed group having H/H or H/R compared with the placebo group. By contrast, no such effect was confirmed in the group having R/R.

These results demonstrated that the immune state of a patient can be improved by measuring each of the number of an immunocyte in peripheral blood, ADCC activity, or a polymorphism in Fc gamma receptor gene, or the efficacy of GPC3-targeting therapy can be improved by the combination thereof.

Example 7

With regard to the expression level of CD16 on NK cells (CD16 MESF), further analysis using Cox regression based on the proportional hazards model was performed. In the analysis, classification into CD16 MESF higher value groups and CD16 MESF lower value groups was performed based on the measurement results of Example 5 using different cut-off values, and the hazard ratio, 95% confidence interval (95% CI) and p-value of the log-rank test were calculated for each group. Here, the overall survival period was used as a variable response in the analysis and adjusted by clinically relevant background factors.

279,736.9 mesf, which was 33% (33 percentile value) of the CD16 MESF value, 363,594 mesf, which was 50% (50 percentile value), or 439,468.3, which was 67% (33 percentile value), were the cut-off values. Classification into lower value groups and higher value groups was performed respectively using respective different cut-off values, and the hazard ratios, 95% confidence intervals and p-values of the GC33 high exposure group were compared to those of the placebo group. As a result, the hazard ratio decreased as the cut-off value of the CD16 MESF value increased in the CD16 MESF higher value group as shown in Table 9, which suggested that the clinical efficacy of GC33 and the expression level of CD16 were relevant (Table 9).

On the other hand, no significant relationship was observed between the change of the cut-off value of the MESF values for CD16 and the hazard ratio in the CD16 MESF lower value group.

TABLE 9

The relationship between cut-off value of MESF value for CD16 and hazard ratio

| | CD16 MESF Higher Value Group | | | | | CD16 MESF Lower Value Group | | | | |
|---|---|---|---|---|---|---|---|---|---|---|
| CD16 MESF Cut-off Value | N | Hazard ratio | 95% CI Lower limit | 95% CI Upper limit | p-Value | N | Hazard ratio | 95% CI Lower limit | 95% CI Upper limit | p-Value |
| 33% Value | 71 | 0.44 | 0.22 | 0.88 | 0.020 | 36 | 1.55 | 0.38 | 6.35 | 0.543 |
| 50% Value | 54 | 0.33 | 0.14 | 0.77 | 0.011 | 53 | 1.46 | 0.55 | 4.11 | 0.459 |
| 67% Value | 36 | 0.09 | 0.02 | 0.44 | 0.003 | 71 | 1.03 | 0.50 | 2.12 | 0.928 |

All publications, patents, and patent applications cited herein are incorporated herein by reference in their entirety.

INDUSTRIAL APPLICABILITY

The present invention contributes to improvement in the efficacy of GPC3-targeting drug therapy and improvement in QOL of a patient to be treated, and is useful in the treatment of cancer including liver cancer.

What is claimed is:

1. A method for determining the efficacy of anti-Glypican 3 (GPC3) antibody therapy for GPC3 expressing solid cancer in a patient or determining the continuation of anti-GPC3 antibody therapy for a GPC3 expressing solid cancer patient treated with anti-GPC3 antibody therapy, said method comprising measuring the number of CD45$^+$ lymphocytes or CD56$^-$/CD16$^+$ NK cells in a peripheral blood sample isolated from the patient before the start of anti-GPC3 antibody therapy or the patient treated with the anti-GPC3 antibody therapy, wherein when the number of the CD45$^+$ lymphocytes or CD56$^-$/CD16$^+$ NK cells is a predetermined value, the anti-GPC3 antibody therapy is determined to be effective or the anti-GPC3 antibody therapy is determined to be continued, wherein (a) when the number measured is the number of CD45$^+$ lymphocytes, the predetermined value is more than a particular value selected from the range from 450 to 3500 cells/μL, or (b) when the number measured is the number of CD56⁻/CD16⁺ NK cells, the predetermined value is more than a particular value selected from the range from 2 to 30 cells/μL, said method further comprising administering the anti-GPC3 antibody to the patient for which the efficacy of the anti-GPC3 antibody therapy has been determined or the continuation of the anti-GPC3 antibody therapy has been determined, wherein the anti-GPC3 antibody comprises a member selected from the group consisting of:

(1) a heavy chain variable region having the amino acid sequence set forth in SEQ ID NO: 50 and a light chain variable region having the amino acid sequence set forth in SEQ ID NO: 51;
(2) a heavy chain variable region having the amino acid sequence set forth in SEQ ID NO: 50 and a light chain variable region having the amino acid sequence set forth in SEQ ID NO: 66;
(3) a heavy chain variable region having the amino acid sequence set forth in SEQ ID NO: 67 and a light chain variable region having the amino acid sequence set forth in SEQ ID NO: 68;
(4) a heavy chain variable region having the amino acid sequence set forth in SEQ ID NO: 69 and a light chain variable region having the amino acid sequence set forth in SEQ ID NO: 70;
(5) a heavy chain variable region having the amino acid sequence set forth in SEQ ID NO: 71 and a light chain variable region having the amino acid sequence set forth in SEQ ID NO: 72; and
(6) a heavy chain variable region having the amino acid sequence set forth in SEQ ID NO: 71 and a light chain variable region having the amino acid sequence set forth in SEQ ID NO: 73.

2. The method of claim 1, wherein the method comprises measuring the number of CD56⁻/CD16⁺ NK cells.

3. The method of claim 1, wherein the patient has a polymorphism resulting in a homozygous or heterozygous Val at amino acid residue 158 of human FcγRIIIA or a homozygous or heterozygous His at amino acid residue 131 of human FcγRIIA.

4. The method of claim 1, wherein the GPC3 expressing solid cancer is liver cancer.

5. The method of claim 1, wherein the anti-GPC3 antibody is administered to achieve a blood trough level of 200 μg/ml or higher in the patient.

6. The method of claim 1, wherein the anti-GPC3 antibody has antibody-dependent cellular cytotoxicity (ADCC) activity, complement-dependent cytotoxicity (CDC) activity, or ADCC and CDC activity.

7. The method of claim 1, wherein the anti-GPC3 antibody is conjugated with a cytotoxic substance.

8. The method of claim 1, wherein the anti-GPC3 antibody is administered to achieve a blood trough level of 230 μg/ml or higher in the patient.

9. The method of claim 1, wherein the method comprises measuring the number of CD45⁺ lymphocytes.

10. The method of claim 1, wherein
(a) when the number measured is the number of CD45⁺ lymphocytes, the predetermined value is more than a particular value selected from the range from 500 to 3000 cells/μL, or
(b) when the number measured is the number of CD56−/CD16⁺ NK cells, the predetermined value is more than a particular value selected from the range from 2 to 20 cells/μL.

\* \* \* \* \*